(12) United States Patent
Bender et al.

(10) Patent No.: US 12,087,282 B2
(45) Date of Patent: Sep. 10, 2024

(54) CROSS-CLASS ONTOLOGY INTEGRATION FOR LANGUAGE MODELING

(71) Applicant: Sorcero, Inc., Washington, DC (US)

(72) Inventors: Walter Bender, Washington, DC (US); Martin Abente Lahaye, Mariscal Estigarribia (PY); Christopher Liu, Washington, DC (US)

(73) Assignee: SORCERO, INC., Washington, DC (US)

( * ) Notice: Subject to any disclaimer, the term of this patent is extended or adjusted under 35 U.S.C. 154(b) by 0 days.

(21) Appl. No.: 18/489,212

(22) Filed: Oct. 18, 2023

(65) Prior Publication Data

US 2024/0127797 A1 Apr. 18, 2024

Related U.S. Application Data

(62) Division of application No. 17/210,315, filed on Mar. 23, 2021, now Pat. No. 11,854,531.

(Continued)

(51) Int. Cl.
*G06F 17/00* (2019.01)
*G06F 9/451* (2018.01)
(Continued)

(52) U.S. Cl.
CPC ............ *G10L 15/063* (2013.01); *G06F 9/451* (2018.02); *G06F 9/547* (2013.01);
(Continued)

(58) Field of Classification Search
None
See application file for complete search history.

(56) References Cited

U.S. PATENT DOCUMENTS 7,693,812 B2 * 4/2010 Lim .................. G06F 16/24564
707/999.001
8,782,039 B2 * 7/2014 Byrne ............... G06F 16/90335
707/723

(Continued)

OTHER PUBLICATIONS

Office Action for related Canada application No. 3,172,707 issued Mar. 12, 2024, pp. 1-5.

(Continued)

*Primary Examiner* — Satwant K Singh
(74) *Attorney, Agent, or Firm* — Pillsbury Winthrop Shaw Pittman, LLP

(57) ABSTRACT

Provided is a method including obtaining a set of ontologies mapping n-grams onto concepts to which the n-grams refer in different respective domains of knowledge. The method includes receiving an update associating a first n-gram with a first concept and receiving information by which the update is associated with a given domain of knowledge. The method includes selecting a subset of ontologies by determining that the update in the given domain of knowledge is applicable to respective domains of knowledge of the subset of ontologies and that the first concept has a specified type of relationship to a subset of concepts to which other n-grams are mapped in the subset of ontologies. The method also includes storing, in response to the determination, associations between the first n-gram and the subset of concepts in at least some of the subset of ontologies in memory of the computer system.

17 Claims, 24 Drawing Sheets

Related U.S. Application Data

(60) Provisional application No. 62/993,122, filed on Mar. 23, 2020.

(51) Int. Cl.

| | | |
|---|---|---|
| *G06F 9/54* | (2006.01) | |
| *G06F 16/22* | (2019.01) | |
| *G06F 16/248* | (2019.01) | |
| *G06F 16/31* | (2019.01) | |
| *G06F 16/33* | (2019.01) | |
| *G06F 16/332* | (2019.01) | |
| *G06F 16/34* | (2019.01) | |
| *G06F 16/36* | (2019.01) | |
| *G06F 16/9032* | (2019.01) | |
| *G06F 40/20* | (2020.01) | |
| *G06F 40/289* | (2020.01) | |
| *G06F 40/30* | (2020.01) | |
| *G06F 40/40* | (2020.01) | |
| *G06N 3/04* | (2023.01) | |
| *G06N 20/00* | (2019.01) | |
| *G10L 15/06* | (2013.01) | |
| *G10L 15/16* | (2006.01) | |
| *G10L 15/197* | (2013.01) | |
| *G16H 10/60* | (2018.01) | |
| *G16H 40/20* | (2018.01) | |
| *G16H 70/20* | (2018.01) | |

(52) U.S. Cl.
CPC ........ *G06F 16/2237* (2019.01); *G06F 16/248* (2019.01); *G06F 16/328* (2019.01); *G06F 16/3323* (2019.01); *G06F 16/3329* (2019.01); *G06F 16/3338* (2019.01); *G06F 16/3344* (2019.01); *G06F 16/3347* (2019.01); *G06F 16/345* (2019.01); *G06F 16/367* (2019.01); *G06F 16/90332* (2019.01); *G06F 40/20* (2020.01); *G06F 40/289* (2020.01); *G06F 40/30* (2020.01); *G06F 40/40* (2020.01); *G06N 3/04* (2013.01); *G06N 20/00* (2019.01); *G10L 15/16* (2013.01); *G10L 15/197* (2013.01); *G16H 10/60* (2018.01); *G16H 40/20* (2018.01); *G16H 70/20* (2018.01)

(56) References Cited

U.S. PATENT DOCUMENTS

| | | | |
|---|---|---|---|
| 9,378,273 B2 | | 6/2016 | Chu-Carroll et al. |
| 9,842,102 B2 * | | 12/2017 | Salome ................. G06F 40/289 |
| 11,151,982 B2 * | | 10/2021 | Tomkins ................. G06F 9/451 |
| 2016/0179945 A1 | | 6/2016 | Lastra Diaz et al. |
| 2016/0246780 A1 | | 8/2016 | Feller et al. |
| 2017/0132187 A1 | | 5/2017 | Contreras et al. |
| 2018/0143962 A1 | | 5/2018 | Tremblay et al. |
| 2018/0157741 A1 | | 6/2018 | Allen et al. |
| 2020/0042597 A1 | | 2/2020 | Wu |
| 2020/0327432 A1 | | 10/2020 | Doebelin et al. |
| 2021/0124783 A1 | | 4/2021 | Ben-Simhon et al. |
| 2021/0263898 A1 * | | 8/2021 | Lei ....................... G06F 16/9024 |
| 2022/0005463 A1 * | | 1/2022 | Bender ................ G06F 16/3347 |
| 2023/0139783 A1 * | | 5/2023 | Garib ..................... G06N 3/044 |
| | | | 707/769 |
| 2023/0360643 A1 * | | 11/2023 | Mittal ..................... G06N 5/022 |

OTHER PUBLICATIONS

Office Action for related Canada application No. 3,172,711 issued Mar. 20, 2024, pp. 1-4.

European Search Report for related application No. 21774053.9 issued Mar. 27, 2024, pp. 1-14.

Wu Pin et al.: "Template Oriented Text Summarization via Knowledge Graph", 2018 International Conference On Audio, Language and Image Processing (ICALIP), IEEE, Jul. 16, 2018 (Jul. 16, 2018), pp. 79-83, XP033398333.

Office Action for related Canada application No. 3,172,725 issued Mar. 27, 2024, pp. 1-4.

Office Action for related Canada application No. 3,172,717 issued Mar. 27, 2024, pp. 1-4.

Non-Final Office Action for related U.S. Appl. No. 18/465,895 issued Apr. 3, 2024, pp. 1-34.

Office Action for related Canada application No. 3,172,730 issued Apr. 4, 2024, pp. 1-6.

European Search Report for related application No. 21774179.2 issued Apr. 4, 2024, pp. 1-15.

European Search Report for related application No. 21775944.8 issued Apr. 5, 2024, pp. 1-15.

European Search Report for related application No. 21775528.9 issued Apr. 5, 2024, pp. 1-15.

Chungnan Lee et al.: "An embedded visual programming interface for intelligent information retrieval on the Web", Knowledge and Data Engineering Exchange Workshop, 1997. Proceedings Newport Beach, CA, USA Nov. 4, 1997, Los Alamitos, CA, USA, IEEE Comput. Soc, US, Jan. 1, 1997 (Jan. 1, 1997), pp. 46-53, XP010252140.

European Search Report for related application No. 21775453.0 issued Apr. 5, 2024, pp. 1-14.

* cited by examiner

CROSS-CLASS ONTOLOGY INTEGRATION FOR LANGUAGE MODELING

CROSS-REFERENCE TO RELATED APPLICATIONS

This patent application is a divisional of U.S. patent application Ser. No. 17/210,315, filed Mar. 23, 2021 and titled "CROSS-CLASS ONTOLOGY INTEGRATION FOR LANGUAGE MODELING", which claims the benefit of U.S. Provisional Patent Application 62/993,122, filed 23 Mar. 2020 and titled "MULTI-SCALE SUPPORT FOR NATURAL LANGUAGE UNDERSTANDING." The entirety of the content of each aforementioned patent filing is hereby incorporated by reference.

BACKGROUND

1. Field

The present disclosure relates generally to machine learning and, more specifically, to natural language processing for cross-context natural language model generation.

2. Description of the Related Art

Natural language understanding (NLU) is a sub-field of natural language processing (NLP). NLU operations and NLP operations are expected to impact a broad spectrum of disciplines such as computer operations, medicine, education, and finance. NLU operations can be used when storing, retrieving, or analyzing information in such fields. Furthermore, NLU operations can be performed on server-side devices or client-side devices and can provide information in response to queries.

SUMMARY

The following is a non-exhaustive listing of some aspects of the present techniques. These and other aspects are described in the following disclosure.

Some aspects include a process that includes obtaining a set of ontologies, where ontologies in the set of ontologies map n-grams onto concepts to which the n-grams refer in different respective domains of knowledge. The process also includes receiving an update associating a first n-gram with a first concept and receiving information by which the update is associated with a given domain of knowledge of a user providing the update. The process also includes selecting a subset of ontologies from among the set of ontologies by determining that the update in the given domain of knowledge is applicable to respective domains of knowledge of the subset of ontologies. The process also includes determining that the first concept has a specified type of relationship to a subset of concepts to which other n-grams are mapped in the subset of ontologies and storing in response to the determination, associations between the first n-gram and the subset of concepts in at least some of the subset of ontologies.

Some aspects include a process that includes obtaining a set of graphs comprising a first ontology graph associated with a first domain category value, the first ontology graph comprising a first vertex and a second vertex, and a second ontology graph associated with a second domain category value, the second ontology graph comprising a third vertex, where the second vertex is connected to the third vertex via a first graph edge. The process also includes obtaining an update associating a first n-gram with the second vertex, where the first vertex is mapped to the first n-gram, and where the first domain category value is associated with the update. The process also includes determining a first relationship type between the first vertex and the second vertex based on the update. The process also includes selecting the second ontology graph from amongst a plurality of ontology graphs based on the first domain category value and the second domain category value. The process also includes determining whether the first graph edge is associated with a second relationship type that satisfies a relationship criterion based on the first relationship type. The process also includes determining an association between the first n-gram indicated by the first vertex and a second n-gram associated with the third vertex. The process also includes updating the set of graphs, the updating comprising storing the association between the first n-gram and the second n-gram in memory.

Some aspects include a tangible, non-transitory, machine-readable medium storing instructions that when executed by a data processing apparatus cause the data processing apparatus to perform operations including one or more of the above-mentioned processes.

Some aspects include a system, including: one or more processors; and memory storing instructions that when executed by the processors cause the processors to effectuate operations of one or more of the above-mentioned processes.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
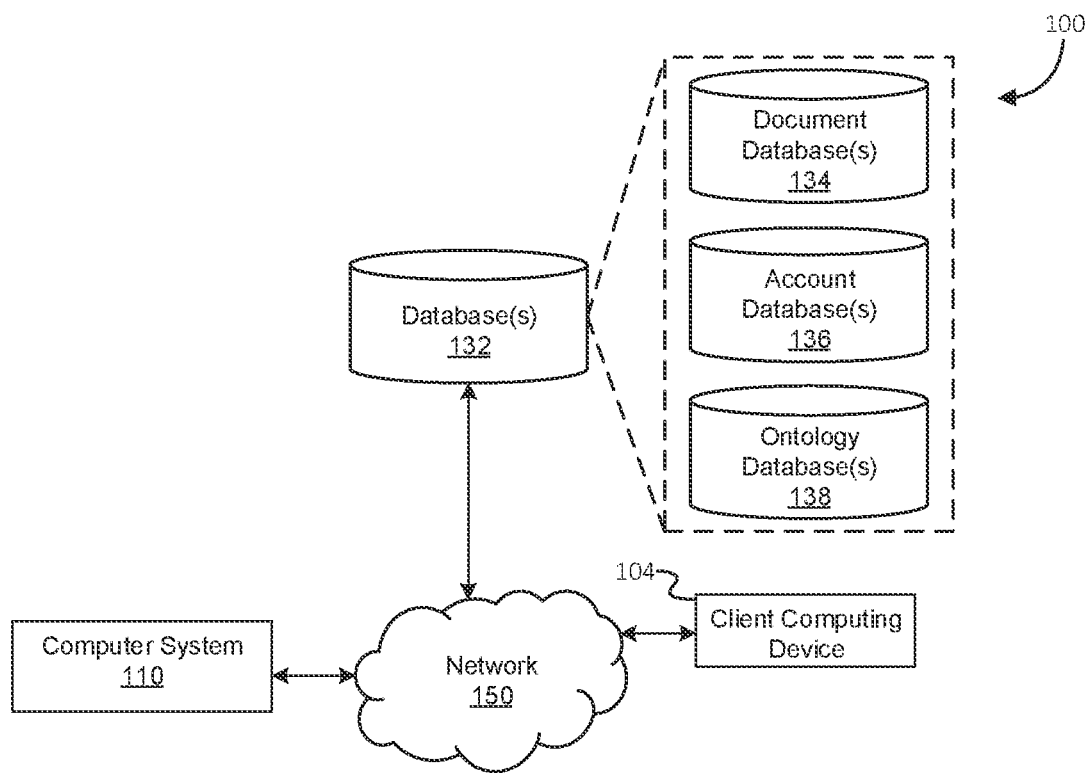
FIG. 1 is a schematic diagram of a first computing environment in which a score stored in an account may be updated, in accordance with some embodiments of the present technique.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the field of natural language processing. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Various search systems are capable of retrieving information in response to a query. However, while such systems may rank the relevance of retrieved data based on a number of matches with exact terms or metadata tags, such operations may be less useful when a user is generating queries with incomplete information or limited expertise. Furthermore, the usefulness of any retrieved information may be limited if a user's choice of words, choice of phrasing, or the context of the query itself is not taken into consideration. Retrieving meaningful information for a query under these conditions may require a different set of retrieval operations, where such operations may fall under the field of natural language understanding (NLU).

Some embodiments may address this issue by generating ontology graphs arranged in a hierarchical ontology data model based on ingested documents. Ontology graphs may be associated with their own domain categories or may be arranged into subgraphs having vertices associated with specific domain categories. Some embodiments may obtain a plurality of documents and a corresponding set of domain vectors, where the set of domain vectors may be sent directly via an Application Program Interface (API), provided via a user interface (UI) element, determined from other information, or the like. Such other information can include the document's origin, metadata associated with the document, a data format, or the like. A domain vector for a document can indicate various types of information relevant to the usefulness of the document, such as an associated expertise level for each of a plurality of domains, a count of words, a count of words having more than a specified number of syllables, or the like. Some embodiments may then use one or more machine learning models to determine learned representations, such as categories, scalar values, or embedding vectors, for the documents. The machine learning models may include a transformer neural network model such as Elmo, BERT, or the like. In some embodiments, the machine learning model may improve data ingestion accuracy by generating attention vectors for n-grams of an ingested document when performing document analysis or text summarization operations.

It should be understood that a set of ontology graphs may include a single ontology graph, and that some embodiments may include multiple domains or classes within a single ontology graph. Various categories may be used to categorize domain-related properties of an ontology graph and may be identified by a one or more domain category values. A domain category value may include a domain of knowledge ("domain"), a sub-domain of a domain, a class within a domain, or the like, where an ontology graph may be characterized by one or more domain category values. For example, an ontology graph may be characterized with a domain "cardiology" and a class value "3," where the domain and the class value identifying the domain of knowledge may be domain category values. Furthermore, while this disclosure may refer to a plurality of ontology graphs having different associated domains or domain classes within the domains, some embodiments may perform one or more operations described in this disclosure with one ontology graph. For example, some embodiments may use an ontology graph having different subgraphs, the different subgraphs having an associated different set of domains or classes within the domains. For example, some embodiments may store a single ontology graph and its vertices, where different sets of ontology graph vertices corresponding with different subgraphs of the ontology Alternatively, or in addition, some embodiments may perform one or more operations of this disclosure using a single ontology graph that include multiple vertices mapped to a same n-gram. For example, some embodiments may determine a first vertex and a second vertex of an ontology graph based on a shared n-gram, where the shared n-gram may be mapped to different learned representations determined from the shared n-gram based on the surrounding n-grams of the shared n-gram. As used in this disclosure, an n-gram may map to a vertex of an ontology graph if an embedding vector of the n-gram or other learned representation of the n-gram may be used to identify the vertex.

Some embodiments may identify a vertex of an ontology graph based on a first embedding vector by matching the first embedding vector with a set of embedding vectors corresponding with a set of vertices of the ontology graph. Alternatively, or in addition, some embodiments may identify a vertex of an ontology graph based on a first embedding vector by determining a closest embedding vector in an embedding space with respect to the first embedding vector and selecting the vertex mapped to the closest embedding vector. Alternatively, or in addition some embodiments may identify a vertex of an ontology graph based on a first embedding vector and a distance threshold. For example, some embodiments may determine a distance between a second embedding vector and the first embedding vector in an embedding space and select the vertex mapped to the second embedding vector based on the distance satisfying a distance threshold. Furthermore, some embodiments may select a second vertex mapped to a second embedding vector based on the distance satisfying the distance threshold and the second embedding vector being the closest embedding vector with respect to the first embedding vector.

Some embodiments may update an ontology graph based on the embedding vectors or other learned representations representing words or other n-grams of the plurality of documents, where the ontology graph may be usable as an index for the plurality of documents. The ontology graph may include vertices representing different n-grams, where the vertices may be associated with each other via edges that indicate different relationships between the vertices or the documents with which they are associated. A first word from one document may be associated with a second word from a different document via an edge that categorizes the relationship between the first word and the second word. In some embodiments, the category may indicate a relationship based on the set of domain vectors associating a first word and a second word. For example, the category may reflect that a first word is a subcategory of a second word, is associated with an expertise level greater than the second word, and is also part of a disambiguation group with the second word. By updating an ontology graph with a set of domain vectors and using the ontology graph as an index to retrieve documents, some embodiments may increase the speed of document retrieval and increase the relevance of retrieved information by providing knowledge within the scope of a user's indicated expertise.

In some embodiments, an ontology data model or knowledge graph organized by the ontology data model may improve the relevance of retrieved documents by accounting for a user's domain expertise or specific interests. Such operations may be especially useful in specialized applications where similar concepts may be disclosed in documents at differing levels of domain expertise, differing levels of security classification, or with differing amounts of relevance to subdomains. For example, if a user associated with a first hierarchical expertise level performs a search, some embodiments may obtain a first document associated with the first hierarchical expertise level and a second document associated with a second hierarchical expertise level. Some embodiments may then provide a user with the document associated with the first hierarchical expertise level. Additionally, by encoding relative levels of domain expertise or other domain-specific relationships in graph edges that indicate cross-domain relations, some embodiments may improve the speed and accuracy of responses to queries for information or provide other aspects of expert guidance. It should be emphasized, though, that not all embodiments necessarily provide these advantages, as there are several independently useful ideas described herein, and some implementations may only apply a subset of these techniques. As used in this disclosure, the term "ontology" may be used interchangeably with the term "ontology graph," unless otherwise indicated, where an entry of an ontology may include a vertex of the ontology.

FIG. 1 is a schematic diagram of a first computing environment in which a score stored in an account may be updated, in accordance with some embodiments of the present technique. In some embodiments, a computing environment 100 may be configured to mitigate some of the above-described problems, such as challenges associated with retrieving documents based on queries. The computing environment 100 may include a network 150 in communication with a computer system 110 that receive messages such as web requests or responses from a client computing device 104. As further discussed below, the client computing device 104 may include kiosk terminals, virtual reality headsets, mobile computing devices, laptops, desktop computers, tablet computers, or the like.

The client computing device 104 may be in a data session with the computer system 110 via the network 150, which allows the computer system 110 to access data stored in a database(s) 132. The database(s) 132 may include or otherwise be capable of accessing data stored in a document database 134, an account database 136, or an ontology database 138. As used in this disclosure, a database may refer to various types of data structures, such as a relational database or a non-relational database. The computer system 110 may include servers stored in a centralized location, a cloud server system, a distributed computing platform using different components or services, or the like. As further described in this disclosure, records may include links to associated records with respect to each other. In some embodiments, each of the databases may include data obtained from messages provided by external computer systems, such data indicating a pre-generated ontology graph. In some embodiments, databases may persist program state to a media that can retain information even in the event that power is lost. Alternatively, or in addition, a database need not be persistent and can include in-memory databases, which can include non-persistent program state.

In some embodiments, the computer system 110 may use ontology data obtained from the ontology database 138 to retrieve a set of documents from the document database 134 in response to a query provided by the client computing device 104. Some embodiments may retrieve the set of documents based on keywords, n-grams, word vectors, or the like. In addition to data encoded in the query, some embodiments may use data from the account database 136 to retrieve documents and sort the set of retrieved documents. Furthermore, as described elsewhere in this disclosure, the ontology data stored in the ontology database 138 may have been obtained by the computer system 110 via the client computing device 104 or another data source, such as a centralized computing server, a cloud server, or the like.

Some embodiments may store records of accounts, documents, ontology data, or other data in a non-relational or distributed database such as Apache Cassandra™, MongoDB™, or the like. For example, some embodiments may store data in the document database 134 in the form of a Hadoop database. Alternatively, or in addition, some embodiments may store data in a set of relational databases such as PostgreSQL™, Oracle mySQL™, or the like.

Some embodiments may store an ontology graph or other graph data in a data structure exhibiting index-free adjacency, such as a labeled property graph or a resource description framework (RDF) model. For example, some embodiments may store an ontology graph in a graph database model such as one used by Blazegraph, Janus graph, or Neo4j. In some embodiments, using an implementation of an RDF graph model may include adding a node to a graph portion template to include additional information associated with the graph portion template. For example, some embodiments may update a first graph portion template to indicate that a count of occurrences of the first graph portion template is now equal to 193 by adding or otherwise updating a node of the first graph portion template in the Neo4j graph model to store the value "193" in a node titled "occurrenceCount." In some embodiments, the data is stored in a graph database maintains index free adjacency to facilitate relatively fast interrogation of the data structure, for instance without imposing a relatively large overhead from maintaining indexes, though embodiments are also consistent with use of other data repositories, like relational databases, again which is not to suggest that other descriptions are limiting.

As described above, various types of graph databases may be used, such as Neo4j, DEX, Infinite Graph, or others described by Rawat et al. (Rawat, D. S. and Kashyap, N. K., 2017. Graph database: a complete GDBMS survey. Int. J, 3, pp. 217-226). In some embodiments, other implementations of a graph database may be used such as a Janus Graph™, Nebula Graph™, or the like. For example, some embodiments may build a model of a graph portion template by applying a script to convert the graph portion template into a Nebula Graph model, where the script may provide generate a query in the form of a graph-specific query language such as nGQL. As discussed elsewhere in this disclosure, some embodiments may query the graph model using a graph-specific query language such as nGQL or Cypher™.

For example, some embodiments may store ontology data in a set of SQL tables of the ontology database 138, where each record of the SQL table may represent a vertex record and include, as table fields, parent vertex identifiers, child vertex identifiers, categories indicating relationship types between vertices, scores associated with the relationship category, or the like. Some embodiments may store data in a combination of relational and non-relational databases. For example, some embodiments may store documents in a non-relational database and ontology data in a relational database. In some embodiments, a record of a relational or non-relational database may store a pointer, map, or other value usable for indicating relationships between a document record, ontology data record, an account record, or other data.

As further discussed in this disclosure, some embodiments may perform operations to retrieve documents based on a query sent to the computer system 110, where the documents may be selected based on one or more domain indicators associated with the query. In some embodiments, the domain indicator may be provided with a query or determined from the query. Alternatively, or in addition, the domain indicator may be retrieved from a user account stored in an account database 136 or otherwise determined from context parameters associated with a data session. Reference to "a record" followed by a reference to "the record" is consistent with scenarios where the record has changed in some regard between when the item is referenced, i.e., use of the indefinite article followed by the definite article should not be read to suggest that the thing referenced is immutable. Similar principles of construction should be applied to other mutable entities, such as a user account, an ontology or ontology data (e.g., a knowledge graph organized by the ontology data model), or the like.

As discussed above, some embodiments may use inputs provided by a user to perform semantic searches. In some embodiments, using one or more of the operations described in this disclosure may provide search results that match or exceeds other language models in general language tasks. For example, some embodiments may achieve 85-95% precision when tested using the SQUAD 1.1 dataset or Quora duplicate questions dataset. Some embodiments may surpass other language models when used to perform searches in domain-specific tasks. For example, some embodiments may achieve a 10 to 100% improvement in question-answer retrieval precision in a role-specific domain based on the role's association with specific classes of information associated with domain-specific knowledge. Some embodiments may include domain-specific operations or terminology, relationships, or contexts that may be relevant in only one domain or a small number of domains. For example, some embodiments may relate the terms of a drug and an internal product code to each other and categorize them as being associated with a shared concept (e.g., a same anticoagulant name), even if other AI systems or NLP systems do not include these terms. As used in this disclosure, a concept may be represented by a first vertex, a label or another type of category value, or the like. A concept may be or otherwise include a domain category value, where the subdomain represented by a concept may include the vertices associated with the first vertex via a set of graph edges.

Figure 2:
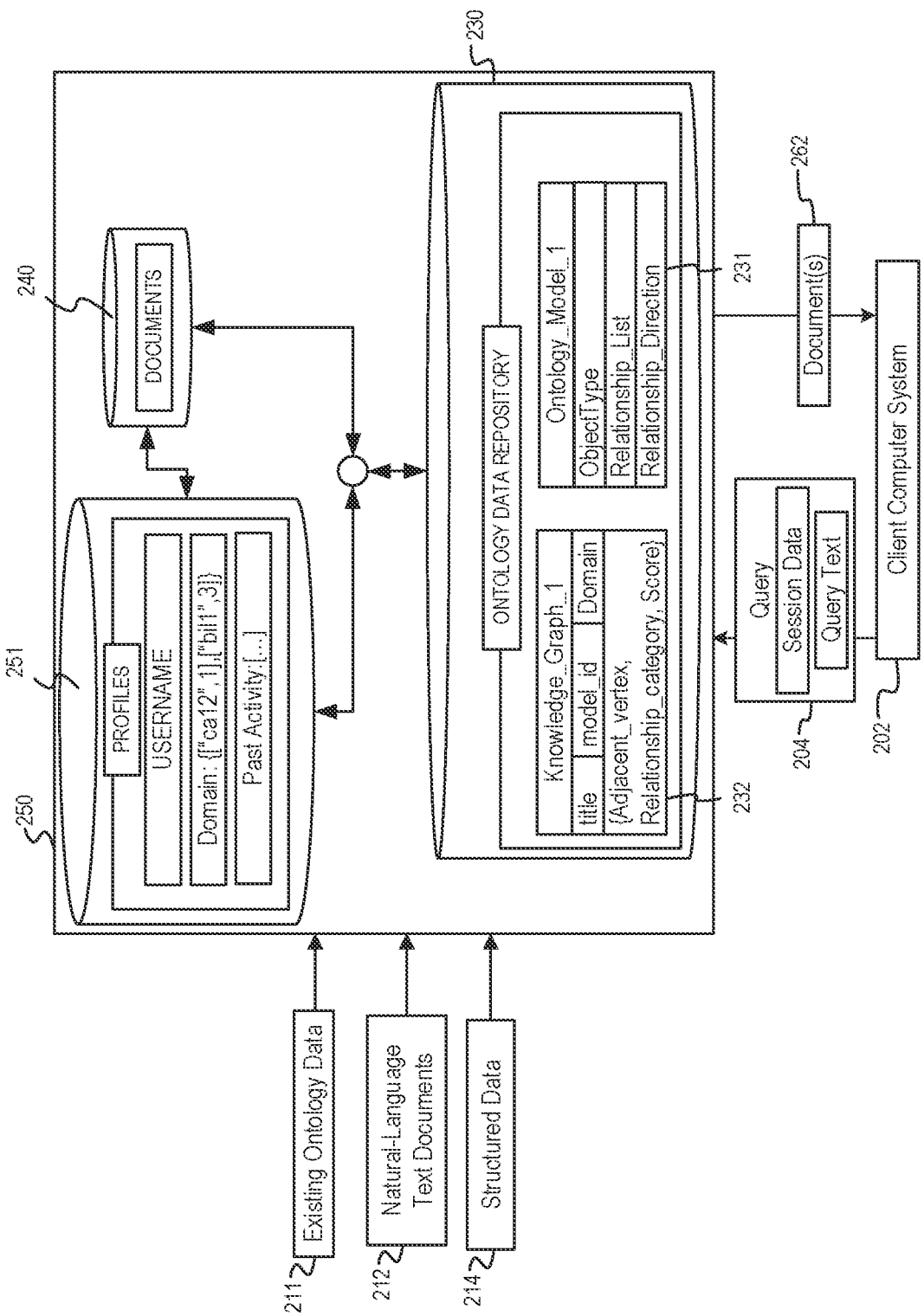
FIG. 2 depicts a logical and physical architecture of data stored in an ontology model, in accordance with some embodiments of the present techniques.

FIG. 2 depicts a logical and physical architecture of data stored in an ontology model, in accordance with some embodiments of the present techniques. In some cases, some or all of the techniques described in this disclosure may be implemented in the logical and physical architecture 200. The client computing device 202 may send a query 204 to a computer system 250. Data sent in the query 204 from the client computing device 202 may include query text or terms used to retrieve documents. In some embodiments, the query 204 may include or otherwise be associated with session data, such as an account identifier, a username, an indicated set of domain indicators, a feature associated with a user, or the like. In some embodiments, the session data may be provided as a list of context parameters, a vector of values, or the like. As further discussed below, some embodiments may expand a query based on an ontology graph to increase the effectiveness of a semantic search.

In some embodiments, the query, or a response to the query, may be sent in form of a web message or a set of web messages. A "web message" is an application-layer communication over a network to or from a web browser (which may include a webview object in a native application, a headless browser, or a browser extension). Web messages are not limited to rendered content or user inputs, and web messages may be encoded in hypertext transport language protocol (HTTP, like HTTP2) or according to other application-layer protocols. A "web message" (expressed as singular) can include one or more transmissions, in some cases with intervening responsive messages, like acknowledgments or API responses.

Some embodiments may use various types of data to generate or otherwise update the ontology data stored in the ontology data repository 230. The data may include a set of existing ontology data 211, a set of natural-language text documents 212, or a set of structured data 214. For example, the set of existing ontology data 210 may include an existing knowledge graph structured in an existing ontology data model, such as the unified medical language system (UMLS) metathesaurus (MeSH). The existing knowledge graph may be stored in various ways, such as in a relational data structure, and may be imported into the ontology data repository 230. As further discussed in this disclosure, different data types may be combined to update an ontology data model, such as one stored in an ontology data model record 231. The ontology data model record may store values for record fields such as object categories, relationships between the categories, directional indicators of the relationships, or the like. Alternatively, or in addition, the ontology data model may be stored in a knowledge graph such as a knowledge graph 232, which may be formatted in a specified ontology data model. For example, the knowledge graph 232 may be stored as a set of records indicating that the knowledge graph is structured in a data model specified by an ontology data model record 231.

Some embodiments may store documents from the set of natural-language text documents 212 or set of structured data 214 into the documents repository 240. The set of natural-language text documents 212 may be obtained from various types of sources, such as an application program interface (API) of a government server, an online textbook, a webpage, text stored in another database, or the like. For example, the documents repository 240 may include medical text from a textbook, legal text from healthcare law databases, internal medical record notes specific to a patient, or the like. As further discussed elsewhere in this disclosure, the documents of the documents repository 240 may be indexed by or otherwise accessed via data stored in the ontology data repository 230. For example, a pointer to a document stored in the documents repository 240 may be stored in a vertex record of a knowledge graph stored in the ontology data repository 230.

Some embodiments may store user account data in an account repository 251, such as an account name, domain information, past activity, or the like. For example, the account repository 251 may include a set of user records, each of which includes a username of an account and a set of domain indicators (e.g., categories, quantitative values, Boolean values, arrays, or the like) associated with the user. The set of domain categories may indicate roles or knowledge domains of the user, such as "doctor," "cardiologist," "IT architecture," or the like. In some embodiments, the knowledge domains may be associated with a category or other value indicating an expertise score. For example, a first user account record may include a knowledge category "cardiology" and an expertise score "2" and a second user account record may include a knowledge category "cardiology" and an expertise score "5." As discussed elsewhere in this disclosure, a categorical or quantitative score associated with a domain, such as an expertise score, may change which documents are presented to the client computing device 202 from the documents repository 240.

The processes presented in this disclosure are intended to be illustrative and non-limiting. In some embodiments, for example, the methods may be accomplished with one or more additional operations not described or without one or more of the operations discussed. Additionally, the order in which the processing operations of the methods are illustrated (and described below) is not intended to be limiting. In some embodiments, the methods may be implemented in one or more processing devices (e.g., a digital processor, an analog processor, a digital circuit designed to process information, an analog circuit designed to process information, a state machine, or other mechanisms for electronically processing information). The processing devices may include one or more devices executing some or all of the operations of the methods in response to instructions stored electronically on an electronic storage medium. The processing devices may include one or more devices configured through hardware, firmware, or software to be specifically designed for execution of one or more of the operations of the methods.

Figure 3:
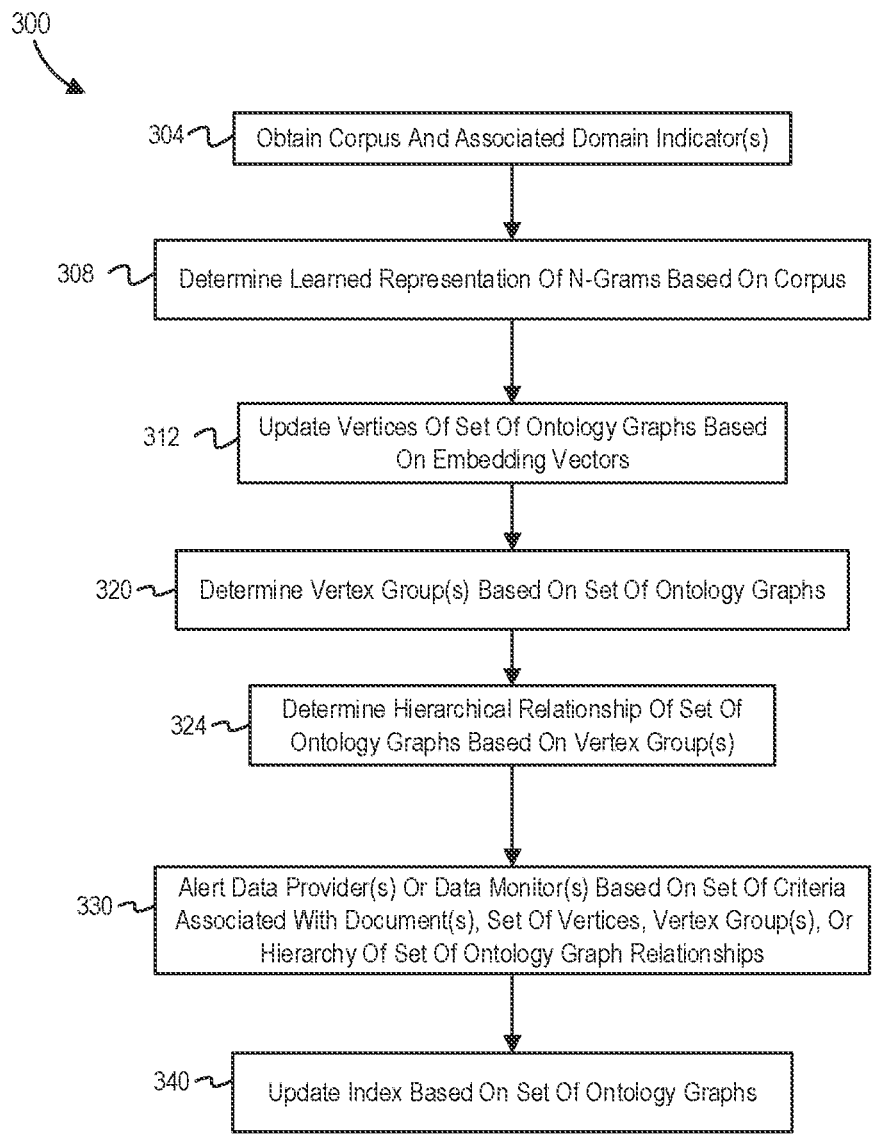
FIG. 3 is a flowchart of an example of a process by which natural language data may be converted in a set of ontology graphs, in accordance with some embodiments of the present techniques.

FIG. 3 is a flowchart of an example of a process by which natural language data may be converted in a set of ontology graphs, in accordance with some embodiments of the present techniques. Operations of the process 300 may begin at block 304. In some embodiments, the process 300 may include obtaining a corpus of text and an associated set of domain indicators, as indicated by block 304. The corpus of text may include documents from various sources, where the text in the documents may be organized as a single text block or be separated into multiple sections of the document. Documents in the corpus may be separated into n-grams, where an n-gram may include a sequence of n items from text, where "n" represents an integer, and where the items may include phonemes, syllables, letters, words, symbols, base pairs, or the like. Different models may use different items as the base element for an n-gram. Additionally, a first n-gram does not need to include the same number of items as a second n-gram. For example, a first n-gram of a first ontology graph vertex may be the word "verifying" and may be mapped to a second n-gram of a second ontology graph vertex, where the second n-gram may be the phrase "determining if a condition has been satisfied."

The corpus of text may be obtained from a variety of sources such as sources available via the Internet, sources available via an internal database or other data repository, information inputted into or otherwise provided via a UI element. For example, the corpus of text may be obtained from a medical textbook, a financial statement, an online database of medical information, a contract, a set of government regulations, or the like. In many cases, the corpus of text may include unstructured natural-language text documents such as a textbook chapter or science paper, which may be contrasted with structured language text documents such as a table of values, an enumerated list of values, or the like. Some embodiments may use data source profiles to determine or otherwise update a set of domain indicators associated with a document obtained from the corresponding data source. For example, if a subset of documents of a corpus is obtained from a company's data repository, some embodiments may retrieve a data source profile of the company and associate previously-entered metadata stored in the data source profile with the subset of documents. In some embodiments, the corpus may include unstructured natural-language text, such as passages of text, video transcripts, or the like. Some embodiments may pre-process video or audio to transform the same into text, for instance with speech-to-text algorithms or scene description algorithms.

Various operations may be performed when obtaining a corpus for use as part of a structured knowledge base that is usable as part of a knowledge fabric, which is further described below. In some embodiments, the corpus may include data generated from media files, such as metadata associated with images, object recognition of videos, or the like. The corpus may include data obtained from an API of a database service (e.g., DropBox, Google Drive, Veeva Vault, DXC, Microsoft Dynamics, etc.). Some embodiments may inspect data being provided to the corpus to verify that the information encoded in the data is secure or accurate. For example, some embodiments may determine that data being added to a corpus includes a set of expected values or terms or determine that messages received from an API satisfies one or more web filters. Some embodiments may further ingest and distinguish between publicly available data (e.g., data obtained by an organization from a data source that is not controlled by the organization) and private data. For example, some embodiments may ingest publicly available data from a government entity and ingest private data stored as free text customer feedback.

Some embodiments may obtain a set of domain indicators associated with the corpus of text. Each document in a corpus of text or a subset of documents in the corpus of text may store or otherwise be associated with a set of metadata tags indicating a domain of the document. For example, each respective document in a corpus of text may be store a first respective domain indicator representing a domain category selected from a set of categories (e.g., "[cardiology, gastroenterology, gastronomy]") and a second respective domain indicator indicating an expertise score for the corresponding domain category (e.g., a numeric value ranging between zero and ten). Various types of domains may be indicated, such as a specific document topic, a field of study discussed in the document, a target audience for the document, a user role having permission to read the document, or the like. In some embodiments, documents may be associated with categorical values or numerical values indicating a complexity or target expertise of a document. For example, some embodiments may obtain a document that is associated with a vector "[1, 5]," where the first element "1" of the vector may indicate a specific domain, and the second element "5" of the vector may indicate an expertise score (e.g., "class"). Alternatively, or in addition, some embodiments may generate the vector or other list of values may be used to indicate expertise for a variety of domains or derived domain categories. For example, a list of values may include "[0, 5, 0, 0, 20]," where each number of the list may represent a class for one of the five different fields of domain knowledge. As further discussed below, some embodiments may use an indicated expertise score or other score associated with a domain to determine a hierarchy or other order between different ontologies or knowledge graphs. A set of ontology graphs organized in a hierarchy may be used as part of an index for a knowledge fabric, which may include a set of documents or other data, the ontology system(s) and indices used to organize the set of documents or other data, or the functions used use the ontology system(s) or indices used to retrieve information from the set of documents or other data. By using a knowledge fabric that is organized by a set of ontology graphs, some embodiments may quickly navigate through different knowledge domains or different classes within those domains to retrieve relevant queries for a specific user.

The process 300 may include determining a learned representation of n-grams based on the obtained corpus, as indicated by block 308. A learned representation may include various value types, such as categories, Boolean values, quantitative values, or the like. In some embodiments, a learned representation may include a set of embedding vectors in a multi-sense embedding space. Some embodiments may determine a learned representation for each n-gram in a document, where the learned representation may include an embedding vector, where the embedding vector may include a set of values in an embedding space that indicate a position in the embedding space. Some embodiments may determine the embedding space by using a statistical method or machine-learning method. Some embodiments may determine an embedding vector in a multi-sense embedding space for an n-gram, where a multi-sense embedding space may allow the same n-gram to correspond with different factors in an embedding space. For example, the n-gram may be a first word "run" in a document and may correspond with two different embedding vectors in a multi-sense embedding space based on words around the first word in the document.

As described elsewhere in this disclosure, some embodiments may perform one or more machine-learning operations to determine a set of embedding vectors in an embedding space. The embedding space of a word vector may include a large number of vector dimensions, such as more than 10 dimensions, more than 100 dimensions, more than 1000 dimensions, or the like. In some embodiments, the embedding space used to represent an n-gram may have fewer dimensions than a cardinality of the n-grams. For example, a corpus may include over one million n-grams, over ten million n-grams, over one hundred million n-grams, or the like. Some embodiments may represent n-grams of such a corpus with less than one hundred thousand dimensions, less than twenty thousand dimensions, less than ten thousand dimensions, or less than one thousand dimensions, or the like.

As described elsewhere in this disclosure, some embodiments may also determine relationships between learned representations using a machine learning operation. For example, some embodiments may use a trained neural network to determine relationships between different n-grams or other values represented by ontology vertices based on first set of n-grams represented by the ontology vertices and another set of n-grams surrounding the first set of n-grams. In some embodiments, the relationships between different concepts, ontology vertices, or other elements of an ontology may be encoded as ontological triple. An ontological triple may include a first value identifying a first vertex, a second value identifying a second vertex, and a third value that categorizes or quantifies a relationship between the first vertex and the second vertex. For example, some embodiments may determine that a first vertex representing the document-obtained n-gram "smartphone" has a categorical relationship of "subset" with respect to a second vertex representing the document-obtained n-gram "computing device." In some embodiments, this relationship may be determined based on a sequence of document-obtained n-grams, such as the phrase "is a type of."

Some embodiments may generate a set of embedding vectors using a neural network model that determines an embedding vector for a first n-gram without using data based on the n-grams around the first n-gram, such as a continuous-bag-of-words (CBOW) model, Skip-gram model, or other model described in Bhoir et al. (Bhoir, S., Ghorpade, T. and Mane, V., 2017, December. Comparative analysis of different word embedding models. In 2017 International Conference on Advances in Computing, Communication and Control (ICAC3) (pp. 1-4). IEEE), which is hereby incorporated by reference. For example, some embodiments may perform a shallow neural network model, such as a Word2Vec model (which may use either of or both the CBOW model and the Skip-gram model) to determine embedding vectors for words or other n-grams of a document.

Alternatively, or in addition, context-independent embedding operations other than neural-network-based operations may be used, such as a matrix factorization method. For example, some embodiments may use a Global Vector ("GloVe") model to determine an embedding vector for an n-gram, where using a GloVe model may include using a matrix model trained a global word to word co-occurrence count, and where the GloVe model may be further described by Pennington et al. (Pennington, J., Socher, R. and Manning, C. D., 2014, October. Glove: Global vectors for word representation. In Proceedings of the 2014 conference on empirical methods in natural language processing (EMNLP) (pp. 1532-1543)), which is incorporated herein by reference.

Some embodiments may use objects other than words as n-grams, such as sub-words or groups of words. For example, some embodiments may use a model that splits a word such as "apple" into the tri-gram "app," "ppl," and "ple," where the word embedding vector for apple will be the sum of the n-grams. Various neural network models may be used to determine embedding vectors for multiple n-grams generated from one word, such as a FastText model or another shallow neural network model (i.e., a neural network having fewer than four hidden neural network layers). For example, some embodiments may use a shallow neural network model to determine embedding vectors for the word "cardiomyopathy" by splitting the word into the n-grams "cardio," "myo," and "opathy," determining an intermediate vector for each individual n-gram, and determining an embedding vector based on the three intermediate vectors.

Some embodiments may determine an embedding vector associated with an n-gram using a model based on both the n-gram itself and the context surrounding the n-gram (e.g., other n-grams, syntax, semantics). For example, some embodiments may use neural networks models trained on a set of text of a corpus or other training data to predict n-grams based on other n-grams in a system via a set of attention values for the n-grams, where the attention values may be used to weigh or otherwise modify an output of a neural network. Various models may use different types of neural network models, perform different pre-processing operations, use different operations to determine attention values, or the like. For example, some embodiments may use bidirectional long short term memory (LSTM) neural networks or another recurrent neural network to generate encoding vectors, such neural networks described in Embeddings from Language Models (ELMo), as described by Peters et al. (Peters, M. E., Neumann, M., Iyyer, M., Gardner, M., Clark, C., Lee, K. and Zettlemoyer, L., 1802. Deep contextualized word representations. arXiv 2018. arXiv preprint arXiv:1802.05365), which is hereby incorporated by reference. By determining embedding vectors or other learned representations of words or other n-grams based on their surrounding words or n-grams, some embodiments may account for word or phrase disambiguations.

Various methods may be used to determine attention values and use the attention values. For example, some embodiments may use a multi-headed attention-based autoencoder trained to use attention values mapped to n-grams determined with attention heads, such as autoencoders using a model similar to those described by Vaswani et al. (Vaswani, Ashish, Noam Shazeer, Niki Parmar, Jakob Uszkoreit, Llion Jones, Aidan N. Gomez, Lukasz Kaiser, and Illia Polosukhin. "Attention is all you need." In Advances in neural information processing systems, pp. 5998-6008. 2017, arXiv:1706.03762) or Devlin et al. (Devlin, J., Chang, M. W., Lee, K. and Toutanova, K., 2018. Bert: Pre-training of deep bidirectional transformers for language understanding. arXiv preprint arXiv:1810.04805), which are incorporated herein by reference. Such embodiments may use a multi-headed attention model, where an attention head of the multi-headed attention model may determine a set of query/key/value weight matrices for each attention head during training. In some embodiments, Q, K, and V may be determined as projection vectors. For example, Q may represent a query vector indicating an n-gram position(s) in a sequence of n-grams and K or V may represent a key vector indicating all the n-gram positions in a sequence of n-grams. This plurality of weight matrices may then be used to determine a plurality of attention matrices, where each element of the attention matrices may represent a respective attention value of a respective n-gram of a set of n-grams. The attention matrices may then be concatenated and multiplied by a weights matrix based to determine an output set of attention values. Some embodiments may determine an output set of attention values for each set of n-grams of a document to determine attention values for the document. Additionally, some embodiments may include a position vector or other set of position values to indicate the positions of n-grams in a sequence of n-grams relative to other n-grams of the sequence of n-grams. In some embodiments, a position vector may follow a specified pattern based on the respective position of the respective n-gram relative to other n-grams from the same document, such as n-grams that are in the same sentence as the respective n-gram or the same paragraph as the respective n-gram. For example, each respective position value of a position vector for a respective n-gram of a sequence of n-grams may be monotonically increased with respect to its position amongst the other n-grams of the sequence of n-grams.

Some embodiments may compute positive features to determine attention values used to determine an embedding vector. For example, some embodiments may use a model described by Choromanski et al. (Choromanski, K., Likhosherstov, V., Dohan, D., Song, X., Gane, A., Sarlos, T., Hawkins, P., Davis, J., Mohiuddin, A., Kaiser, L. and Belanger, D., 2020. Rethinking Attention with Performers. arXiv preprint arXiv:2009.14794), which is herein incorporated by reference. Some embodiments may generate a pair of random feature maps using a feature map function $\phi$. Various types of the feature map functions may be used. For example, some embodiments may use the form shown below in Equation 1, where h(x) may be a function of an input x, such as the input value itself, where m and l represent dimension size, the functions $f_1$ to $f_l$ or $f_m$ may include one or more real functions (e.g., a sin function, cosine function, or the like), and $\omega_1$ and $\omega_1$ to $\omega_m$ may represent a set of deterministic vectors obtained from a probability distribution, and where the superscript T may indicate a transpose operation:

$$\phi = \frac{h(x)}{\sqrt{m}}(f_1(\omega_1^T x), \ldots, f_1(\omega_m^T x), \ldots f_l(\omega_1^T x), \ldots, f_l(\omega_m^T x)) \quad (1)$$

Some embodiments may reduce the variance of an estimated value, such as an approximated key vector or an approximated query vector, by entangling random samples that are orthogonal by using a Gram-Schmidt renormalization process. Some embodiments may generate a random feature map $\phi(x)$ based on an input vector x, a second random feature map $\phi(y)$ based on the input vector y, and determine an approximated key matrix based on the inner product of first and second random feature maps (i.e. "$\phi(x)^T\phi(y)$"), such as an approximated key matrix equal to the exponential of the inner product (i.e. "$E[(x)^T\phi(y)]$"). Some embodiments may determine a set of attention values by determining an approximated query vector Q' equal to $\phi(Q)$, an approximated value vector K' equal to $\phi(K)$, and determine a set of attention values based on the approximated key matrix, and where Q and K may be original query and key vectors determined as projection vectors based on the input sequence of n-grams. For example, some embodiments may determine the set of attention values for a sequence of n-grams of a document described in this disclosure using implementations of Equation 2 and 3, where $\widehat{Att}$ may represent the set of approximated attention values, V represents a value vector, $\hat{D}$ may represent an approximated diagonal function, and $1_L$ may represent an identity matrix of size L, where L may indicate a size of the sequence of n-grams:

$$\widehat{Att} = \hat{D}^{-1}(Q'(K')^T V) \quad (2)$$

$$\hat{D} = \text{diag}(Q'((K')^T 1_L) \quad (3)$$

The process 300 may include updating vertices of a set of ontology graphs based on the set of embedding vectors, as indicated by block 312. As described elsewhere in this disclosure, some embodiments may store or otherwise access ontology data such as knowledge graphs written in an ontology data model or the structure of the ontology data model itself. As used in this disclosure, the term ontology graph may refer to either or both an ontology data model and a knowledge graph stored in the format of the ontology data model. As used in this disclosure, a vertex of an ontology graph may be associated with a learned representation by having the learned representation as an identifier, a hash value of the learned representation as an identifier, storing the learned representation or hash value of the learned representation in a related record, or the like. A vertex of a graph may be stored as a single record of a database, a set of different records or fields of the record, or the like. For example, a vertex associated with a learned representation of an n-gram may include a first record stored in a first database and a second record stored in a second database. The first record may include a graph identifier of the first vertex and an identifier to the second record, and the second record may include the learned representation of the n-gram.

As discussed elsewhere in this disclosure, some embodiments may obtain a set of ontology graphs from an initial source or generate the ontology graph from a set of initial data. For example, some embodiments may obtain a set of ontology graphs, including a graph representing an ontology data model and a knowledge graph formatted in the ontology data model from a medical repository, government repository, commercial repository, or the like. Some embodiments may update a knowledge graph formatted in the form of an ontology data model or another ontology graph based on the set of embedding vectors determined using one or more operations described in this disclosure. For example, a knowledge graph may include a vertex identified or otherwise associated with a first embedding vector, where a vertex may correspond with an embedding vector or other learned representation if the learned representation is an identifier of the vertex or is stored in a record of the vertex.

Some embodiments may update a vertex or data associated with the vertex based on the set of embedding vectors by updating a set of stored pointers to documents to indicate a document storing the n-gram, updating a count of the number of n-grams being used, or the like. For example, an embodiment may determine that the n-gram "blue" is used in a first document based on the set of n-grams determined using one or more operations described in this disclosure. In response, the embodiment may store a pointer to the first document and a count of the times the n-gram is used in the first document. Some embodiments may use this information to rank or otherwise select one or more documents from a corpus based on a query.

Some embodiments may generate or update a plurality of ontology graphs based on the set of learned representations. Additionally, some embodiments may obtain a plurality of initial ontology graphs and update each of the initial plurality graphs as new data is received or analyzed. For example, some embodiments may obtain a first ontology graph storing embedding vectors representing aeronautical engineering concepts and a second ontology graph storing embedding vectors representing airplane pilot concepts. Some embodiments may then obtain a corpus of text and independently update each of the ontology graphs with additional vertices based on the embedding vectors of n-grams of the documents of the corpus using one or more operations described above. In some embodiments, relationship types between already-encountered learned representations and newly learned representations may be also be learned or interpreted using a machine learning method or statistical method. For example, a neural network may be trained to determine that a first learned representation is a conceptual subset of a second learned representation based on the detection of a phrase "is a type of" or "is one of." Alternatively, or in addition, some embodiments may include operations to use structured data, such as tabular data, to determine associations between vertices. For example, a row of an imported data table may indicate that a first n-gram may be equivalent to a second n-gram, and this indication may be used to generate an association between a first vertex corresponding to the first n-gram and a second vertex corresponding to the second n-gram.

The process 300 may include determining a set of vertex groups based on the set of ontology graphs, as indicated by block 320. A vertex group may include a set of multiple vertices or an aggregation of the multiple vertices of an ontology graph and may be categorized or otherwise classified based on the types and methods used to group its vertices. A vertex group may include vertices representing derived values computed from learned representations. For example, a vertex group may include a vertex representing a centroid of the vectors. In addition, some embodiments may determine other values derived from a group of vertices, such as a set of values or functions representing a boundary of the vectors surrounding vertices of the vertex group.

Some embodiments may use an unsupervised learning operation to map one or more concepts represented by vertex groups to n-grams. For example, some embodiments may determine a vertex group using a clustering method, such as a K-means clustering method or a hierarchical clustering method, to determine a vector cluster. Each respective vector of the vector cluster corresponds with a respective vertex of the vertex group. Vertices of a vertex group may be described as being of the same cluster if their corresponding vectors are assigned to the same cluster during a clustering operation. For example, some embodiments may use a K-means clustering method after determining an initial set of centroids of vectors in a multi-sense embedding space. Some embodiments may determine the initial set of centroids based on an initial knowledge graph, determine a set of neighboring vertices of the centroid based on a set of pairwise distances between the set of neighboring vertices and the centroid in the embedding space, and re-compute each of the respective centroids based on the set of neighboring vertices. The use of the K-means clustering method may provide a fast way of determining groups of vertices and their associated n-grams.

Some embodiments may determine a vertex group using a density-based clustering method, such as using an implementation of a density-based spatial clustering of applications with noise (DBSCAN) algorithm. For example, some embodiments may use DBSCAN algorithm implementation that finds the neighboring vectors of a first embedding vector assigned to a first cluster. Using the DBSCAN algorithm implementation may also include finding the vectors within a threshold distance of the core vector and assign the vectors to the first cluster or otherwise associate the vectors with the first cluster. For example, some embodiments may determine that a plurality of pairwise distances between a first vector and a plurality of other vectors is less than a distance threshold, where the vectors may be in a multi-sense embedding space described in this disclosure, and where the plurality of pairwise distances may be in the same multi-sense embedding space. Some embodiments may then check that a count of the plurality of the other vectors satisfies a minimum vectors threshold, such as at least two other vectors, at least five other vectors, or the like. Some embodiments may then associate each respective vector of the plurality of other vectors with the vector cluster. Some embodiments may then iteratively perform these steps until no further assignments or re-assignments to a cluster occurs. In some embodiments, a determination that a pair of vector are part of a same cluster may indicate a degree of semantic similarity between the n-grams represented by the pair of vectors, where a lesser distance may be correlated with an increased degree of semantic similarity.

Some embodiments may categorize a vertex group determined from a clustering method as a first type of vertex group, where vertices of a vertex group of the first type of vertex group may be associated with vectors categorized as being part of a same cluster. In some embodiments, the vertex group may represent a 'concept' in a domain, where the concept may be shared amongst multiple classes of the domain. Alternatively, or in addition, the vertex group may represent a 'concept' for a specific class of the domain. As described elsewhere in this disclosure, one or more n-grams may be mapped to a plurality of different vectors, two or more of which may be mapped to different clusters. For example, a first n-gram may be mapped to a first vector and a second vector, where the first vector may be part of a first cluster representing a first concept and where the second vector may be part of a second cluster representing a second concept.

Some embodiments may update a knowledge graph based on a vertex group determined using a clustering operation. For example, some embodiments may determine that an embedding vector is closest to a centroid of a cluster of vectors in a multi-sense embedding space and, in response, update the vertex of an ontology graph corresponding with the embedding vector to indicate that the embedding vector is near the centroid. Alternatively, or in addition, some embodiments may generate or update a vertex of an ontology graph based on the centroid of the cluster, where some embodiments may indicate that the vertex represents a derived set of values.

The process 300 may include determining a set of hierarchical relationships for the set of ontology graphs, as indicated by block 324. As described elsewhere in this disclosure, knowledge graphs or other ontology graphs may be organized in different domains or sub-domains. In some embodiments, a set of ontology graphs may be sorted into a hierarchy of ontology graphs based on domains associated with the vertices of the ontology graph and categories or quantitative values associated with the domains.

Some embodiments may determine a hierarchy of ontologies based on one or more vertex groups associated with a vector cluster via an edge connection between the vertex group and one or more shared connections. Some embodiments may determine that a first vertex group of a first ontology graph may be associated with a vertex of a second ontology graph via one or more shared vertices. For example, a first vertex group may include a set of vertices corresponding with a first set of learned representations that includes the embedding vector $[x_1, x_2, x_3]$. Some embodiments may determine that the embedding vector corresponds with a vertex in a second ontology graph, and, in response, determine that the first vertex group is associated with the vertex in the second ontology graph. Additionally, if the vertex in the second ontology graph is part of a second vertex group, some embodiments may determine that the first vertex group is associated with the second vertex group of the ontology graph.

Some embodiments may then determine a hierarchy between the first ontology graph and the second ontology graph based on a relationship between the first vertex group and the second vertex or second vertex group. For example, some embodiments may determine that a first vertex of a first ontology graph is associated with a first domain indicator representing a first expertise score, and that the first vertex is part of a first vertex group. The first ontology graph may be part of a set of ontology graphs that includes a second ontology graph, where the second ontology graph may include a second vertex. The second vertex may be associated with a second domain indicator representing a second expertise score. In response to a determination that the first vertex group is associated with the second vertex, some embodiments may then determine a hierarchy order between the first ontology graph and the second ontology graph based on the first domain indicator and the second domain indicator. For example, if the first vertex is associated with a domain expertise score of "1," indicating basic expertise, and if the second vertex is associated with a domain expertise score of "10," indicating extreme expertise, some embodiments may determine that the first ontology graph is lower on a domain hierarchy than the second ontology graph. Alternatively, or in addition, some embodiments may determine a hierarchy of concepts based on a shared n-gram between two cluster of vectors corresponding to two different concepts. For example, a first n-gram may be mapped to a first vector and a second vector, where the first vector may be part of a first cluster representing a first concept and where the second vector may be part of a second cluster representing a second concept.

Some embodiments may determine that the first and second cluster share an n-gram and, in response, determine a hierarchy between the two concepts based on the documents associated with the concepts. For example, a first and second ontology graph may be associated with the domain "medical billing," where documents associated with vertices of the first ontology graph may be associated with the class category "expert," and where documents associated with vertices of the second ontology graph may be associated with the class category "layman." Some embodiments may then associate the first ontology graph with the category "expert" and the second ontology graph with the category "layman" based on their associated class categories and update a hierarchy of the two ontology graphs such that the first ontology graph has a higher hierarchy value than the second ontology graph. In some embodiments, the classes or other categories used may be mutually exclusive with respect to each other. For example, an ontology graph labeled as "expert" may be forbidden from being labeled as "layman," where the ontology graph may be labeled with categories from a set of mutually exclusive categories such as, "layman," "beginner," "advanced," and "expert." Some embodiments may account for the user's goals, for instance, determining a hierarchy based on whether the user intends to engage in a higher-risk activity in which more certainty is warranted than in a lower-risk activity, or based on whether the user intends to explore new relationships between concepts or determine which are well established relationships.

In some embodiments, a first and second ontology graph may be associated with computed domain indicators, such as a computed expertise score. For example, vertices or other subgraph components of a first ontology graph may be associated with a first set of documents, and vertices or other subgraph components of a second ontology graph may be associated with a second set of documents. Some embodiments may determine a measure of central tendency of the first set of expertise scores of the first set of documents, such as a mean average of the first set of expertise scores and a measure of central tendency of the second set of expertise scores of the second set of documents, such as a mean average of the second set of expertise scores. Some embodiments may then determine a hierarchy between the first ontology graph and the second ontology graph based on the measures of central tendency.

The process 300 may include alerting data providers or data monitors based on a set of criteria associated with a set of documents, a set of vertices, a set of vertex groups, or the hierarchy of the set of ontology graph relationships, as indicated by block 330. Various alerts may be generated based on possible discrepancies or new domains determined from the set of ontology graphs or their associated documents. The alerts may indicate that a document should be associated with a different domain indicator, that a new domain may exist based on different users viewing a same set of documents, that a new ontology graph should be generated, or the like.

Some embodiments may determine a predicted domain indicator for a document using a prediction model, such as a neural network or a statistical method. Some embodiments may determine a vector representing expertise scores for one or more documents using a neural network trained to predict a document's complexity based on the n-grams of the document. For example, an encoder neural network may be used to predict a domain indicator such as a single domain category, an expertise score associated with the single domain category, a plurality of domain categories, a plurality of expertise scores corresponding with a plurality of domain categories, or the like. After obtaining a trained encoder neural network, some embodiments may then determine a predicted set of domain indicators for an obtained document and then determine whether the predicted set of domain indicators is different from the obtained set of domain indicators associated with the obtained document. In response to a determination that the predicted set of domain indicators differs from the obtained set of domain indicators, some embodiments send an alert to a client computing device or another computing device of a data-providing entity or a data-monitoring entity. Alternatively, or in addition, some embodiments may use a trained neural network to determine a predicted domain indicator in the form of a quantitative value and then determine whether the predicted domain indicator is within a threshold range of the corresponding obtained domain indicator associated with the obtained document. In response to a determination that the predicted domain indicator exceeds the threshold range of the obtained domain indicator, some embodiments may send an alert to a client computing device or another computing device of a data-providing entity or a data-monitoring entity. For example, some embodiments may sent an alert indicating a mismatch between a predicted set of domain indicators for a document and an obtained set of domain indicators for the document.

Some embodiments may determine that an n-gram is mapped to a plurality of concepts and, in response, send an alert to a data provider or data monitor requesting clarification or additional information. For example, some embodiments may determine that the n-gram "hemorrhage" is associated with both a first embedding vector and a second embedding vector. The first embedding vector may be a vector of a first cluster associated with a first concept in a medical domain, and the second embedding vector may be a vector of a second cluster associated with a second concept in a financial domain. Some embodiments may then select a data provider listed as an expert in at least one of the first medical domain or the financial domain based on an expert score associated with the data provider, where expertise may be associated with a specific set of categories or specific set of values. Alternatively, or in addition, expertise may be associated with having an expertise score that satisfies an expertise threshold. Some embodiments may then send an alert to the data provider categorized as an expert to request an input to characterize at least one of the first concept or the second concept. Some embodiments may characterize a concept by providing a text definition of the concept, determining the boundaries in an embedding space associated with the concept, determining the embedding vectors in embedding space associated with the concept, confirming that an association between the n-gram and the concept is valid, providing an alternative cluster or additional cluster for a concept, or the like.

Some embodiments may determine a first set of accounts associated with a first set of domain indicators and a second set of accounts associated with a second set of domain indicators, where users corresponding to both the first and second sets of accounts frequently access the same set of documents. In response, some embodiments may determine whether the first set of accounts and a second set of accounts share a subset of domain indicators between the first set of domain indicators and a second set of domain indicators. For example, a first set of users may be labeled or otherwise associated with a first vector in an account parameter space, and a second set of users may be labeled or otherwise associated with a second vector in the account parameter space. An account parameter space may include dimensions representing various values such as a domain parameter space, other account parameters, or other parameter values. For example, an account parameter space may include a set of domain indicators such as domain categories, quantitative values representing expertise scores in their respective domain categories, demographic information such as education statuses, system use information such as a history of previously-accessed articles, or the like. Some embodiments may generate an indicator of the proposed set of accounts, generate an alert that a possible new domain vector or other proposed new domain indicator has been detected, or directly generate the new domain vector as a proposed new domain indicator to be associated with one or more accounts.

The process 300 may include updating an index based on the set of ontology graphs, as indicated by block 340. As described elsewhere in this disclosure, a set of documents stored in a repository may be accessed via one or more pointers stored as a part of or otherwise associated with a vertex of an ontology graph. For example, a knowledge graph may include a set of vertices corresponding to embedding vectors. Each vertex may store or be associated with one or more documents or positions within the document using the n-gram associated with the vertex.

As described elsewhere in this disclosure, the knowledge graph or other ontology graph data determined using one or more of the operations of this disclosure may be used as an index, where updating the index may be performed by updating the ontology graph. Alternatively, or in addition, some embodiments may include an index that is independent of a knowledge graph and may cause the update of the index by updating the corresponding knowledge graph. For example, a first knowledge graph may include pointers to a first set of records of an index. In response to a detected update to the first knowledge graph causing the association of an additional document with a vertex of the knowledge graph, some embodiments may update the corresponding index to include an additional record pointing to the additional document.

Various types of indices may be constructed or updated based on to an ontology graph, such as an index having a self-balancing tree data structure ("B-tree index"), where a b-tree index may include a set of index nodes starting at root index node. A B-tree index may have an order value m, where each index node has at most m child index nodes, each non-leaf index node has at least m/2 index nodes, and a non-leaf index node having k child index nodes will contain a proportional number of keys for their child index nodes. An index node of a B-tree may include a key value and a pointer to another index node. In some embodiments, the key value of the index node may correspond to one of a pair of n-grams, where a child index node of the index node acting as a leaf index node may include a pointer to or other identifier of the other n-gram of the pair of n-grams. Alternatively, or in addition, some embodiments may store data other than a pointer or identifier in a leaf index node, such as a text summary or an entire document.

Some embodiments may store an association between a pair of concepts, pair of vertices, pair of n-grams, or pair of embedding vectors in an index. Some embodiments may also store a related categorization or quantification of the association, such as a difference between class values, in the index. For example, some embodiments may include or associate a difference associated with a graph edge between a first n-gram and a second n-gram that indicate class value difference of "1" between the first n-gram and the second n-gram. In some embodiments, the class value difference "1" may indicate that the first n-gram is associated with a class value that is greater than the class value of the second n-gram by "1." The value may be stored in various ways, such as directly in a leaf node of an index stored in a B-tree structure, in a record identified by an index node, or the like.

Some embodiments may increase the utility of the index by updating the index to include references between documents based on a hierarchy of ontology graphs. For example, some embodiments may index a first set of documents using a first set of index records based on a first ontology graph. The first set of graph-indexed documents may then be updated during or after a determination that the first ontology graph is greater on a hierarchy with respect to a second ontology graph, where the second ontology graph comprises a vertex associated with a second document that is not in the first set of graph-indexed documents. Some embodiments may then determine that the first set of documents has a greater domain indicator value than the second document based on the hierarchy of the ontology graph. Alternatively, the first set of graph-indexed documents may then be updated during or after a determination that the first ontology graph is lesser on a hierarchy with respect to the second ontology graph, where the second ontology graph comprises the vertex associated with the second document not in the first set of graph-indexed documents. Some embodiments may then determine that the first set of documents has a lesser domain indicator value than the second document based on the hierarchy of the ontology graph.

Additionally, the index may further be updated to indicate documents related to each other via vertex adjacency. For example, some embodiments may determine that a first vertex corresponding to a first learned representation of a first n-gram is associated with a second vertex corresponding to a second learned representation of a second n-gram, where the first vertex and second vertex vertices of different ontology graphs, and where the first vertex is associated with a first document, and where the second vertex is associated with a second document. Some embodiments may then determine that the second vertex is associated with a third vertex adjacent to the second vertex. Various operations may be performed to determine that two vertices of an ontology graph are adjacent. For example, some embodiments may determine that the adjacent vertex is associated with the second vertex based on a pre-existing edge associating the second vertex with the third vertex. Alternatively, or in addition, some embodiments may associate the second vertex with the third vertex by generating an edge between the two vertices in response to a determination that n-grams of a corpus associate the two corresponding n-grams of the two vertices. Alternatively, or in addition, the edge may be generated in response to a clustering operation such as one described elsewhere in this disclosure.

Based on the association between the first vertex with the second vertex and the second vertex with the third vertex as described above, some embodiments may generate an edge or other encoded association between the first vertex and the third vertex. In some embodiments, this third vertex may be associated with a third document not associated with the first vertex or the second vertex. In response to an association between the first vertex and the third vertex, some embodiments may correspondingly update a record of the first document in an index to include a pointer or other reference to the third document. In addition, some embodiments may update a hierarchical relationship between the first document and the third document, which may increase the speed of document retrieval. Various other associations in the index may be made, such as associating the first vertex with the second document or the third document. By associating documents of a corpus in an index based on hierarchical associations between vertices of knowledge graphs and vertex adjacency in a knowledge graph, some embodiments may increase the speed of document retrieval by using the index. Additionally, as further described below, some embodiments may generate question-answer pairs based on the knowledge graph and include the question-answer pairs in an index. For example, some embodiments may associate a specific query or type of query with a specific document or set of documents. Some embodiments may include this association representing a question-answer pair in the index.

Figure 4:
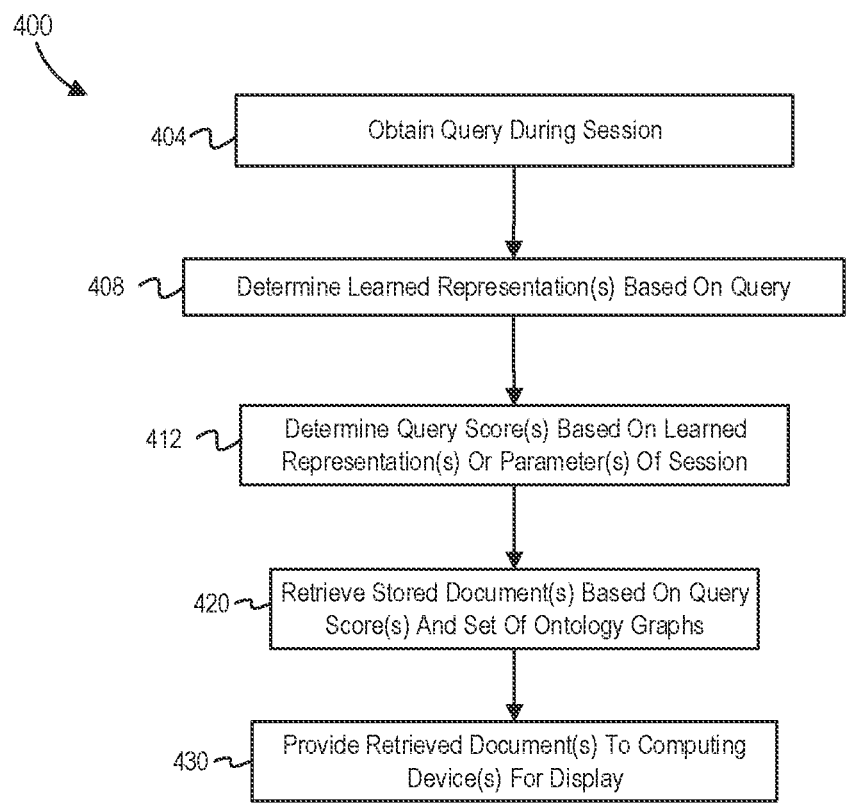
FIG. 4 is a flowchart of an example of a process by which a query may retrieve data based on a set of ontology graphs, in accordance with some embodiments of the present techniques.

FIG. 4 is a flowchart of an example of a process by which a query may retrieve data based on a set of ontology graphs, in accordance with some embodiments of the present techniques. The process 400 may include obtaining a query during a session, as indicated by block 404. A session may include a login session between a client computing device and a server or other computer system. During the session, one or more account parameters of a user account of the session may be available. An account parameter may include values such as a login identifier, username, a session identifier, an account identifier, a domain indicator, or the like, where an account parameter space of an account parameter space vector may include categorized or quantified values of account parameters. For example, the query may include a natural language query such as "recent advances in health."

In some embodiments, one or more account parameters may be computed from a set of stored activities. For example, some embodiments may determine a set of previously-accessed documents and determine a set of domain vectors based on the set of previously-accessed documents. Some embodiments may then determine a set of clusters of the set of domain vectors using a clustering method, such as a density-based clustering method. For example, some embodiments may determine a count of domain vectors within a domain space region determined from dimensions of the domain space vector to select which set of domain vectors to in a cluster. Additionally, some embodiments may determine one or more account parameters based on the set of clusters. For example, some embodiments may determine a first account parameter indicating a domain vector representing a centroid of the cluster. As discussed further below, some embodiments may use the text of the query or a set of account parameters to sort or otherwise filter a set of documents.

In some embodiments, the query may be generated as part of a decision support system. For example, some embodiments may obtain inputs associated with a decision to perform one or more operational changes. Some embodiments may generate a query based on a context of the system, input data, a role of a user account, or the like. For example, some embodiments may determine that a user assigned with a first user role is tasked with determining whether to recommend an additional medical test. Some embodiments may retrieve a set of documents to provide guidance based on an account of the decision-maker that includes an expertise score for the domain associated with the decision. For example, some embodiments may determine that a user is associated with a "doctor" role based on an account corresponding to the user and is tasked with making a decision on whether to schedule a first operation in the domain of "pulmonary health." In response, some embodiments may provide guidance documents associated with the domain "pulmonary health" and associated with the class value corresponding to "doctor," such as a review study indicating statistical outcomes of the first operation. Additionally, some embodiments may determine that a second user is associated with a "nurse practitioner" role based on a second account corresponding to the second user and is tasked with making a decision on whether to schedule the first operation. In response, some embodiments may provide guidance documents associated with the domain "pulmonary health" and associated with the class value corresponding to "nurse practitioner," such as a guideline document instructing practitioners that the first operation is not recommended with a second opinion. As described further below, some embodiments may use scores associated with a user account to determine appropriate hierarchy levels of an ontology graph or set of ontology graphs and/or correspondingly appropriate documents.

The process 400 may include determining one or more learned representations based on the query, as indicated by block 408. As described elsewhere in this disclosure, a learned representation may include a quantitative value, a category, a vector, a list of data objects, or the like. For example, a learned representation may include an embedding vector associated with an n-gram. Some embodiments may use the same machine learning model as the ones described above. For example, some embodiments may use a trained encoder neural network or another neural network to determine a set of vertices of an ontology graph and use the same trained encoder neural network to determine the learned representations of n-grams of the query. As further discussed below, some embodiments may expand a query using a hierarchical set of ontology graphs, where a learned representation may be linked to other learned representations using a cluster of vertices or other aggregation of learned representations in a domain space.

The process 400 may include determining a set of query scores based on the set of learned representations or a set of parameters of the session, as indicated by block 412. In some embodiments, a set of query scores may be determined from a set of embedding vectors of a query. For example, the set of query scores may include a set of embedding vectors, additional values derived from the set of embedding vectors, a vector representing expertise scores in a set of domains, or the like. Alternatively, or in addition, some embodiments may determine the set of query scores based on a set of account parameters, where the set of account parameters may include a login identifier, a hash value based on the login identifier, data stored in an account of a user identified by the login identifier, or the like. For example, some embodiments may determine a query score vector comprising a weighted sum of a first domain vector and a second domain vector, where the first domain vector may include a set of domain indicators stored in a user account, and where the second domain vector may include a computed domain vector determined from the embedding vectors of the query.

The process 400 may include retrieving a set of stored documents based on the query score and a set of ontology graphs, as indicated by block 420. In some embodiments, a set of query scores for a query may be combined to form a query score vector. Some embodiments may use the set of query scores, either individually or in the form of a query score vector, to determine which documents to retrieve based on one or more documents referenced by vertices or other elements of an ontology graph. For example, some embodiments may determine that a set of embedding vectors of a query match with the first ontology graph's vertices, such as an ontology graph of medical terminology. Some embodiments may expand the query by determining associated concepts of the query via clusters or other aggregations of learned representations of n-grams of the query in a domain space combining ontology graphs at different hierarchies. For example, some embodiments may receive a query and match an n-gram of the query to a first concept via an embedding vector of the n-gram being part of a cluster of vectors associated with the concept. A search to retrieve documents may result in documents that are indexed by the concept, include the concept, or otherwise associated with the concept. Some embodiments may then retrieve a plurality of documents based on the set of embedding vectors of the query matching with one or more of the ontology graph's embedding vectors. The retrieved plurality of documents may be obtained based on the documents referred to or otherwise associated with the ontology graph's vertices.

Some embodiments may use one or more machine learning models to retrieve documents, summarizations based on documents, or the like as part of providing semantic search results after receiving a query. As discussed elsewhere in this disclosure, a machine learning model may include a set of decision trees forming a random decision forest, a neural network having an attention mechanism, a neural network having one or more recurrent neural network layers, a neural network having activation functions, ensemble models comprising different sub-models, or the like. For example, some embodiments may use a trained transformer neural network or other machine learning model to determine a set of dialog states values for a query and use the dialog state values in conjunction with n-grams of the query or associated concepts of the n-grams to retrieve a document. Various dialog state values may be determined, and may include an intent classification, a complexity classification, or the like. Some embodiments may train an instance of a machine learning model using a first set of question-answer pairs, where machine learning parameters or hyperparameters may be transferred to other instances of the machine learning model. Some embodiments may implement such parameter transfers as part of one or more transfer learning operations.

Various types of transfer learning operations may be performed. For example, some embodiments may use a set of transformer neural networks to select documents of a corpus for retrieval or processing based on the n-grams of the document and metadata associated with the document. Using a transformer neural network may converting n-grams into learned representations before determining one or more values for a dialog state or other output of the transformer neural network. For example, a trained transformer neural network may determine a key value usable to search through an index of a set of n-grams of a document, an ontology, or a corpus, where the index may associate key values representing n-grams or ontology graph vertices with representations of other n-grams or other ontology graph vertices. Some embodiments may perform one or more latent feature learning operations on n-grams of a corpus or an initial set of learned representations of the n-grams to determine a lower dimensional set of learned representations.

As described in this disclosure, some embodiments may transfer parameters of machine learning model, where the parameters may include a set of neural network parameters such as weights, biases, activation function parameters, or other values of the neurons of a neural network. Once transferred, these parameters may be used by a new instance of the neural network model or other machine learning model. For example, some embodiments can train a BERT-based machine learning model to predict answers based on training queries from a stored library of queries and answers, where the answers for the queries may include semantic search results. Some embodiments may train a machine learning model based on a set of training queries and a corresponding set of training documents that should be retrieved when the system is provided with the set of training queries. Additionally, some embodiments may substitute or augment the stored library of questions and answers with a second set of questions and answers that are filtered by an associated domain or class within the domain. Some embodiments may perform inductive transfer learning operations, such as multi-task learning operations or sequential transfer learning operations. Performing a set of multi-task transfer learning operations may include concurrently training a machine learning model (e.g., a recurrent neural network) to perform different tasks. For example, some embodiments may perform multi-task transfer learning operations to by training a set of machine learning models sharing one or more neural network layers to perform named entity recognition, part-of-speech tagging, relationship extraction, or other tasks, where the operations may include one or more operations described by Sanh et al (Sanh, V., Wolf, T. and Ruder, S., 2019, July. A hierarchical multi-task approach for learning embeddings from semantic tasks. In Proceedings of the AAAI Conference on Artificial Intelligence (Vol. 33, pp. 6949-6956)), which is incorporated herein by reference. In some embodiments, the training data used to perform multi-task transfer learning operations or other training operations to train a machine learning model described in this disclosure may include training that uses questions as inputs and documents of the corpus, data based on or associated with the documents of the corpus, or scores associated with the documents of the corpus as outputs.

Some embodiments may perform a set of sequential transfer learning operations by training a machine learning model using different sets of training data in a sequence. For example, some embodiments may train an instance of a machine learning model with a first set of training data and then train the pre-trained instance with a second set of training data, where the second set of training data may be adapted to a domain-specific or user-specific set of purposes. Some embodiments may generate a pre-trained machine learning model with training data having a set of training questions and set training documents from a corpus. Some embodiments may then adapt the pre-trained machine learning model by its outputs for an additional set of layers of a neural network model or another machine learning model (e.g., support vector machines, Random Forest, or the like). Alternatively, or in addition, some embodiments may use the transferred models as a starting set of parameters and further update the parameters based on additional training. For example, some embodiments may obtain an initial set of weights and biases for neurons of a neural network and update the set of weights and biases of the neural network during a second training operation with an additional set of training operations using a second set of training data, where the second set of training data may be more domain-specific or class-specific. Some embodiments may use an initial set of queries and expected responses to the queries based on a corpus to train a machine learning model using one or more operations described by Namazifar et al (Namazifar, M., Papangelis, A., Tur, G. and Hakkani-Tür, D., 2020. Language Model is All You Need: Natural Language Understanding as Question Answering. arXiv preprint arXiv: 2011.03023), which is incorporated herein by reference. For example, some embodiments may train a machine learning model in a first stage based on a pre-determined set of queries and responses, such as an ATIS dataset that is augmented with a pre-determined set of questions and answers based on the ATIS dataset. It should be recognized that some embodiments may use another dataset, such as an industry-specific or domain field-specific dataset to perform the first stage of training with a corresponding set of pre-determined questions and answers. Some embodiments may then update the machine learning model by applying a second training operation based on a specific class associated with the training data. For example, some embodiments may perform a second training operation to generate a machine learning model that retrieves text from documents in response to a query based on a specific user class of the user making the query.

Some embodiments may rank or filter the set of retrieved documents based on one or more operations based on domain indicators or other values associated with a query and domain indicators or other values associated with a user. For example, some embodiments may obtain a set of vectors indicating one or more domain expertise scores of a user, where the vector may be obtained from a UI element or a corresponding user account. After providing a query, a user may be permitted to interact with one or more UI elements to indicate their level of expertise in a set of domains, such as by selecting a category from a set of selectable categories and writing a numeric value ranging between the numbers one and five to indicate their preferred level of document complexity. This indicated preferred level of document complexity may then be used as a domain expertise score.

Some embodiments may retrieve a document by loading a document from a repository into a temporary or non-persistent memory. Alternatively, some embodiments may retrieve a document by loading an identifier, text portion, or other value based on the document into a temporary or non-persistent memory. For example, some embodiments may retrieve a document by retrieving the title of the document or another identifier of the document in a repository. A client computing device may then obtain the text of the document by sending an additional request to a corresponding document-storing repository with the identifier of the document.

In some applications, only a single domain is considered when filtering or sorting a set of documents based on a domain expertise score. Some embodiments may sort a set of documents based on a hierarchy of a set of ontology graphs or their corresponding hierarchy of domain expertise values. For example, a first document may be associated most with a first ontology graph that is itself associated with a domain score of one, and a second document may be associated with a second ontology graph that is itself associated with a domain score of eight. After obtaining a query associated with a domain score equal to seven, some embodiments may select the second document for retrieval and not select the first document for retrieval. Alternatively, after retrieving both documents, some embodiments may display the second document at the top of a list of documents in a UI window, where the first document may be at a lower position in the UI window than the second document.

For example, if a user is associated with a domain class vector of "[0, 5, 3]," representing expertise scores in three different domains, some embodiments may rank a set of documents based on their distance from the domain vector in a domain class space, where the domain class vector may be used as a query score vector. In some embodiments, the distance may be used as a relevance score for a document and may indicate the likelihood that the document will be considered meaningful or otherwise relevant for a query provided by the user. Alternatively, or in addition, the relevance score may be determined based on the distance. For example, some embodiments may determine a relevance score based on the distance and based on the number of occurrences of n-grams shared between the document and a corresponding query. After determining a distance measurement between the query score vector and each respective domain vector of a respective document of a set of documents or a relevance score based on the distance measurement, some embodiments may determine a ranking of the plurality of distance measurements and use the ranking to determine which set of retrieved documents to display. As described above, a document domain vector may be determined based on word complexity, phrase complexity, syntax, grammar, or other features of a text document. Additionally, or alternatively, some embodiments may update or generate a domain vector for a document based on the count and types of vertices of an ontology graph that corresponds with the embedding vectors of the document.

Some embodiments may then provide the set of retrieved documents to a computing device for display, as indicated by block 430. some embodiments may obtain a vector indicating a domain expertise score based on data stored in association with a user account or other type of account data or determined from a query score computed from the set of embedding vectors of a query described above. For example, some embodiments may obtain an expertise score based on a set of user account data indicating that a user has an interest in "cardiology" and has an expertise score of "9" in association with the domain "cardiology." In response, some embodiments may rank the set of retrieved documents based on their distance to the set of domain expertise scores in a domain expertise dimension space.

Providing the set of retrieved documents may include sending a list of the identifiers and corresponding text of the set of retrieved documents to a client computing device. Alternatively, some embodiments may initially send the list of the identifiers of the documents in an ordered sequence to a client computing device. In response to a selection of an identifier in a UI element being displayed on the computing device, some embodiments may then provide the text of the selected document. As discussed elsewhere in this discussion, some embodiments may use one more indices updated based on a set of ontology graphs to reduce the time or computational resource use required to provide a set of documents based on a query.

Figure 5:
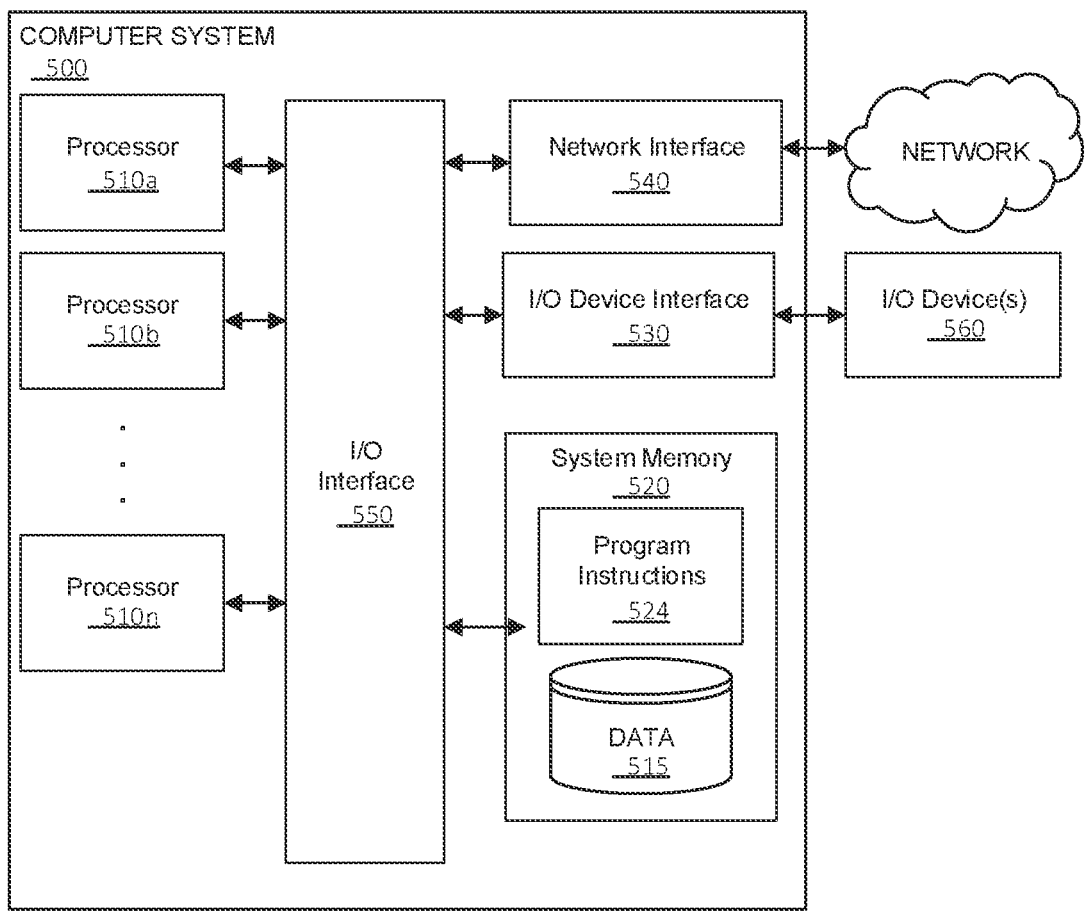
FIG. 5 shows an example of a computer system by which the present techniques may be implemented in accordance with some embodiments.

FIG. 5 shows an example of a computer system by which the present techniques may be implemented in accordance with some embodiments. FIG. 5 is a diagram that illustrates an exemplary computer system 500 in accordance with embodiments of the present technique. Various portions of systems and methods described herein, may include or be executed on one or more computer systems similar to computer system 500. Further, processes and modules described herein may be executed by one or more processing systems similar to that of computer system 500.

Computer system 500 may include one or more processors (e.g., processors 510a-510n) coupled to system memory 520, an input/output I/O device interface 530, and a network interface 540 via an input/output (I/O) interface 550. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computer system 500. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 520). Computer system 500 may be a uni-processor system including one processor (e.g., processor 510a), or a multi-processor system including any number of suitable processors (e.g., 510a-510n). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computer system 500 may include a plurality of computing devices (e.g., distributed computer systems) to implement various processing functions.

I/O device interface 530 may provide an interface for connection of one or more I/O devices 560 to computer system 500. I/O devices may include devices that receive input (e.g., from a user) or output information (e.g., to a user). I/O devices 560 may include, for example, graphical UI presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 560 may be connected to computer system 500 through a wired or wireless connection. I/O devices 560 may be connected to computer system 500 from a remote location. I/O devices 560 located on remote computer system, for example, may be connected to computer system 500 via a network and network interface 540.

Network interface 540 may include a network adapter that provides for connection of computer system 500 to a network. Network interface may 540 may facilitate data exchange between computer system 500 and other devices connected to the network. Network interface 540 may support wired or wireless communication. The network may include an electronic communication network, such as the Internet, a local area network (LAN), a wide area network (WAN), a cellular communications network, or the like.

System memory 520 may be configured to store program instructions 524 or data 515. Program instructions 524 may be executable by a processor (e.g., one or more of processors 510a-510n) to implement one or more embodiments of the present techniques. Program instructions 524 may include modules of computer program instructions for implementing one or more techniques described herein with regard to various processing modules. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 520 may include a tangible program carrier having program instructions stored thereon. A tangible program carrier may include a non-transitory computer readable storage medium. A non-transitory computer readable storage medium may include a machine-readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM or DVD-ROM, hard-drives), or the like. System memory 520 may include a non-transitory computer readable storage medium that may have program instructions stored thereon that are executable by a computer processor (e.g., one or more of processors 510a-510n) to cause the subject matter and the functional operations described herein. A memory (e.g., system memory 520) may include a single memory device or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times.

I/O interface 550 may be configured to coordinate I/O traffic between processors 510a-510n, system memory 520, network interface 540, I/O devices 560, or other peripheral devices. I/O interface 550 may perform protocol, timing, or other data transformations to convert data signals from one component (e.g., system memory 520) into a format suitable for use by another component (e.g., processors 510a-510n). I/O interface 550 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computer system 500 or multiple computer systems 500 configured to host different portions or instances of embodiments. Multiple computer systems 500 may provide for parallel or sequential processing/execution of one or more portions of the techniques described herein.

Those skilled in the art will appreciate that computer system 500 is merely illustrative and is not intended to limit the scope of the techniques described herein. Computer system 500 may include any combination of devices or software that may perform or otherwise provide for the performance of the techniques described herein. For example, computer system 500 may include or be a combination of a cloud-computer system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computer system 500 may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

II. Cross-Class Ontology Integration

Workflows in various domains involve a mixture of general knowledge understanding, domain-specific understanding, and quantitative understanding. A significant challenge to using NLP for domain-specific workflows is the gap between a general knowledge environment and a domain-specific environment. Domain-specific knowledge may include differing interpretations of shared terminology, domain-specific logical relationships that differ between domains, patterns that are apparent or relevant only in specific domains, quantitative relationships, or the like. Additionally, domain-specific knowledge may be contradictory to knowledge encoded in data provided by or otherwise obtained from a general knowledge system. Thus, as a domain grows more specialized, NLP systems trained on general knowledge systems may grow increasingly unreliable when used within a specific domain. However, domain-specific data is often considerably less voluminous relative to general knowledge data, which may make domain-specific data inadequate for various NLP training tasks. The unreliability of NLP systems may then generate or exacerbate errors in a decision-support system, which may result in poor recommendations or automated responses in domain-specific workflows.

As discussed elsewhere in this disclosure, some embodiments include a plurality of ontologies associated with different domains. In many instances, these ontologies may be independently using a set of different corpuses or implemented with different ontological objectives. Integrating these ontologies may often prove useful to accelerate cross-domain searches and determining new insights based on cross-domain knowledge. However, the integration of these domains may be made difficult due to different logical relationships, domain vocabulary, or categorical locations.

Some embodiments may integrate a first ontology with other ontologies to form the ontology system. Some embodiments may integrate the first ontology with other ontologies based on a second ontology associating words or other n-grams of the first ontology with the other ontologies, allowing words and concepts to be hierarchically linked across different domains or classes of expertise within the domains. Some embodiments may include a set of UI elements to control a modular knowledge system and provide visual indicators to indicate whether an ontology combination passes or fails a set of rules. Some embodiments may present visualizations of the different types of edges governing vertex relationships within an ontology graph or other vertex relationships, where the ontology graph may represent an ontology. Some embodiments may further present visualizations of query interpretations based on the set of ontology combinations. Some embodiments may include these visualizations in a decision-support platform. In some embodiments, the decision-support platform may provide human users with visual indicators or UI elements to view or modify a set of parameters used by the decision-support platform to provide recommendations or take actions.

By performing the operations described above, some embodiments may construct a knowledge fabric usable for a decision-support platform in accordance with an NLP system trained across multiple domain levels. Some embodiments may perform general language encoding or domain-specific language encoding on text. Additionally, some embodiments may convert other forms of media (e.g., video, audio, images) into text data for analysis and incorporate the information in one or more domain levels. Some embodiments may perform query expansion using the set of ontology graphs, a trained learning system, or the like. Some embodiments may search through related knowledge systems based on the set of ontology graphs to provide additional graph-based relationships corresponding to domain-specific insights or cross-domain insights in response to updates to the set of ontology graphs. Some embodiments may analyze and update elements of an ontology graph or other elements of a structured knowledge base in response to user feedback to increase the speed and accuracy of a decision-support system.

In some embodiments, an NLP system, NLU system, or Artificial Intelligence (AI) system may be combined with ingested documents and other data to create a structured knowledge base of a knowledge fabric usable to provide data in response to queries. For example, some embodiments may obtain documents, tagged media files, data generated from media files (e.g., transcripts of videos, recognized objects in videos, or the like). Some embodiments may then classify the documents and other data into a set of domain-specific categories and generate or otherwise update a set of ontology graphs based on the provided data. As further discussed in this disclosure, some embodiments may then determine relationships between the set of ontology graphs using one or more machine learning operations of an NLP system to construct or otherwise update a set of ontology graphs that includes one or more ontology graphs, where each graph may be specific to a domain or class within the domain. The set of ontology graphs may be used as part of a knowledge fabric, and may be used by one or more NLP, NLU, or other AI systems to provide data, recommendations, workflow instructions, or programmed operations.

Some embodiments may use a layered approach with a hierarchical tool chain ("Cognitive Tower") that may improve performance over other general-domain AI systems. Some embodiments may use transfer learning from language models enhanced by domain-specific, enterprise-specific, or workflow-specific contextual models. Additionally, some embodiments may customize a workflow pipeline for specific contexts, which may improve the accuracy of output recommendations or instructions. Some embodiments may modify one or more learning parameters based on a set of supervised and unsupervised learning operations performed in response to human interaction, which may further improve user efficiency and system accuracy.

Figure 6:
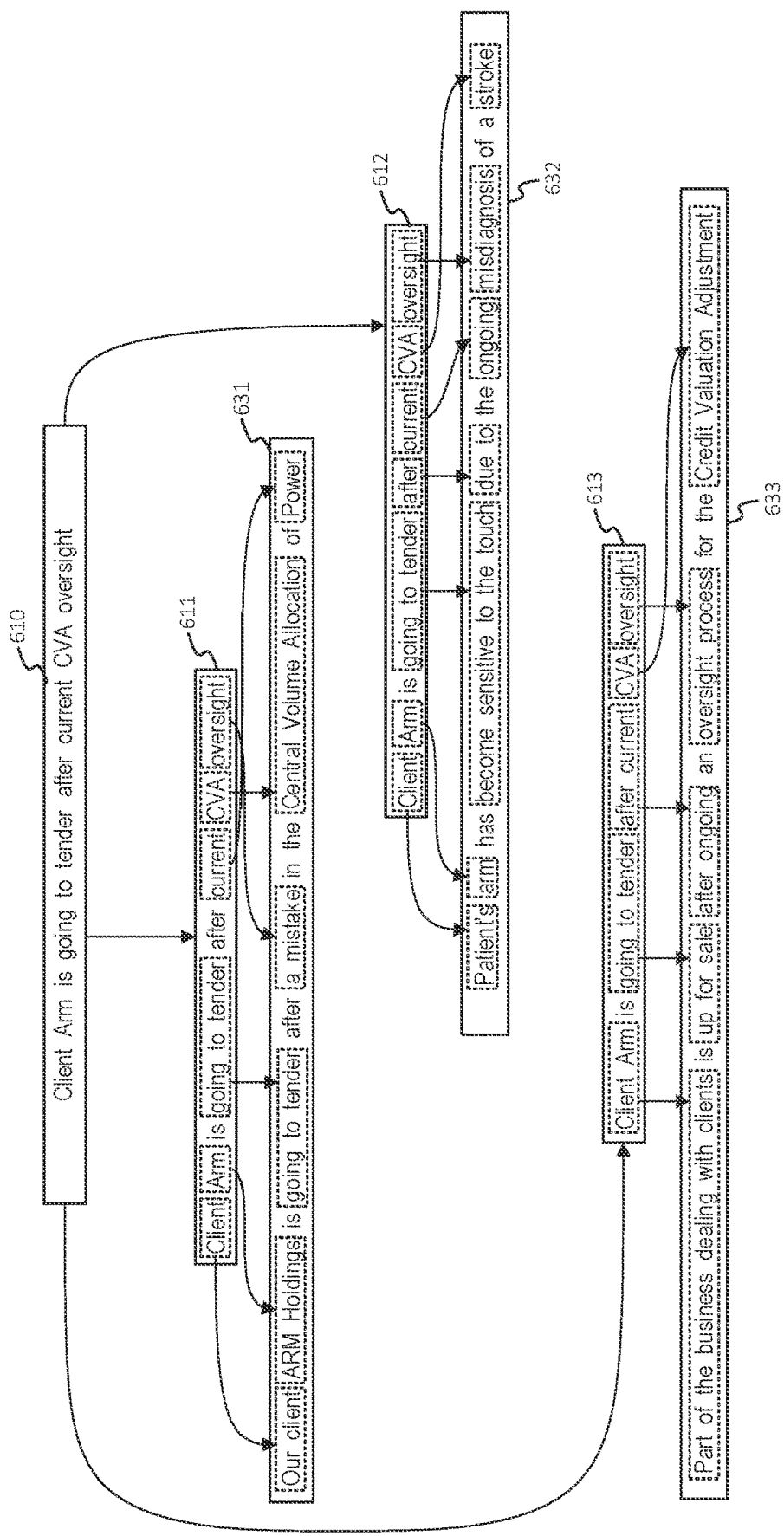
FIG. 6 shows an example of different statement expansions based on an initial statement, in accordance with some embodiments of the present techniques.

FIG. 6 shows an example of different statement expansions based on an initial statement, in accordance with some embodiments of the present techniques. The statement "Client Arm is going tender after current CVA oversight" shown in the box 610 is repeated three times in the boxes 611-613. For example, some embodiments may obtain a first ontology graph in a electrical knowledge domain that separates the statement "Client Arm is going tender after current CVA oversight" into the items "client," "arm," "going to tender," "current," "CVA," and "oversight." Using the first ontology graph, some embodiments may convert the term "client" into "our client," convert the term "arm" into "ARM holdings," convert the word "current" into the phrase "Power,"

convert the item "CVA" into the phrase "Central Volume Allocation," and convert the item "oversight" into the phrase "a mistake." Using these mappings, some embodiments may provide the phrase "our client ARM Holdings is going to tender after a mistake in the Central Volume Allocation of Power," which is shown in the box 631 using the first ontology graph.

Some embodiments may obtain a second ontology graph in a medical knowledge domain that separates the statement "Client Arm is going tender after current CVA oversight" into the items, "client," "arm," "going to tender," "after," "current," "CVA," and "oversight." Using the second ontology graph, some embodiments may convert the word "client" into "patient," convert the word "after" into the phrase "due to," convert the word "current" into the phrase "ongoing," convert the acronym "CVA" into the word "stroke," and convert the word "oversight" into the word "misdiagnosis." Using these mappings, some embodiments may provide the phrase, "patient's arm has become sensitive to the touch due to the ongoing misdiagnosis of a stroke," which is shown in the box 632 using the second ontology graph.

Some embodiments may obtain a third ontology graph in a business knowledge domain that separates the statement "Client Arm is going tender after current CVA oversight" into the items, "client," "arm," "going to tender," "after current," "CVA," and "oversight." Using the third ontology graph, some embodiments may convert the phrase "client arm" into the phrase "Part of the business dealing with clients," convert the phrase "going to tender" into the phrase "up for sale," convert the phrase "after current" into the phrase "after ongoing," convert the acronym "CVA" into the phrase "credit valuation adjustment," and convert the word "oversight" into the phrase "oversight process." Using these mappings, some embodiments may provide the phrase, "part of the business dealing with clients is up for sale after ongoing an oversight process for the Credit Valuation Adjustment," which is shown in the box 633 using the third ontology graph.

Figure 7:
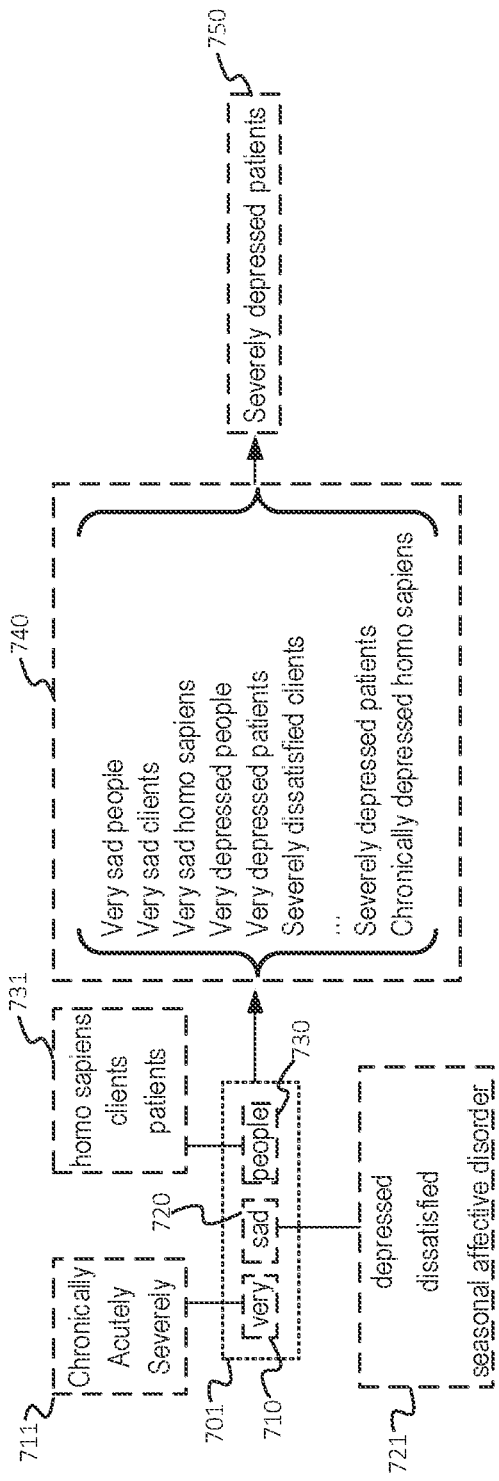
FIG. 7 shows an example of an initial query and an expanded query, in accordance with some embodiments of the present techniques.

FIG. 7 shows an example of an initial query and an expanded query, in accordance with some embodiments of the present techniques. The query 701 includes a first n-gram 710, a second n-gram 720, and a third n-gram 730. As shown in FIG. 7, the first n-gram 710 is the word "very," the second n-gram 720 is the word, "720," and the third n-gram 730 is the word "people." It should be recognized that while each word in the query 701 is an n-gram of the query 701, some embodiments may use syllables, phrases, characters, or some combination thereof as n-grams.

As discussed in this disclosure, each of the n-grams 710, 720, and 730 may be associated with other n-grams using a set of ontology graphs. The first n-gram 710 may be associated with a first set of alternative n-grams shown in the box 711. The second n-gram 720 may be associated with a second set of alternative n-grams shown in the box 721. The third n-gram 730 may be associated with a third set of alternative n-grams shown in the box 731. As further discussed below, two or more of the n-grams in the box 711, 721, or 731 may be associated with different domains or classes. For example, the n-gram "homo sapien" may be associated with a first embedding vector that is indicated to be part of a first domain labeled "biology" via an associated ontology graph vertex of an ontology graph categorized as being of the first domain. Additionally, the n-gram "clients" may be associated with a second embedding vector that is indicated to be part of a second domain labeled "business" via an associated ontology graph vertex of an ontology graph categorized as being of the second domain.

Some embodiments may generate, either in sequence or in parallel, a set of expanded queries 740. Each of the expanded queries 740 may be associated with a score associated with a search context, a program environment context, parameters of an account used to perform the search, or the like. For example, some embodiments may receive the query 701 from a first user logged in with a first user account and generate a first set of scores for each of the expanded queries 740 based on one or more domains or an expertise scores associated with the first account. Some embodiments may receive the query 701 from a second user logged in with a second user account and generate a second set of scores for each of the expanded queries 740 based on one or more domains or an expertise scores associated with the second account, where the first and second set of scores are different from each other. For example, a first score for an expanded query "very dissatisfied clients" may be 15% for a first user account indicated as being included in a first domain labeled "psychology physician" and may be 95% for a second user account indicated as being included in a second domain labeled "customer outreach staff." Additionally, some embodiments may determine additional scores based on domains labeled "severely depressed patients." Based on a ranking determined from the scores, some embodiments may select one or more expanded queries, such as the expanded query 750.

Figure 8:
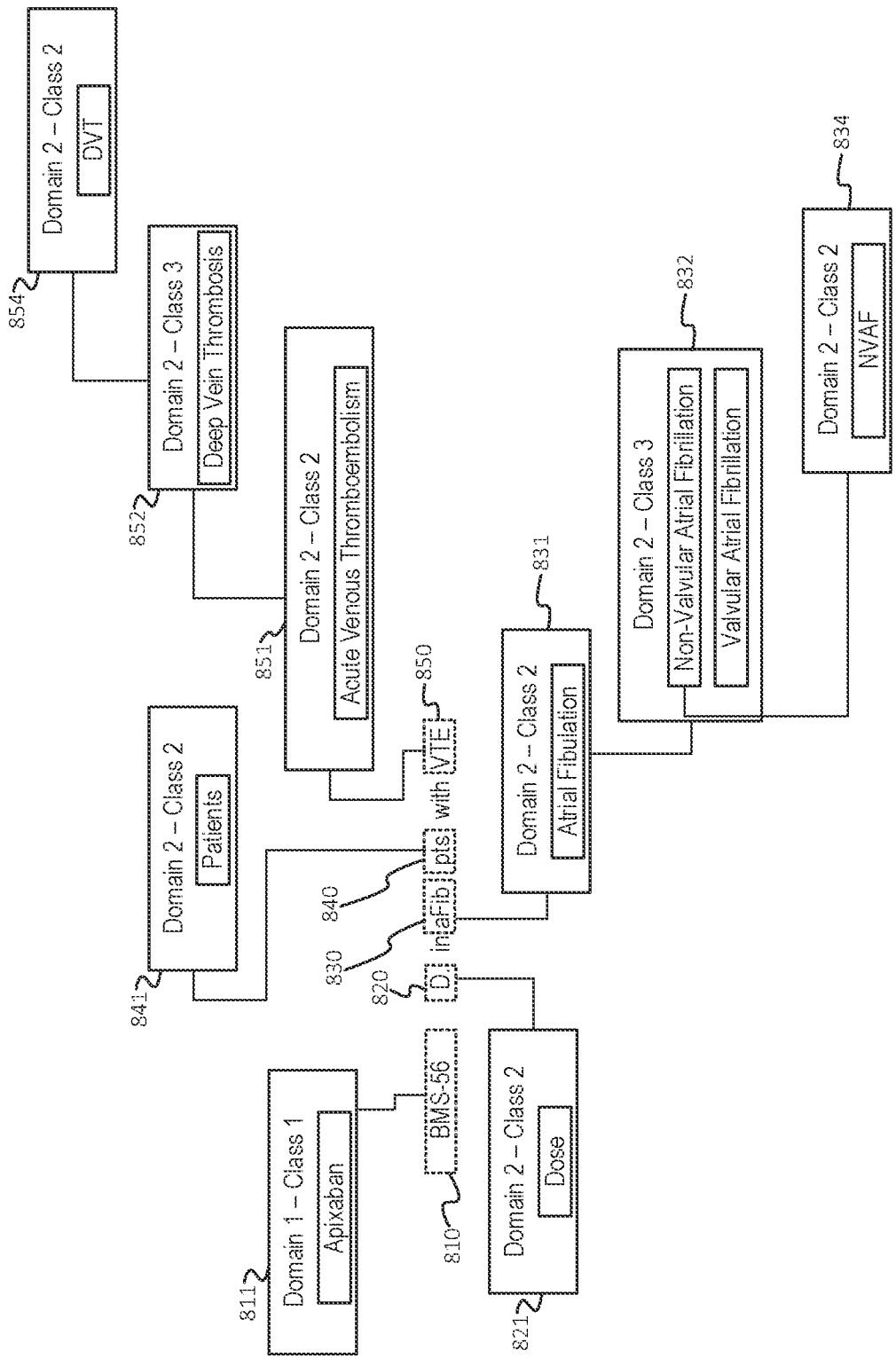
FIG. 8 shows the use of ontology graphs associated with different classes when determining an expanded query, in accordance with some embodiments of the present techniques.

FIG. 8 shows the use of ontology graphs associated with different classes when determining an expanded query, in accordance with some embodiments of the present techniques. The query "BMS-56 D. in aFib pts with VTE" includes a first n-gram 810, second n-gram 820, third n-gram 830, fourth n-gram 840, and fifth n-gram 850, representing the terms "BMS-56," "D.," "aFib," "pts," and "VTE," respectively. Some embodiments may navigate between ontology graphs of different domains and hierarchies within a domain to determine one or more alternative n-grams or associated concepts. For example, some embodiments may determine that the first n-gram 810 is associated with a first related n-gram "Apixaban" shown in the box 811 based on a first edge of a first ontology graph associated with a first domain. In some embodiments, the first edge may associate a first vertex of the ontology graph representing the n-gram "BMS-56" with a second vertex of the ontology graph representing the n-gram "Apixaban." Similarly, some embodiments may determine that the second n-gram 820 is associated with a second related n-gram "Dose" shown in the box 821 based on a second edge of a second ontology graph. In some embodiments, the second edge may associate a third vertex representing the n-gram "D." with a fourth vertex of the second ontology graph representing the n-gram "Dose," where both the third vertex and fourth vertex are vertices of the second ontology graph. Similarly, some embodiments may determine that the fourth n-gram 840 is associated with a fourth related n-gram "Patients" shown in the box 841 based on a third edge of the ontology graph. In some embodiments, the third edge associates a fifth vertex representing the n-gram "pts" with a sixth vertex of the second ontology graph representing the n-gram "Patients."

As shown in FIG. 8, some embodiments may retrieve multiple terms based on a respective domain or class category within the domain. For example, some embodiments may first determine that the third n-gram 830 is associated with a fifth related n-gram "Atrial Fibulation" shown in the box 831 based on a fourth edge of the second ontology graph. In some embodiments, the fourth edge may associate a seventh vertex of the second ontology graph representing the n-gram "aFib" with an eighth vertex of the second ontology graph representing the n-gram "Atrial Fibulation." Additionally, in some embodiments, a first cross-graph edge may associate the eighth vertex with a ninth vertex representing the n-gram "Non-Valvular Atrial Fibulation" shown in a box 832, the ninth vertex being a vertex of a third ontology graph. Additionally, in some embodiments, a second cross-graph edge may associate the eighth vertex with a tenth vertex representing the n-gram "Valvular Atrial Fibulation" also shown in the box 832, the tenth vertex also being a vertex of the third ontology graph. Some embodiments may then determine that the tenth vertex is associated with an eleventh vertex representing the n-gram "NVAF" via a third cross-graph edge, the eleventh vertex being a vertex of the second ontology graph. In some embodiments, the second and third ontology graphs may share a domain labeled "Domain 2," but be associated with different hierarchies, where the second ontology graph is associated with the "class 2" class, and where the third ontology graph is associated with the "class 3."

As indicated above, after updating a set of ontology graphs by forming cross-graph edges relating vertices of different ontology graphs, some embodiments may provide previously-undetected associations between different vertices. For example, the first cross-graph edge associating the eighth vertex of the third ontology graph with the ninth vertex of the second ontology graph may be used to determine an association between the n-gram "aFib" and the n-gram "Valvular Atrial Fibrillation." Additionally, some embodiments may detect previously non-established links between vertices of a same ontology graph by using edges associating vertices of ontology graphs having different domains or classes. For example, as shown in the association between the n-gram "Atrial Fibrillation" written in the box 831 and the n-gram "NVAF" written in the box 834, some embodiments may detect an association between the n-gram "atrial fibulation" and the n-gram "NVAF," where the association may be recorded in one or more of the vertices or otherwise stored in a database (e.g., as an ontological triple). This association may be used to include the n-gram "NVAF" when expanding a query having the n-gram "aFib," generating a set of expanded queries, or otherwise performing searches to retrieve documents using query that includes the n-gram "aFib" or "Atrial Fibulation."

Similarly, some embodiments may first determine that the fifth n-gram 850 is associated with a related n-gram "Acute Venous Thromboembolism" shown in the box 851 based on a fifth edge of the second ontology graph. In some embodiments, the fifth edge may associate a twelfth vertex of the second ontology graph representing the n-gram "VTE" with a thirteenth vertex of the second ontology graph representing the n-gram "Acute Venous Thromoboembolism." Additionally, in some embodiments, a first cross-graph edge may associate the thirteenth vertex with a fourteenth vertex representing the n-gram "Deep Vein Thrombosis" shown in the box 852, the fourteenth vertex being a vertex of the third ontology graph. Additionally, in some embodiments, a second cross-graph edge may associate the fourteenth vertex with a fifteenth vertex representing the n-gram "DVT" shown in the second ontology graph, the second vertex being a vertex of the second ontology graph.

Figure 9:
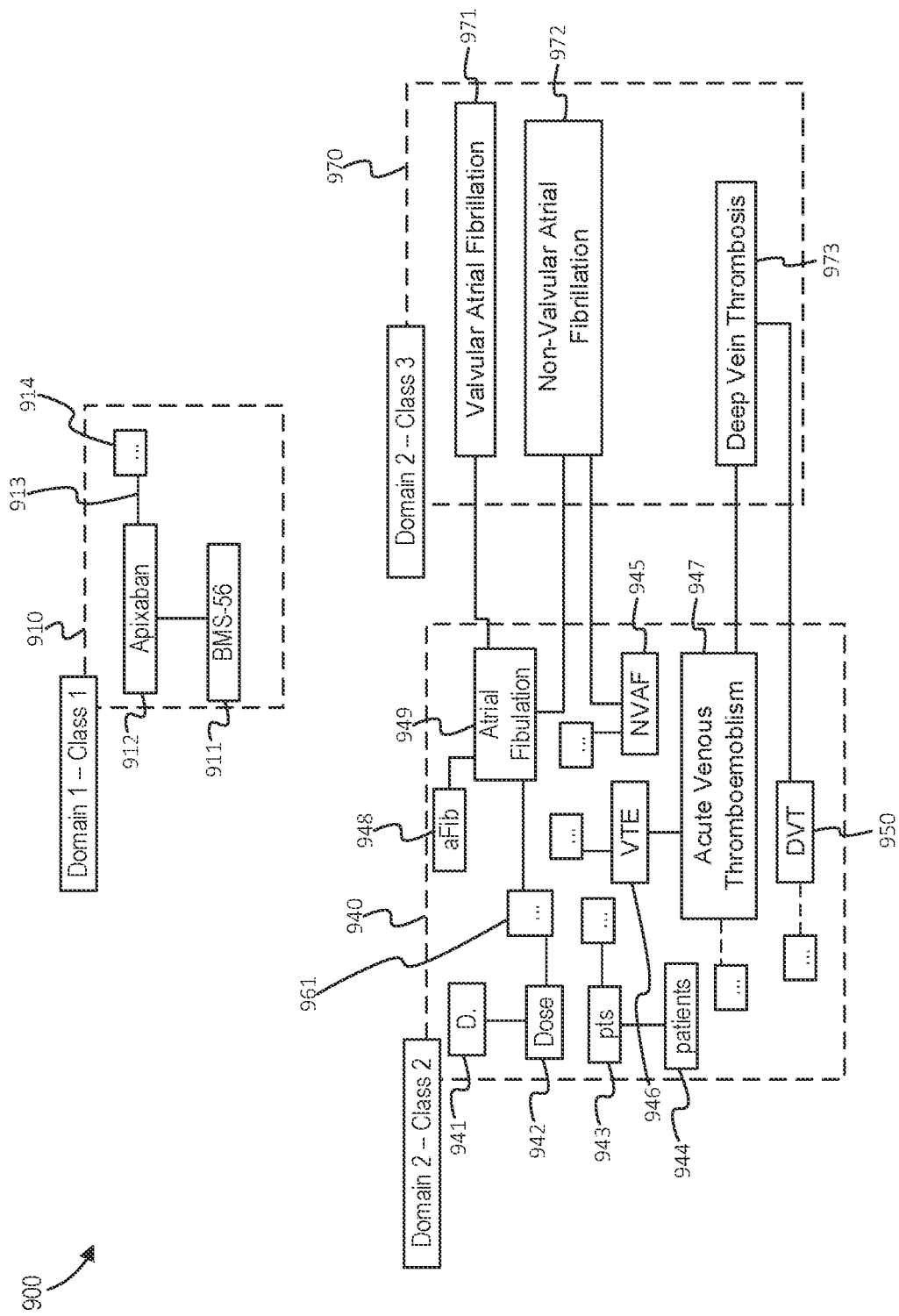
FIG. 9 shows a representation of ontology graphs associated with different classes of a hierarchical set of ontology graphs, in accordance with some embodiments of the present techniques.

FIG. 9 shows a representation of ontology graphs associated with different classes of a hierarchical set of ontology graphs, in accordance with some embodiments of the present techniques. FIG. 9 displays a set of ontology graphs 900, the set of ontology graphs including a first ontology graph 910 having vertices 911-912, a second ontology graph 940 having vertices 941-951, and a third ontology graph 970 having vertices 971-973. The first ontology graph 910 is categorized with a first domain labeled "domain 1" and further categorized with a class category "Class 1." The first ontology graph 910 includes a vertex 911 and a vertex 912, where the vertex 911 is labeled with the n-gram "BMS-56," and where the vertex 912 is labeled with the n-gram labeled "Apixaban." Additionally, the first ontology graph 910 includes a subgraph of additional vertices represented by the box 914, where the vertex 912 is associated with the subgraph of additional vertices represented by the box 914 via the ontology graph edge 913. As discussed elsewhere in this disclosure, some embodiments may determine additional query expansions, update indices, or perform other actions based on vertices of the subgraph represented by the box 914 after a determination that a query or search retrieves the vertex 912.

Various types of data structures stored in computer memory may be used to represent an ontology graph, such as the first ontology graph 910, the second ontology graph 940, or the third ontology graph 970. For example, some embodiments may store each vertex as a record in a data table, where each respective identifier of a respective vertex may serve as an index value usable to retrieve the respective vertex and its associated values. Alternatively, or in addition, a vertex may be stored as a plurality of values distributed across a plurality of databases, arrays, data objects, or the like. For example, some embodiments may store a first array of values, a second array of pairs or triplets of values, and a data table of records. Each value of the first array may include an identifier to uniquely identify a vertex. Each pair or triplet of values of the second array may include a pair of the unique identifiers of the vertices indicating an ontology graph edge. For example, if the vertex 911 and the vertex 912 have the unique identifiers "911" and "912," respectively, the pair of values may include "[911, 912]," which may represent or otherwise indicate an ontology graph edge associating the vertices 911 and 912. The data table of records may include additional values associated with the vertex, such as a label of the vertex, domain values associated with the vertex, hierarchy values associated with the vertex (e.g., an expertise score), ontology graph containing the vertex, or the like. For example, the data table of records may include a first record indexed by the identifier "z3613c-1," which may represent the vertex 911, where the first record includes an "n-gram" field that is filled with the value "BMS-56." Similarly, the data table of records may include a second record indexed by the identifier "q3335c-1," which may represent the vertex 912, where the first record includes an "n-gram" field that is filled with the value "Apixaban."

The second ontology graph 940 is categorized with a first domain labeled "Domain 2" and further categorized with a class category "Class 2," which may indicate the second ontology graph 940 is a graph in "Domain 2" of the class "Class 2." The vertex 941 is labeled with the text "D." and associated with the vertex 942, which is labeled with the text "Dose," where the vertex 942 may be further connected to a set of other vertices represented by a box 961. As discussed elsewhere in this disclosure, an index may be constructed or updated based on the ontology graph edge associating the vertex 941 and the vertex 942. For example, some embodiments may detect the second n-gram 820 "D." and, in response, retrieve the n-gram "Dose" shown in the box 821 based on the index constructed from the edge associating the vertex 941 with the vertex 942. Some embodiments may retrieve the n-gram "Dose" by referring to an index of a set of records indicating an association between the n-gram "D." and the n-gram "Dose," where the index may be constructed from or otherwise updated using the second ontology graph 940. Alternatively, or in addition, some embodiments may retrieve the n-gram "Dose" by using to a set of ontology graph edges, such as an array of pairs of identifiers as discussed above. For example, some embodiments may determine that an n-gram is a label for a vertex identified by a first identifier of a pair of identifiers and, in response, retrieve a vertex or its associated values (e.g., an identifier, a label, an associated category, a set of associated scores, or the like) that is identified by the other identifier of the pair of values.

As further shown for the second ontology graph 940, the vertex 943 is labeled with the text "pts" and associated with the vertex 944, which is labeled with the text "patients." As discussed elsewhere in this disclosure, some embodiments may detect the fourth n-gram 840 "pts" and, in response, retrieve the fourth n-gram "patients" shown in the box 841. Some embodiments may perform this retrieval based on the ontology graph edge associating the vertex 943 and 944 using one or more operations similar to those described for retrieving the n-gram "Dose" in response to detecting the n-gram "D." Similarly, as described above, some embodiments may detect the first n-gram 810 "BMS-56" and, in response, retrieve the n-gram "Apixaban" shown in the box 812 based on the ontology graph edge associating the vertices 911 to 912.

As further shown for the second ontology graph 940 and the third ontology graph 970, indirect associations between vertices may be used to expand a query or the rank scores associated with the query, where an indirect association may be characterized by a set of edges from a first vertex to a second vertex that includes at least two graph edges. For example, the third n-gram 830 includes the text "aFib" and may be associated with the n-gram "Atrial Fibulation" shown in the box 831 based on the association between the vertex 948 labeled "aFib" and the vertex 949 labeled "Atrial Fibulation" using one or more of the operations described above. Some embodiments may then, based on cross-graph edges associating the vertex 949 with the vertices 971 and 972, retrieve the n-grams "Non-Valvular Atrial Fibrillation" and "Valvular Atrial Fibulation" shown in the box 832. In some embodiments, the cross-graph edges may be stored in a memory in a format similar to or different from ontology graph edges. For example, a cross-graph edge may be an ontology graph edge that is stored in a separate array of values, where each entry in the separate array of values indicates a first vertex, a first ontology graph comprising the first vertex, a second vertex, and a second ontology graph comprising the second vertex.

As disclosed elsewhere, some embodiments may prioritize or otherwise update a ranking of similar n-grams with respect to a first n-gram. For example, the ranking associated with the n-grams "Non-Valvular Atrial Fibrillation" and "Valvular Atrial Fibulation" as shown by the vertices 971 and 972 may be based on the class values of the ontology graphs they are part of. For example, some embodiments may receive a query from a user having an account indicating that the user is a "class 3" user for the domain "domain 2." In response, some embodiments may update a ranking of documents retrieved using the term "aFib" such that documents retrieved using an expanded query having the n-gram "Non-Valvular Atrial Fibulation" shown in the box 832 is assigned a greater priority in a search ranking. For example, a first document and second document may have been retrieved based on the term "aFib" and a second document may have been retrieved based on the n-gram "Non-Valvular Atrial Fibulation." The first document may have been initially assigned a relevance score of "90" and the second document may have been initially assigned a relevance score of "90." As further discussed in this disclosure, various operations may be performed to modify a relevance score, such as by adding, subtracting, multiplying, applying an exponential term, or the like, where it should be understood that the prioritization of a document in a set of query results may be caused by either an increase or decrease of a relevance score associated with a document. For example, some embodiments may prioritize greater relevance scores over lesser relevance scores such that documents with greater relevance scores are displayed before documents with a lower relevance score are displayed. Alternatively, or in addition, some embodiments may display a title or text from a higher-score document above a title or text of a lower-score document on a UI screen. Alternatively, some embodiments may prioritize lesser relevance scores over greater relevance scores such that documents with lesser relevance scores are displayed before documents with a greater relevance score or displayed higher on a UI screen than a document with a greater relevance score.

As described above, the n-gram "Non-Valvular Atrial Fibrillation" shown in the box 832 may be associated with the n-gram "NVAF" shown in the box 834, where this association may be used to expand a query to use the term "NVAF" when searching for documents. In some embodiments, the association between the two n-grams may be determined based on the association between the vertex 972 labeled "Non-Valvular Atrial Fibrillation" and the vertex 945 labeled "NVAF" using one or more of the operations described above. As described above, some embodiments may generate an expanded query that includes the n-gram "NVAF" in place of or in addition to the n-gram "Non-Valvular Atrial Fibulation." Alternatively, or in addition, some embodiments may generate an expanded query that includes the n-gram "NVAF" in place of or in addition to related terms such as "aFib" based on the indirect association between edges connecting the vertex 948, the vertex 949, the vertex 972, and the vertex 945. For example, after receiving a query including the n-gram "aFib," some embodiments may generate an expanded query that includes the n-gram "DVT" for use in a semantic search. As further described below, some embodiments may update the second ontology graph 940 or an index based on the second ontology graph 940 in response to a detection of the multi-edge association between vertices. For example, if no edges associated the vertex 948 with the vertex 945, some embodiments may construct an edge associating the two vertices, such as by adding a vertex identifier pair to an array of edges, updating a set of records representing one or both vertices, or the like.

As described above, the fifth n-gram 850 includes the text "VTE" and may be associated with the n-gram "Acute Venous Thromboembolism" shown in the box 851 based on the association between the vertex 946 labeled "VTE" and the vertex 947 labeled "Acute Venous Thromboembolism" using one or more of the operations described above. Some embodiments may then, based on cross-graph edges associating the vertex 947 with the vertex 973 of the third ontology graph 970, retrieve the n-gram "Deep Vein Thrombosis." Furthermore, as described above, the n-gram "Deep Vein Thrombosis" shown in the box 852 may be associated with the n-gram "DVT" shown in the box 854, where this association may be used to expand a query to use the term "DVT" when searching for documents. In some embodiments, the association between these two n-grams may be determined based on the association between the vertex 973 labeled "Deep Vein Thrombosis" and the vertex 950 labeled "DVT" using one or more of the operations described above.

As described above, some embodiments may generate an expanded query that includes the n-gram "DVT" in place of or in addition to the n-grams "VTE," "Acute Venous Thromboembolism," or "Deep Vein Thrombosis" based on the vertex connections formed by the edges connecting the vertex 946, vertex 947, the vertex 973, and the vertex 950. Some embodiments may update the second ontology graph 940 or an index based on the second ontology graph 940 in response to a detection of the multi-edge association between vertices. For example, if no edges associated the vertex 946 with the vertex 950, some embodiments may generate an edge associating the two vertices, such as by adding a vertex identifier pair to an array of edges, updating a set of records representing one or both vertices, or the like. Future queries that include the n-gram "VTE" may more quickly or efficiently provide results based on the n-gram "DVT" as a result of the newly-generated edge. For example, some embodiments may prioritize results received from accessing an index constructed from an ontology graph instead of accessing the ontology graph directly. Some embodiments may update the index in response to a newly-generated edge between two vertices by including an additional link associating the n-gram "DVT" and "VTE" in the index before using the updated index to perform subsequent searches using the n-gram "VTE." Furthermore, it should be noted that while the set of ontology graphs are displayed with n-grams, other labels may be used. For example, the vertices of the set of ontology graphs 900 may include embedding vectors as identifiers of the vertices, where two or more vertices may be labeled with the same n-gram while having different embedding vectors.

Figure 10:
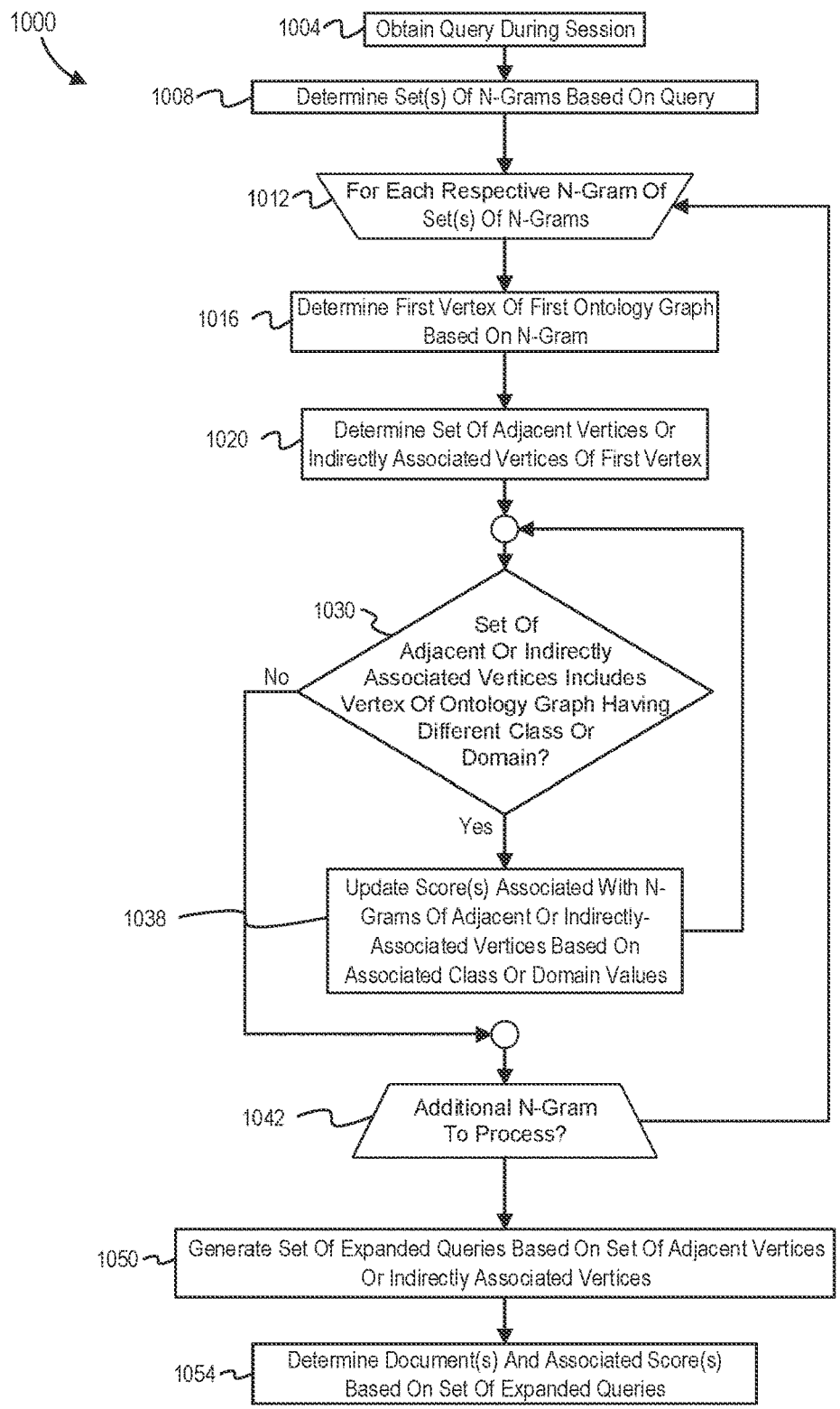
FIG. 10 is a flowchart of an example process by which a query may be expanded based on a set of ontology graphs, in accordance with some embodiments of the present techniques.

FIG. 10 is a flowchart of an example process by which a query may be expanded based on a set of ontology graphs, in accordance with some embodiments of the present techniques. Operations of the process 1000 may begin at block 1004. In some embodiments, the process 1000 may include obtaining a query during a session, as indicated by block 1004. Some embodiments may obtain a query using one or more operations described above for block 404. For example, some embodiments may obtain a query may by receiving a query from a user via a client computing device, where the user may be logged into an account during a data session. For example, a user may be using a native application, a web application executing in the context of a web browser, or other application that permits the user to log into a user account with a username and a password. The user account may store or otherwise be associated with a set of parameters, such as an indicated expertise score or other value associated with a class of documents, a set of domains, or the like. The account may also store or include links to a history of retrieved documents, feedback messages or indicators from the user indicating the relevance of documents, a set of previously-entered queries, age, ethnicity, geographic location, or the like. As described further below, some embodiments may use account parameters to determine the relevance of a set of retrieved documents or a set of expanded queries generated from an initial query.

In some embodiments, the process 1000 may include determining a set of n-grams based on the query, as indicated by block 1008. Some embodiments may determine a set of n-grams using one or more operations described above for block 408. For example, some embodiments may determine that each word of the query may be used as an n-gram, where one or more of the words may be modified or deleted based on a set of filters that remove stop words, lemmatizes words, stems words, or the like. Alternatively, or in addition, some embodiments may determine an n-gram as a phrase that includes multiple words, a syllable, a combination of words and punctuation, or the like. For example, some embodiments may determine that the phrase "valvular atrial fibrillation" is an n-gram.

Some embodiments may store past queries and their corresponding results while receiving a new query. Some embodiments may then determine a query matching score based on the n-grams of the past queries and the n-grams the new query. For example, some embodiments may determine that a first query and a second query are 90% identical with respect to a shared number of n-grams, where the documents retrieved using the first query are still stored in a record of past searches. Some embodiments may determine whether the query matching score satisfies a query matching threshold and, if so, retrieve the list of previously-retrieved documents of the first query in response to receiving the second query.

In some embodiments, the process 1000 may include performing one or more operations described below for blocks 1016, 1020, 1024, 1030, 1038, or 1042 for one or more respective n-grams of the set of n-grams determined above, as indicated by block 1012. Some embodiments may perform one or more of the operations for each n-gram of the set of n-grams. Alternatively, some embodiments may perform one or more of the operations for a subset of n-grams of the set of n-grams, where the operations may be terminated before all of the n-grams are processed after a determination is made that a terminal state or a process-terminating condition has been satisfied.

In some embodiments, the process 1000 may include determining a first vertex of a first ontology graph based on the respective n-gram, as indicated for block 1016. Some embodiments may determine the first ontology graph based on an index constructed from the ontology graph, a reference table indicating ontology graphs or vertices of ontology graphs associated with the n-gram, a set of records representing the first ontology graph or part of the first ontology graph, or the like. For example, some embodiments may determine that an index constructed from a first ontology graph includes the respective n-gram, where the respective n-gram is linked to or otherwise associated with a vertex identifier of the first ontology graph. As described above, some embodiments may determine a vertex of the ontology graph by first determining a learned representation of an n-gram and then determining a vertex associated with the learned representation.

Some embodiments may determine that an n-gram is mapped to multiple learned representations and return a corresponding multiple number of vertices for one or more ontology graphs. Some embodiments may assign an associated context-matching score to the learned representations or corresponding vertices indicating a likelihood of relevance using a statistical model or machine learning model. For example, some embodiments may use a machine learning model that includes a neural network that uses one or more parameters of a user account as an input to determine a context-matching score for an n-gram that indicates a predicted relevance of a vector or other learned representation of the n-gram. As discussed further below, some embodiments may construct a plurality of expanded queries, where each vector is used at least once by at least one expanded query of the plurality of expanded queries.

In some embodiments, the process 1000 may include determining a set of adjacent vertices or indirectly associated vertices of the first vertex, as indicated for block 1020. Some embodiments may determine the set of adjacent vertices using an index, such as an index constructed from or otherwise based on an ontology graph. For example, an index may be updated to include an association between an identifier of the first vertex and an identifier of a second vertex, where the association may be encoded as a set of connected index nodes of a B-tree structure. In some embodiments, the encoded association of an index may represent an edge associating the first vertex and the second vertex in an ontology graph. Some embodiments may determine a plurality of adjacent vertices of the first vertex, where one or more of the operations described in this disclosure for adjacent vertices may be performed for each adjacent vertex of the plurality of adjacent vertices. Some embodiments may further determine differences in class value between a first vertex or its corresponding first n-gram and a second vertex or its corresponding second n-gram based on the difference in class values stored in the index. As further described below, using data stored in or otherwise associated with an index indicating class value may increase the efficiency and semantic accuracy of a semantic search based on a query.

Some embodiments may determine a set of indirectly associated vertices of a first vertex by crawling through the edges associated with the vertices, where the edges may include ontology graph edges of a shared ontology graph or ontology graph edges that cross ontology graphs and connect vertices from different ontology graphs. For example, a first vertex of a first ontology graph may be associated with a second vertex of the first ontology graph, and the second vertex may be associated with a third vertex of a second ontology graph via a cross-graph edge, where the third vertex may be indirectly associated with the first vertex with an ontology graph edge distance equal to two. As further described elsewhere in this disclosure, some embodiments may assign one or more criteria to the graph edges it is permitted to use when determining a set of adjacent or indirectly associated vertices.

Some embodiments may determine a set of indirectly associated vertices of the first vertex based on a maximum ontology graph edge distance from the vertex. For example, some embodiments may obtain all the vertices of a set of ontology graphs that are associated with a first vertex by three or less ontology graph edges. Alternatively, or in addition, some embodiments may determine the set of indirectly-associated vertices using a criteria based on one or more categories associated with the edges of the vertices. For example, some embodiments may determine a set of indirectly associated vertices of the first vertex based on the indirectly-associated vertices being labeled as either a subset of a first concept associated with the first vertex or a lower class concept of the first concept of a first ontology graph. In some embodiments, a lesser class concept of a first concept may be a concept of a second ontology graph, the second ontology graph having a lesser class value than the first ontology graph.

In some embodiments, the process 1000 may include determining whether the set of adjacent vertices or indirectly associated vertices include vertices of an ontology graph having a different class or domain, as indicated by block 1030. As described above, the adjacent or indirectly-associated vertices of a first vertex may include one or more vertices of another ontology graph that is associated with the n-gram. For example, the first vertex may represent a first concept of a first ontology graph that is associated with a second concept of a second ontology graph, where class values of the respective ontology graphs may be used to organize the concepts into a hierarchical set of concepts. In some embodiments, the association between the first and second ontology graphs may be available based on a cross-graph association between the first vertex or an adjacent vertex of the first vertex with one or more vertices of a second ontology graph. As disclosed elsewhere in this disclosure, the second ontology graph may differ from the first ontology graph with respect to a domain or class of knowledge. If a determination is made that the set of adjacent vertices or indirectly associated vertices include vertices of an ontology graph having a different class or domain, some embodiments may proceed to operations described for block 1038. Otherwise, operations may proceed to operations described for block 1042.

In some embodiments, the process 1000 may include updating a set of scores associated with the n-grams of the adjacent or indirectly-associated vertices based the associated class or domain values, as indicated by block 1038. For example, some embodiments may determine a set of n-gram weights associated with each n-gram based on a shared domain or class with respect to a user account. Using the convention that a greater n-gram weight results in a greater prioritization of the corresponding n-gram for use in generating an expanded query, as further described below, some embodiments may increase the n-gram weight of an n-gram of an adjacent or indirectly associated vertex. For example, some embodiments may increase an n-gram weight for an n-gram based on the n-gram being associated with a vertex sharing a class value with a class value indicated by a user account. Alternatively, or in addition, some embodiments may increase or decrease an n-gram score based the number of ontology graph edges between a first n-gram and a second n-gram. Furthermore, some embodiments may reduce the cost of an n-gram weight for a second n-gram with respect to a first n-gram based on one or more values stored in an index associating the second n-gram with the first n-gram. It should be understood that some embodiments may instead rank weights of an n-gram such that a lesser weight results in a greater prioritization and reduce a weight instead of increasing the weight to increase the prioritization of a corresponding n-gram.

In some embodiments, the process 1000 may include determining whether an additional n-gram of the query should be processed using one or more of the operations described above, as indicated by block 1042. Some embodiments may process each of the n-grams of a query for example, some embodiments may obtain the initial query "what do babies eat," use each of the words of the initial query as an n-gram of the query, and perform one or more of the operations described above for each of the n-grams "what," "do," "babies," and "eat." Alternatively, or in addition, some embodiments may process a subset of the n-grams of a query. For example, some embodiments may obtain a query "a very depressing people" and apply a set of filtering operations such as lemmatizing, stopword removal, and stemming to produce a filtered query having the n-grams "very," "depress," and "people." Some embodiments may then determine that the n-gram "very" is a low-priority n-gram or is not part of any ontology graphs that the user has permission to access and, in response, use the n-grams "depress" and "people" as part of a query.

Some embodiments may generate a set of expanded queries based on the set of vertices described above, as indicated by block 1050. An expanded query of an initial query may include n-grams from the initial query and n-grams associated with one or more of the vertices described above. For example, after receiving a first expanded query, "BMS-56 D. in aFib pts with VTE," some embodiments may generate a first expanded query that includes the n-grams "BMS-56," "D.," "aFib," and "pts." the first expanded query may also include the n-gram "DVT," where the n-gram "acute venous thromboembolism" may be associated with a vertex that is adjacent to a vertex representing the n-gram "VTE."

Some embodiments may prioritize use of n-grams having greater n-gram weights. For example, if the n-grams "Acute Venous Thrombosis" and the "DVT" have n-gram weights of 30 and 70 with respect to the n-gram "VTE," some embodiments may prioritize the generation of an expanded query using the n-gram "DVT" over the generation of an expanded query using the n-gram "Acute Venous Thrombosis." Alternatively, or in addition, some embodiments may rank a first query or semantic search results of the first query with a lesser score than a second query or semantic search results of the second query in response to the first query using a n-gram having a lesser n-gram weight.

Some embodiments may use one or more machine learning operations to generate one or more expanded queries. For example, as described elsewhere in this disclosure, some embodiments may use an abstractive text summarization model or other natural language processing model to generate an expanded query based on the model. Some embodiments may use a pre-trained neural network, such as a neural network of a generative pre-trained transformer (GPT) language model or a neural network of a bi-directional encoder-decoder model, to generate an expanded query, where the neural network may use a subset of the n-grams of an initially-obtained query. For example, some embodiments may use a transformer neural network to determine a set of embedding vectors for a set of n-grams of a query using a set of encoder neural network layers of the transformer neural network. As described elsewhere in this disclosure, in some embodiments, the encoder neural network layers may have three or less neural network layers. Some embodiments may then determine a set of positional encoding vectors, where each positional encoding vector may be determined based on a position of a respective n-gram in the selected set of n-grams. Some embodiments may then generate a plurality of random feature maps based on the set of embedding vectors using one or more feature map functions. For example, some embodiments may use a feature map function based on the set of embedding vectors comprises generating a set of random or pseudorandom variables and multiplying at least one variable of the set of random or pseudorandom variables with the at least one element of the set of embedding vectors.

As described elsewhere in this disclosure, some embodiments may use a transformer neural network model that includes one or more attention mechanisms to generate a query or other text. For example, some embodiments may use a transformer neural network that includes determining a set of attention values and using the attention values to generate or update a query. After receiving a user-provided query, some embodiments may determine a set of embedding vectors based on the n-grams of the user-provided query using the transformer neural network. For example, some embodiments may determine embedding vectors for the n-grams of the query using an encoder neural network having three or fewer neural network layers, where having a lesser number of neural network layers may reduce the computation required to generate text. Some embodiments may then generate a first random feature map based on the set of embedding vectors using a feature map function. In some embodiments, using the feature map function may include generating a first set of random or pseudorandom variables and multiplying at least one variable of the first set of random or pseudorandom variables with the at least one element of the set of embedding vectors.

Some embodiments may then determine a set of positional encoding vectors that indicate a position of an n-gram with respect other n-grams and use the positional encoding vectors as additional inputs of a neural network. For example, some embodiments may generate a second random feature map based on the set of positional encoding vectors using another feature map function, where using the random feature map includes multiplying at least one variable of a set of random or pseudorandom variables with the at least one element of the set of positional encoding vectors. Some embodiments may then determine a set of attention values based on the first random feature map and the second random feature map, such as by performing a set of element-wise matrix operations. Some embodiments may then generate an expanded query using the neural network based on the set of attention values. For example, some embodiments may use a neural network having neural network layers that use one or more of the set of attention values as inputs to determine additional n-grams for an expanded query or to determine new n-grams for use as substitute n-grams for n-grams of a user-provided query.

Some embodiments may determine the set of documents or set of associated scores based on the set of expanded queries as indicated by block 1054. Some embodiments may perform one or more of the operations described above for block 420 to retrieve a set of documents or set of associated scores based on a query. For example, some embodiments may obtain an index constructed from or otherwise updated with data from one or more of the ontology graphs described above. The index may include a set of lists, arrays, or other elements that link or otherwise associate n-grams to documents. For example, the index may include an array associating a first and second identifier.

As described elsewhere in this disclosure, some embodiments may determine a score for a document based on data stored in the document and a set of account parameters. For example, if a user having an account indicating a class value provides a query, some embodiments may increase a relevance score of a retrieved document if the retrieved document is also labeled with the same class value. Some embodiments may update parameters of a scoring function used to determine a relevance score. For example, after displaying a plurality of expanded queries that includes a first query having a greatest relevance score and a second query having a relevance score less than that of the first query, some embodiments may receive feedback indicating that an expanded query is a preferred query. In response, some embodiments may update an n-gram weight associated with a third n-gram of the second expanded query, where the n-gram weight may be a parameter of a scoring function used to generate or rank at least one query of the plurality of expanded queries, and where the first expanded query does not include the third n-gram. By updating the n-gram weight or some other parameter used to generate the plurality of expanded queries, some embodiments may increase the accuracy of an expanded query or its corresponding search result(s).

Figure 11:
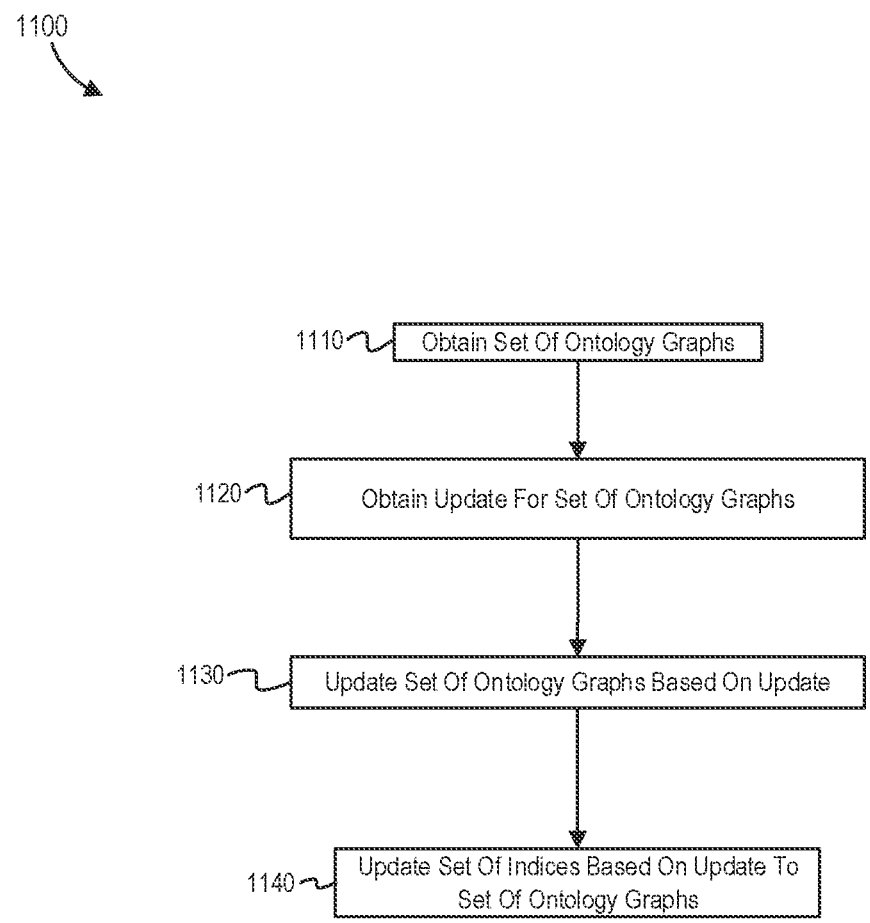
FIG. 11 is a flowchart of an example process by which a hierarchical set of ontologies may be updated, in accordance with some embodiments of the present techniques.

FIG. 11 is a flowchart of an example process by which a hierarchical set of ontologies may be updated, in accordance with some embodiments of the present techniques. Operations of the process 1100 may begin at block 1110. In some embodiments, the process 1100 may include obtaining a set of ontology graphs, as indicated by block 1110. In some embodiments, the set of ontology graphs may be constructed using operations similar to or the same as those described above. For example, some embodiments may obtain a first ontology graph categorized as being part of a first domain and a first class value, a second ontology graph categorized as being part of the first domain and a second class value, and a third ontology graph categorized as being part of a second domain and a third class value.

In some embodiments, the process 1100 may include obtaining an update for the set of ontology graphs, as indicated by block 1120. In some embodiments, an update may be obtained from a computing device executing one or more operations described in this disclosure. Alternatively, or in addition, an update may be obtained from a third-party computing system and received at an application program interface of a server executing one or more operations described in this disclosure.

Some embodiments may obtain an update from an interaction with a UI. For example, some embodiments may send program code to a native application, web browser, or other application executing on a computing device that causes a display screen to show a UI. The UI may include interactive elements that allows a user to form connection lines or other connecting shapes between visualizations that represent concepts or other vertices of an ontology graph. After determining that the interaction with the UI element connects a first and second concept (or two other vertices of an ontology), some embodiments may send a message from the computing device indicating the association the first concept and the second concept. Additionally, in some embodiments, the UI may include program code that stores a set of rules or other conditions.

In some embodiments, after determining that an interaction with a UI would update a hierarchical set of graphs, some embodiments may verify whether one or more of the set of rules or other conditions would be violated. Various conditions may be applied and tested, such as a condition that restrict vertices of a first type from being associated with vertices of a second type, a condition that restricts n-grams associated with a first concept from being associated with a second concept, a condition that restricts vertices associated with a first class value from being associated with vertices having a different class value without an appropriate user authorization, or the like. For example, some embodiments may include a condition that a user logged in via a user account must have an appropriate permission value before being permitted to edit a connection between a first vertex representing a first concept and a second vertex representing a second concept. In response to a determination that a rule would be violated by a proposed connection between vertices, a verification element of the UI may change text or appearance (e.g., change a color, shape, size, or the like) to indicate that the rule would be violated by the proposed connection other proposed update to a set of ontology graphs.

In some embodiments, the UI may include additional UI elements to update other operations described in this disclosure. For example, an interaction with a UI element may re-arrange blocks representing workflow operations such as document ingestion, learned representation generation, other NLP operations, other machine learning operations, ontology modification, or the like. Some embodiments may provide a UI that permits a user to update a workflow block representing one or more workflow operations to indicate a machine learning model, parameters of the machine learning model, a set of ontology graphs to update, or the like. For example, some embodiments may provide a UI that permits a user to add workflow blocks to a set of workflow blocks, remove workflow blocks from the set of workflow blocks, reconfigure workflow blocks of the set of workflow blocks, or otherwise update the set of workflow blocks. In response to a change to the set of workflow blocks, some embodiments may update a compiled version of a program code implementing a set of operations represented by the set of the workflow blocks.

In some embodiments, the process 1100 may include updating a set of ontology graphs based on the update, as indicated by block 1130. Updating a set of ontology graphs may include updating edges connecting vertices of the same or different ontology graphs, updating n-grams or word embeddings associated with the edges, updating documents associated with the vertices, or the like. In some embodiments, new ontology graph edges may be constructed to associated different vertices of an ontology graph based on associations with vertices of a second ontology graph, where the associations with the second ontology graph may be caused by an update message. For example, a first ontology graph associated with a first domain and class may include a first vertex mapped to a first n-gram. The first vertex may be associated with a first embedding vector of the first n-gram, where the first embedding vector is a vector of a first cluster. The first cluster may represent a first concept that is mapped to a second n-gram and a corresponding second vertex, where the second n-gram may represent a centroid of the first cluster or a manually-entered label for the first cluster. Similarly, a second ontology graph associated with a second domain or class may include a third vertex mapped to a third n-gram. The third vertex may be associated with a second embedding vector of the third n-gram, where the second embedding vector is a vector of a second cluster. The second cluster may represent a second concept that is mapped to a fourth n-gram and a corresponding fourth vertex, where the fourth n-gram may represent a centroid of the second cluster or a manually-entered label for the second cluster.

Some embodiments may obtain instructions to associate the first concept and the second concept. For example, some embodiments may associate a pair of concepts to each other based on a shared set of n-grams, a shared set of documents, a user-entered association, or the like. The concepts may be associated to each other via an association between n-grams representing the concepts, an association between embedding vectors representing the concepts, an association between vertices of a set of ontology graphs representing the concepts, or the like. In response to the association between the concepts, some embodiments may construct an edge between the first n-gram and the third n-gram based on a first edge associating the first n-gram with the second n-gram, a second edge associating the second n-gram with the fourth n-gram, and a third edge associating the fourth n-gram with the fourth n-gram.

Some embodiments may receive an update comprising instructions to associate the first cluster and the second cluster based on a shared set of n-grams, a shared set of documents, a user-entered association, or the like. In response, some embodiments may generate an ontological graph edge between the first n-gram and the third n-gram based on a first edge associating the first n-gram with the second n-gram, a second edge associating the second n-gram with the fourth n-gram, and a third edge associating the fourth n-gram with the fourth n-gram. Some embodiments may generate the ontological graph edge by generating an ontological triple comprising identifiers for a vertex representing the first n-gram and the second n-gram and storing the ontological triple in a database of ontological triples.

In some embodiments, obtaining the update may include obtaining a request to associate a first element of a set of ontology graphs with another element of the set of ontology graphs, where the element may include a vertex of an ontology graph, a concept, an n-gram associated the vertex, or the like. For example, a user may type in a data entry indicating that the n-gram "heart attack" is associated with the concept "cardiovascular emergency." In some embodiments, the update may be associated with a given domain based on a domain or other domain category value assigned to a user providing the update. For example, the update may be associated with the domain of knowledge "neurology" based on a determination that the update provider's associated domains include the domain "neurology."

Some embodiments may select one or more associated ontologies to which the update is applicable based on one or more domain category values associated with the update. For example, after receiving an update request associated with a first domain of knowledge associated with a first ontology graph, class value within the first domain of knowledge, or other domain category value, some embodiments may select a second ontology graph from amongst a plurality of ontology graphs as also being an applicable ontology graph with respect to the update request. The selection of the second ontology graph may be based on a determination that the first and second ontology graphs are related based on the domain category value. For example, some embodiments may select the second ontology graph based on a determination that the first and second ontology graphs share a domain category value, such as both first and second ontology graphs sharing the domain category "medicine" and differing with respect to their corresponding class values.

Alternatively, or in addition, some embodiments may select one or more ontology graphs based on their respective domain category distance(s). A domain category distance may include a distance (e.g., Manhattan distance, Euclidean distance, or the like) in a domain category value space. For example, if a domain category distance is calculated using a Manhattan distance, the domain category distance between a first ontology graph and a second ontology graph may be equal to the difference between their respective class values. Some embodiments may then determine whether two ontologies are associated with each other based on whether the domain category distance satisfies a distance threshold. Alternatively, or in addition, some embodiments may determine the domain category distance for an ontology graph based on differences between a domain category value (e.g, a class value) of the ontology graph and an account parameter of the user account used to provide an update. In some embodiments, if the domain category distance satisfies a distance threshold, the corresponding ontology graph may be selected, and if the domain category distance does not satisfy the distance threshold, the corresponding ontology graph may not be selected.

Alternatively, or in addition, some embodiments may select an ontology graph based on whether or not a provider of the update is associated with the ontology graph via the user account of the update provider. For example, some embodiments may select a second ontology graph based on a determination that an identifier for the second ontology graph is an element of an array stored in a user account of the update provider. In some embodiments, the array may indicate the domains of knowledge that the provider is indicated to have expertise in, may indicate class values for one or more domains of knowledge, or may include other domain category values. In some embodiments, satisfying a domain threshold for updating an ontology graph may include satisfying a requirement that the user account lists the identifier of the ontology graph. Alternatively, or in addition, satisfying the domain threshold may include satisfying a requirement that the user account lists a quantitative score (e.g., an expertise score) for the corresponding domain that satisfies a quantitative threshold (e.g., greater than one).

Some embodiments may search through a set of selected ontology graphs for concepts or other vertices related to the first vertex. For example, after receiving an update indicating an association between an n-gram and a first concept, some embodiments may determine a first vertex associated with the n-gram by generating an embedding vector based on the n-gram and determining a first vertex mapped to the embedding vector. Some embodiments may then determine whether the first concept is associated with a second concept via a cross-graph edge that is indicated to permit an association between n-gram and the second concept.

Some embodiments may determine that an n-gram (or a vertex representing the n-gram) may be associated with a concept of a different ontology graph in response to their associated edges or the vertices between them satisfying one or more criteria based on one or more relationship types. As discussed elsewhere in this disclosure, a relationship type may be represented by a category or combination of categories associated with a graph edge(s) between two or more vertices and may indicate various relationships between n-grams or other elements represented by vertices. For example, a relationship type may indicate that a first n-gram is a subclass of a concept, is a symptom of a concept, is a cause of a concept, is equivalent to a concept, or the like. Some embodiments may then determine that two vertices or values they represent (e.g., n-grams, concepts, or the like) may be associated based on a determination that the edges between them are of the same type. For example, some embodiments may determine that a first vertex representing an update-provided n-gram is associated via first graph edge to a second vertex representing the first concept, where the first graph edge indicates that the first vertex is a subtype of the second vertex. Additionally, the second vertex may be associated with a third vertex representing a second concept, where the third vertex is a vertex of a second ontology graph, and where the second graph edge associating the second and third vertices indicate that the second graph edge indicates that the second vertex is a subtype of the third vertex. In response, some embodiments may determine that the first vertex and third vertex may be associated, where such association may be performed by associating one or more values of the first vertex with one or more values of the third vertex. For example, some embodiments may associate an n-gram represented by the first vertex with a concept of the third vertex.

Once a determination is made that a relationship criterion is satisfied and that a first n-gram mapped to a first vertex of a first ontology graph may be associated with a concept of a different ontology graph, some embodiments may then associate the first n-gram with an n-gram of the concept. For example, if the concept is directly mapped to a second vertex or second n-gram of the second vertex, some embodiments may then associate the first n-gram with the second n-gram representing the concept. Alternatively, or in addition, a third n-gram may be associated with a fourth vertex that is associated with the second vertex, and some embodiments may then associate the first n-gram with the third n-gram.

Some embodiments may update a set of indices based on updates to the set of ontology graphs, as indicated by block 1140. Operations to update an index may include one or more operations described above for block 340. For example, some embodiments may update an index to associate a first n-gram directly with a second n-gram in the index. Some embodiments may update an index that is structured in the form of a B-tree, where a key value corresponding to the first n-gram is stored in a parent node of the index and may be associated with a second n-gram via a leaf node of the parent node. Alternatively, or in addition, some embodiments may update an index to associate a first n-gram with a document associated with the second n-gram.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 500 may be transmitted to computer system 500 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

Figure 12:
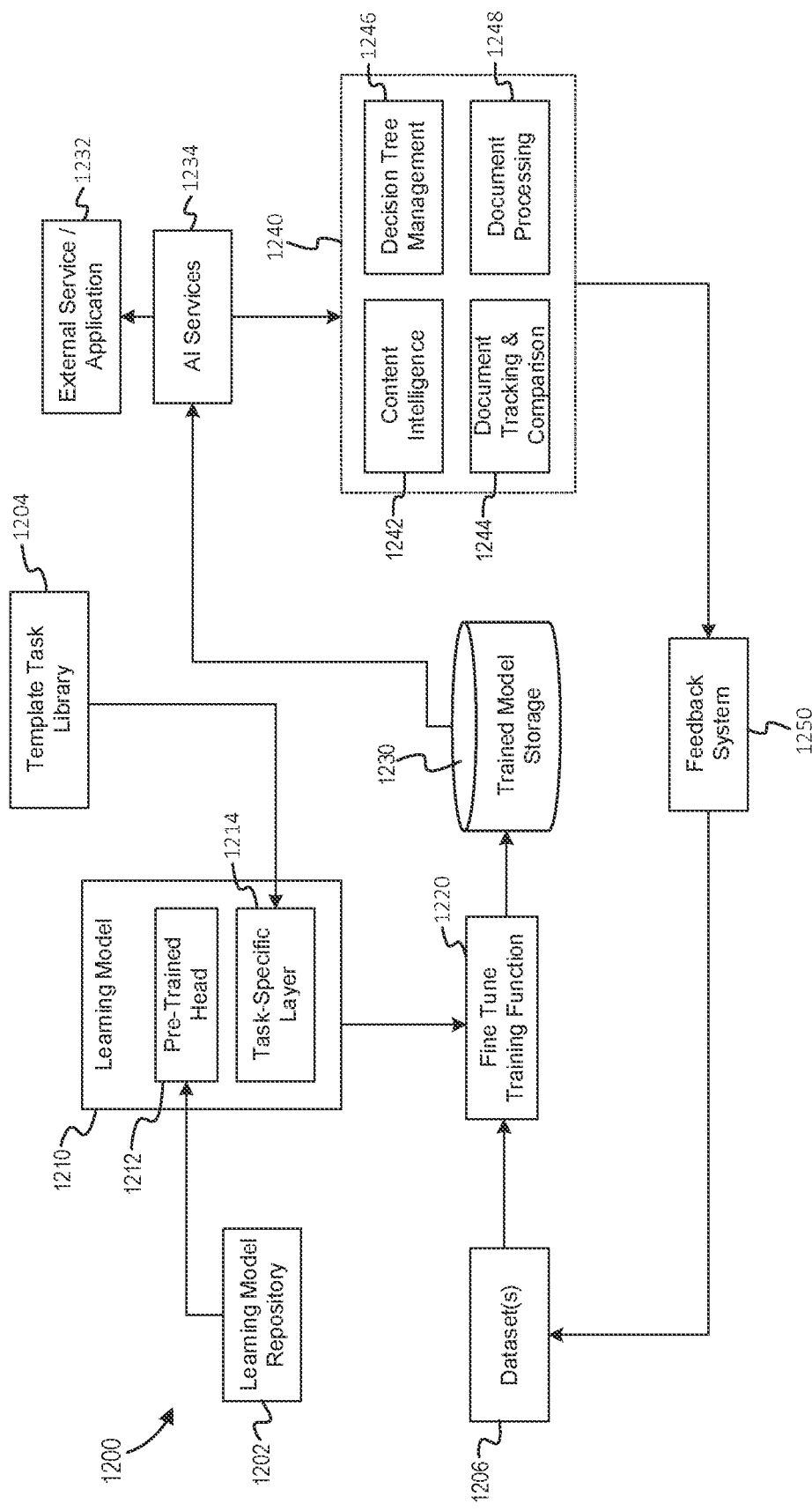
FIG. 12 is a logical architecture indicating the integration of a data system with one or more learning systems, in accordance with some embodiments of the present techniques.

FIG. 12 is a logical architecture indicating the integration of a data system with one or more learning systems, in accordance with some embodiments of the present techniques. The logical architecture 1200 includes a learning model repository 1202 that may be accessed to provide an initial pre-trained head 1212 of a learning model 1210, where the pre-trained head 1212 may include a first set of neural network layers, a first set of ontology graphs, model hyperparameters, or the like. The learning model repository 1202 may include parameters and functions corresponding to one or more types of learning models, such as BERT, BioBERT, GPT-3, USE, RoBERTa, ELMo, T5, EXLNet, BART, or the like. For example, the learning model repository 1202 may include scripts or program code usable for executing instances of a learning model and a set of neural network parameters such as weights, biases, activation thresholds, activation function parameters, or the like.

Some embodiments may perform transfer learning operations to provide the pre-trained head 1212 of the learning model 1210. Some embodiments may then use the initial set of parameters of the pre-trained head 1212 to generate an initial output that is usable as an input for a set of task-specific layers 1214 during the training of the learning model 1210, where some embodiments may use hierarchical ontologies to generate the initial output. The initial output may include categories or a set of embedding vectors corresponding to training inputs that are then used by the set of task-specific layers 1214.

The set of task-specific layers 1214 may include a second set of neural network parameters that are updated with a set of training operations to perform various tasks. In some embodiments, the set of training operations may use parameters obtained from a template task library 1204 to update parameters of the set of task-specific layers 1214. The template task library 1204 may include training task parameters such as a training dataset for tasks such as summarization, text classification, language modeling, named entry recognition, text encoding, ontology lookup, natural language generation, question-answering, text representation, or the like. For example, some embodiments may train the learning model 1210 by importing neural network parameters from the template task library 1204 into a set of neural network layers of the set of task-specific layers 1214 and use a first training dataset of the template task library 1204 to train the modified learning model 1210.

In some embodiments, the learning model 1210 may include or otherwise access a set of ontology graphs, such as ontology graphs obtained from the learning model repository 1202 or a data store used store ontology graphs. For example, the learning model 1210 may access a graph database to import a set of ontology graphs corresponding with different domains or domain levels, such as those described in this disclosure. Some embodiments may use these ontology graphs to perform one or more tasks described in this disclosure. For example, some embodiments may perform named entity recognition to recognize a set of words as a named entity, assign a first category value of a first ontology graph to the named entity, and assign a second category value of a second ontology graph to the same named entity.

After generating or updating the learning model 1210, some embodiments may perform a set of fine-tuning operations represented by the fine tune training function 1220, where the fine tune training function 1220 may apply data from dataset(s) 1206. The dataset(s) 1206 may include publicly available "open" datasets, data specific to an account or organization, additional annotations on a document (e.g., user-entered classifications or named entities), or the like. where the fine tune training function 1220 may be limited to updating a subset of the parameters of the learning model 1210. For example, some embodiments may update the set of task-specific layers 1214 with a first dataset of the template task library 1204 by updating parameters of three neural network layers of the set of task-specific layers 1214 and then updating parameters of only two neural networks of the set of task-specific layers 1214 with the fine tune training function based on the dataset(s) 1206. Alternatively, some embodiments use additional training operations based on the dataset(s) 1206 to update some or all of the parameters of the set of task-specific layers 1214 or some or all of the parameters of the learning model 1210. For example, some embodiments may update a set of ontology graphs to indicate new associations between different concepts encoded in the set of ontology graphs, add new vertices representing a new concept with its corresponding n-gram, or otherwise update the set of ontology graphs. Some embodiments may store parameters of the learning model 1210 in the trained model storage 1230 after performing one or more of the training operations described above.

Some embodiments may access the trained model storage 1230 when providing artificial intelligence (AI) services for tasks described in the utility set 1240. In some embodiments, the AI services may include stateless API services that provide access to one or more trained models described in this disclosure. The operations of the utility set 1240 may include a content intelligence operation 1242, a decision tree management operation 1246, a document tracking and comparison operation 1244, a document processing operation 1248, a parameter-tracking operation, or other operations described in this disclosure. For example, some embodiments may use the model and model parameters of the trained model storage 1230 to generate summarizations of texts, generate queries for indexing operations, or the like, as described elsewhere in this disclosure.

Some embodiments may present the results of the AI services 1234 to a UI that includes UI elements enabling a user to provide feedback. For example, some embodiments may display a generated text to a user in a UI. The user may click on a word of the UI and select one or more domains or domain level that should be assigned to the word, where the selection of the word, domains, or domain levels may be sent in a message to a feedback system 1250. The feedback system 1250 may then update the dataset(s) 1206 to include the user-updated assignment of the word to the domains or domain levels, which may also cause the fine tune training function 1220 to update the parameters of the learning model 1210. For example, some embodiments may update a set of named entity recognition operations based on the updated feedback, where the set of named entity recognition operations may be used in a document comparison operation.

As discussed elsewhere in this disclosure, some embodiments may detect changes in concepts or other categories assigned to a word, name, phrase, or other n-grams across different documents or different versions of a document. For example, some embodiments may determine that the concept represented by the n-gram "burger" is associated with a first set of other concepts including the concepts represented by the n-grams "sandwich" and "lunch" based on the text of a first set of documents. Some embodiments may then determine that the concept represented by the n-gram "burger" is associated with another concept represented by the n-gram "vegan" based on a second set of documents, where the second set of documents may have been authored or obtained at a different time than the first set of documents and update the corresponding ontology graph(s) to indicate the association between the concept represented by "burger" and the concept represented by "vegan."

Various criteria may be used to determine associations between concepts or other elements representable by n-grams. For example, after first recognizing that two different n-grams represent two different named entities, some embodiments may determine that the two different named entities are associated with each other based on a determination that the frequency by which two corresponding n-grams are in the same sentence together across multiple documents is greater than a frequency threshold. Alternatively, or in addition, some embodiments may determine that the two named entities are associated with each other based on a determination that the embedding vectors corresponding to the pair of named entities are sufficiently close to each other in the embedding space of the embedding vectors. Some embodiments may further use additional words or corresponding embedding vectors to determine a hierarchical relationship between the two named entities or may use the ontology graphs themselves to determine the hierarchical relationship. For example, some embodiments may determine that the n-gram "veggie burger" is a subset of the n-gram "burger" in an ontology graph based on previous graph edges of the n-gram "veggie burger" and the n-gram "burger."

Some embodiments may update a set of ontology graphs to indicate that a first n-gram is associated with a second n-gram in either the same domain category or across different domain categories. For example, in an initial generation of a first ontology graph labeled with the domain category "video games" and a second ontology graph labeled with the domain category "health activities," some embodiments may determine that no associations exist between the two ontology graphs. After obtaining a second set of documents, some embodiments may determine that a first n-gram "VR rhythm game" encoded in the first ontology graph is associated with a second n-gram "cardiovascular exercise," where the first n-gram is encoded in a vertex of the first ontology graph and the second n-gram is encoded in a vertex of the second ontology graph. In response, some embodiments may update the first and second ontology graphs to indicate the detected association, where this detected association may then be used for natural language processing operations or other operations described in this disclosure. For example, some embodiments may update a set of query generation operations or update a set of categories that are presented in a UI to indicate a detected association between a first n-gram and a second n-gram.

III. Ontology Integration for Summarization

Summarizations of text documents may be used to provide useful information in time-critical scenarios. Additionally, summarizations provide the practical benefit of reducing cognitive load on users during a search operation through natural-language text by providing users with relevant information that helps them determine which documents to analyze and which documents to ignore. However, summarization operations that do not consider a user's areas of expertise may provide an inappropriate amount of information for a user. For example, a summary that uses jargon or technical terminology outside of a user's area(s) of expertise may be technically relevant but practically inadequate for the goal of providing a user with the information they need to determine if a document should be read or otherwise used. Without adequate consideration for a user's domains, domain classes, or other domain category station values, some embodiments may provide document summaries that are either too simplistic or too technical for a user to interpret.

Some embodiments may use associations between different ontologies as described above to generate text summaries using extractive or abstractive text summarization methods. Some embodiments may use the associations between different ontologies to generate summarizations of text or other data stored in corpora of text. After obtaining a query from a user and a set of context parameters associated with the user, some embodiments may retrieve a natural language document using one or more operations described elsewhere in this disclosure. Some embodiments may then generate a text summarization of the retrieved document(s) based on n-grams of the document(s) associated with one or more ontologies. Some embodiments may use indices, ontologies, or another set of associations relating n-grams of one domain category value with n-grams of another domain category value to generate a text summary. For example, some embodiments may use an index to directly determine which n-grams of one domain class found in a query may map to an n-gram of another domain class, where the index may be generated from associations of different ontologies. Alternatively, or in addition, some embodiments may traverse edges of different ontology graphs to select n-grams of a first ontology graph based on n-grams of a second ontology graph.

By generating summaries using ontologies associated with domains or categories of domains, some embodiments may provide more domain-specific text summarizations. Incorporating domain-specific ontologies to generate summarization may result in the generation of more meaningful or interpretable summarizations that are more likely to retrieve information relevant to a query. Additionally, some embodiments may use ontology-determined indices to increase the speed or efficiency of ontology-specific summarization generation.

Figure 13:
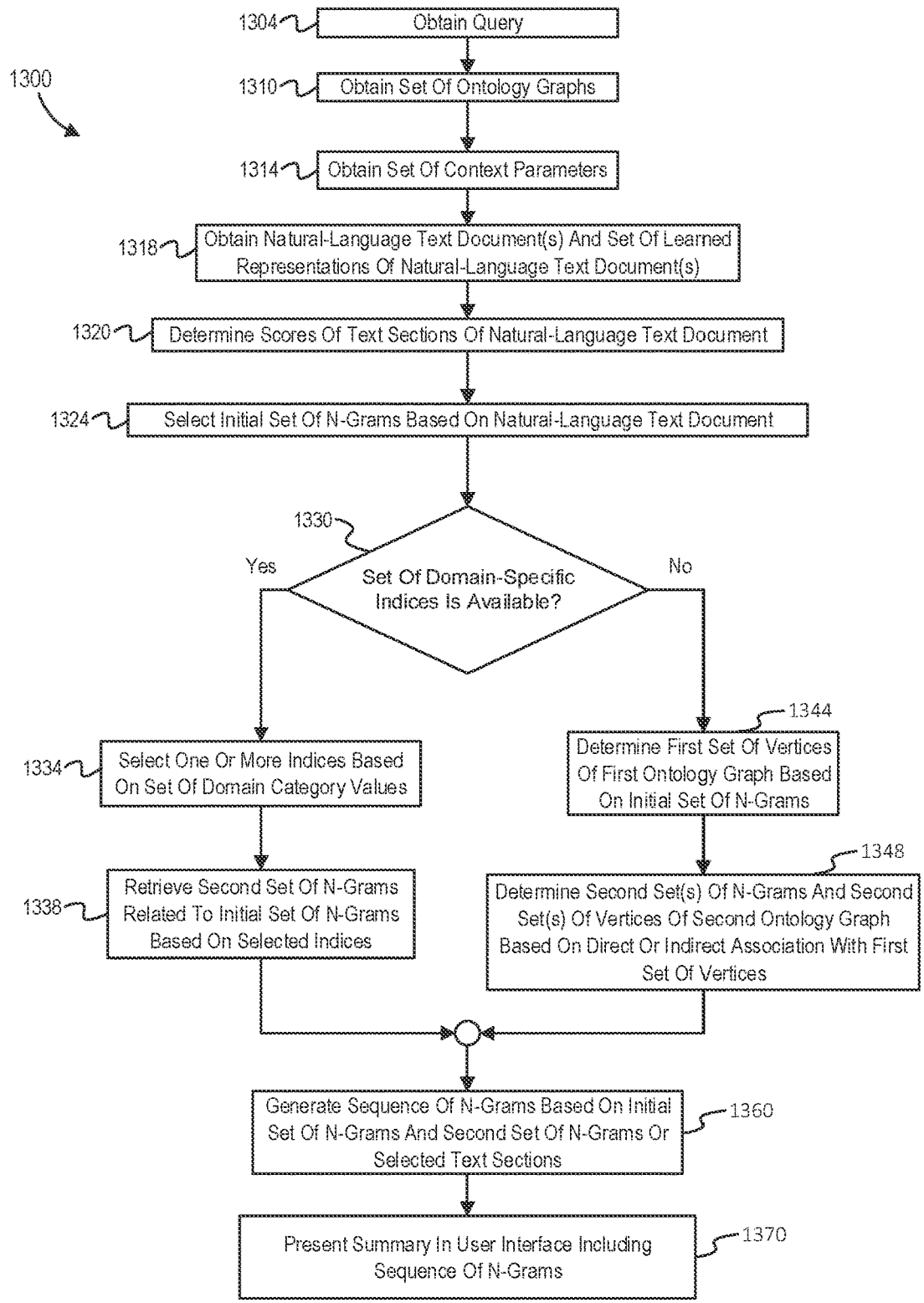
FIG. 13 is a flowchart of an example process by which a domain-specific summarization may be provided based on a query, in accordance with some embodiments of the present techniques.

FIG. 13 is a flowchart of an example process by which a domain-specific summarization may be provided based on a query, in accordance with some embodiments of the present techniques. In some embodiments, the process 1300 may include obtaining a query, as indicated by block 1304. The process of obtaining a query may include one or more operations described above, such as one or more operations described for block 404. For example, some embodiments may obtain a query during a login session between a client computing device and a server or other computer system, where a set of account parameters of a user account of the session may be available and included in a set of context parameters. Alternatively, or in addition, the query made by a user may be used to generate one or more predicted values that may be included in the set of context parameters.

In some embodiments, the process 1300 may include obtaining a set of ontology graphs, as indicated by block 1310. As described elsewhere, the set of ontology graphs may be stored in various forms and loaded into a computer system in various forms. For example, some embodiments may obtain a set of ontology graphs encoded in the form of a set of linked arrays and lists storing vertices and edges connecting the vertices together. As described elsewhere in this disclosure, in some embodiments, each respective vertex of a set of vertices of an ontology graph may be identified by or otherwise mapped to by a respective learned representation (e.g., a respective embedding vector in an embedding space) of an n-gram. Alternatively, in some embodiments, each respective vertex of a set of vertices of an ontology graph may be identified by or otherwise mapped to by a respective n-gram, directly. Some embodiments may include a plurality of ontology graphs, where each ontology graph is associated with a different domain of knowledge, a different domain class within the domain of knowledge, or other domain category values. For example, some embodiments may obtain a first ontology graph associated with a first domain of knowledge and a second ontology graph associated with a second domain of knowledge, where a vertex of the first ontology graph identifying an n-gram may map to a vertex of the second ontology graph via a cross-graph edge.

Some embodiments may load one or more ontology graphs from a persistent memory into a non-persistent memory based on a set of user-specific context parameters that indicates a domain, class within the domain, or another domain category value. For example, some embodiments may load a set of values representing a set of graph vertex identifiers, an array of edges associating different graph vertices of the ontology, or a set of vectors representing n-grams. Furthermore, some embodiments may convert a set of ontology graphs into an index storing pairs of n-grams that span between different ontology graphs. In some indices, a pair of n-grams may span between different ontology graphs if the first n-gram of the pair is part of a first ontology and the second n-gram of the pair is part of a second ontology. As described elsewhere in this disclosure, two ontology graphs may be stored as part of a same data structure or set of data structures, but be made distinct from each other based on their respective association with different domain category values.

Some embodiments may obtain preference weight(s) that are associated with an ontology, where a user may have different preference weights for different ontologies or classes within the ontologies. Some embodiments may then select one or more ontologies for use to select n-grams or generate summaries based on the preference weights. For example, a user may be indicated as being capable of accessing a first ontology graph associated with the domain "billing" and a second ontology graph associated with the domain "clothing." Some embodiments may select the second ontology graph without selecting the first ontology graph when performing one or more operations described in this disclosure for the user based on "clothing" having a greater preference weight.

In some embodiments, the process 1300 may include obtaining a set of context parameters, as indicated by block 1314. As described elsewhere in this disclosure, the set of context parameters may include domains of knowledge, different class categories representing expertise within a domain, user roles, user permissions, predicted domain classes, values of environmental variables, or the like. In some embodiments, the process of obtaining the set of context parameters may include determining one or more values from data associated with a data session between a server and a client computer device of a user. For example, some embodiments may determine the domain expertise(s) of a user based on the account by which the user is using to access the data session. Alternatively, or in addition, some embodiments may determine a set of user-specific context parameters based on information determined from an analysis of a user input. For example, some embodiments may determine a predicted domain class representing an expertise score for a user based on a set of queries made by the user.

In some embodiments, the process 1300 may include obtaining a set of natural language documents and corresponding learned representations of n-grams of the set of natural language documents, as indicated by block 1318. Various operations may be performed, such as those described for the process 400 above. As described elsewhere, set of natural-language documents may be obtained in the form of a corpus of text from various sources. For example, some embodiments may obtain a set of natural-language text documents from a corpora of natural-language text documents after receiving a query, where the query may be updated to include n-grams of one or more ontologies. Some embodiments may then generate learned representations of words, phrases, or other n-grams of the documents using one or more operations described in this disclosure.

As described elsewhere in this disclosure, some embodiments may determine a set of embedding vectors of a natural language document using a transformer model or other neural network model. These embedding vectors may represent vectors in an embedding space, where pairwise distances between respective vector pairs indicate semantic similarities between the n-grams represented the respective pairs. In some embodiments, these embedding vectors may be generated as part of the hidden state outputs of a layer of a set of neural network layers. As described elsewhere in this disclosure, one or more models may be used to generate embedding vectors for words or other n-grams, such as BERT, XLNet, GPT, or the like. For example, some embodiments may use XLNet or another autoregressive transformer model to generate word embeddings, where XLNet is described in Yang et al. (Yang, Z., Dai, Z., Yang, Y., Carbonell, J., Salakhutdinov, R. R. and Le, Q. V., 2019. Xlnet: Generalized autoregressive pretraining for language understanding. In Advances in neural information processing systems (pp. 5753-5763)), which is incorporated herein by reference. For example, some embodiments may to generate embeddings for a word of a document, where the word (or another n-gram) may be assigned an embedding vector based on both the word itself, its position with respect to other words surrounding the word, and the embedding vectors of the other words.

Some embodiments may determine different embedding vectors or other learned representations for a same n-gram based on other n-grams of the document being analyzed or a domain category value associated with a user. For example, some embodiments may generate a first vector for an n-gram of a document when a first user is retrieving the document and generate a second embedding vector different from the first embedding vector for the same n-gram of the document when a second user is retrieving the same document. In some embodiments, the embedding vector of the word or its surrounding words may be influenced based on an ontology graph or plurality of ontology graphs, where the set of ontology graphs may be selected based on a domain category value(s) associated with a user. For example, an association between vertices corresponding with the ontology graphs may be used to update an embedding vector or its distance with another embedding vector. In some embodiments, the update may reduce the distance between related embedding vectors. For example, if an ontology graph edge indicates that an ontology vertex pair mapped to by the embedding vector pair are equivalent to each other or that one is a superset of another, some embodiments may determine or update one or both of the a pair of embedding vectors to reduce the distance between the vectors.

In some embodiments, the process 1300 may include determining scores for text sections of a natural-language text document, as indicated by block 1320. A text section may include an n-gram or a plurality of in-grams. For example, a text section may include a portion of a word, a whole word, a phrase, a clause, a sentence, a paragraph, multiple paragraphs, or the like. For example, some embodiments may segment a natural language document into a sequence of text sections including a first text section representing a first sentence or paragraph and a second text section representing the following sentence or paragraph of the first sentence. As described further below, some embodiments may select text sections from the sequence of text sections based on their scores and use the n-grams of the selected text sections to generate summarizations. Furthermore, as described elsewhere in this disclosure, some embodiments may use a set of learned representations of a natural-language text document determined using another operation described for one or more blocks of the process 1300 to determine scores for text sections of the natural-language text document. For example, some embodiments may have determined embedding vectors for words, phrases, or other n-grams of a document during a previous operation and use the sequences of embedding vectors corresponding to sentences when determining scores for the sentences of a document.

Various types of scoring models may be used to score n-grams of a natural-language text document, where n-grams of a natural-language text document may be scored by individually scoring the n-grams or by scoring text sections including the n-grams. In some embodiments, the scoring model may be a model used for extractive summarization methods, where one or more text sections may be selected as summarizing text sections based on the value of the corresponding scores. Some embodiments may determine topic scores for each sentence of a natural language document. In some embodiments, each respective topic score corresponding to a respective text section and may indicate relevance to a topic, where the topic may be determined from a query or an updated query. For example, a first topic of a query may include the phrase "atrial fibulation" based on the query including the phrase "atrial fibulation," and a second topic of the query may include the acronym "NVAF" based on a set of cross-graph associations between the n-gram "NVAF" and the n-gram "Atrial Fibulation."

In some embodiments, one or more probabilistic models may be used to score a text section to determine relevance with a document or a query used to retrieve the document. Some embodiments may use a latent Dirichlet allocation (LDA), latent semantic analysis (LSA), or the like. For example, some embodiments may generate topics for a document based on a LDA model or other probabilistic model and then determine the topic scores of text sections of the document based on the selected topics. Various operations may be performed when determining topics using an LDA model, such as representing a document as a set of features using a bag-of-words or determining a distribution parameter of a set of documents. For example, some embodiments may determine a distribution parameter based on the frequency of a set of words appearing in a set of documents. Some embodiments may then determine the probability of a text section being relevant to a specified topic based on a frequency of mentioning the topic, where the topic may be mapped to by a query provided by the user via an ontology graph.

In some embodiments, the scoring model may include a neural network for determining a topic score or other type of score indicating that a section of text is relevant for summarization. For example, some embodiments may use a recurrent neural network to determine a learned representation of a sentence with respect to a specific topic, where different RNNs may be used to determine different sentence scores for a same sentence with respect to different topics. Some embodiments may select a set of text sections that satisfy a score criteria such as a relevance threshold or select a set of text sections based on their rankings to determine which text sections to analyze or display in a user interface (UI).

In some embodiments, as described elsewhere in this disclosure, some embodiments may generate scores for individual n-grams of a document. For example, some embodiments may generate a score for each n-gram of a sentence of a document, and text sections comprising the sentence may be scored based on the individual scores of the n-grams. In some embodiments, the scoring model may include a neural network that determines a sentence score. For example, some embodiments may use a recurrent neural network to determine a learned representation of a sentence with respect to a specific topic, where different RNNs may be used to determine different sentence scores for a same sentence with respect to different topics. Some embodiments may then select a set of text sections that satisfy a score criteria such as a relevance threshold (e.g., in the form of a minimum score threshold) or select a set of text sections based on their rankings to determine which text sections to analyze or display in a user interface (UI). In some embodiments, the neural network may have been trained to update a score in response to detecting the presence of one or more n-grams associated with an ontology graph.

In some embodiments, the process 1300 may include selecting an initial set of n-grams based on the natural-language text document and a first ontology graphs of the set of ontology graphs, as indicated by block 1324. As described elsewhere in this disclosure, some embodiments may select the initial set of n-grams based on the selected text sections described above for block 1320 such that each n-gram of the initial set of n-grams is found in a selected text section. Alternatively, some embodiments may select an initial set of n-grams from the entirety of a natural-language text document instead of retrieving n-grams only from selected text sections. Some embodiments may select the initial set of n-grams based on each n-gram of the initial set being mapped to one of a first set of vertices of a first ontology graph, where each of the first set of vertices map to a concept or other vertex of another ontology graph. may determine a set of embedding vectors in an embedding space for n-grams and determine vertices of an ontology graph identified by the embedding vectors. For example, some embodiments may determine that a set of five words are in a first ontology and mapped to concepts of a second ontology and, in response, add the set of five words to the initial set of n-grams.

In some embodiments, the process 1300 may include determining whether a set of domain-specific indices is available, as indicated by block 1330. Some embodiments may retrieve a set of associations to perform one or more operations described in this disclosure, where the set of association may include a set of domain-specific indices or a set of ontology graphs. In some embodiments, the set of domain-specific indices may include an index having a data structure optimized for information retrieval, such as a self-balancing search tree or a trie, where the index may be generated or updated based on a set of ontology graphs. As described elsewhere in this disclosure, some embodiments may use an index to determine associations between different n-grams, where the different n-grams may be associated with different domains, different domain classes, or other different domain category values. Some embodiments may determine that a cross-domain index is available after finding an index storing n-grams or their corresponding embedding vectors of a first ontology, where the index includes, for each n-gram or corresponding embedding vector(s), an association with other n-grams or corresponding embedding vectors of a second ontology. If a determination is made that a cross-domain index that includes the initial set of n-grams is available, operations of the process 1300 may proceed to block 1334. Otherwise, operations of the process 1300 may proceed to block 1344.

In some embodiments, the process 1300 may include selecting one or more indices based on the set of domain category values, as indicated by block 1334. Some embodiments may use a single index that includes one or more keys based on an n-gram, an embedding vector determined from an n-gram, or a domain category value and has, as a value a corresponding n-gram of a different domain category value. Information associated with the index may indicate that the index provides a mapping from a first n-gram or its corresponding learned representation to a second n-gram or its corresponding learned representation. Some embodiments may use this information after determining that a user is associated with a domain, domain class, or other domain category value that is mapped to by the index.

In some embodiments, the process 1300 may include retrieving a second set of n-grams related to the initial set of n-grams based on the one or more selected indices, as indicated by block 1338. As described elsewhere in this disclosure, an index may be stored in various forms that increase the speed of data retrieval, such as in the form of a self-balanced search tree, a trie, or the like. In some embodiments, a self-balanced search tree, prefix tree, or other index may be loaded into a cache memory to increase data retrieval speeds, where a cache memory may include an L1 cache, L2 cache, L3 cache, or another cache memory of a different or mixed cache level. A cache memory may refer to a hardware cache that is integrated with a computer processor and characterized by being faster to access than other memory of a computer system and may include one or more SRAM components. By allocating ontology-specific indices into a cache memory of a computing device, some embodiments may accelerate the speed by which ontology-specific text summarization is performed.

Various operations may be performed to retrieve related n-grams of an initial set of n-grams using an index. Some embodiments may search through a self-balancing search tree based on a key, where the key may be an n-gram or a learned representation of the n-gram. Some embodiments may search through the self-balancing search tree by starting at a root of the self-balancing search tree and recursively traversing tree nodes using the key to retrieve a second n-gram or corresponding embedding vector at a leaf node of the self-balancing search tree. Alternatively, or in addition, some embodiments may use an index stored in the form of a trie, where the trie may be associated with a first ontology and a second ontology such that it may be retrieved from a database or other data structure with identifiers of the first and second ontology. Some embodiments may traverse nodes of the trie based on an n-gram of the initial set of n-grams to retrieve a second n-gram, where the second n-gram may be part of a different ontology. By using an index connecting n-grams or representations of n-grams between different ontologies, some embodiments may accelerate the speed of data retrieval, text summarization, or other operations described in this disclosure.

In some embodiments, the process 1300 may include determining a first set of vertices of a first ontology graph based on the initial set of n-grams, as indicated by block 1344. As discussed elsewhere in this disclosure, some embodiments may include a one-to-one mapping of n-grams to vertices of an ontology graph. Alternatively, or in addition, some embodiments may map an n-gram to multiple vertices of an ontology graph based on embedding vectors or other learned representations of an n-gram. Some embodiments may map the first n-gram to multiple vertices by mapping the n-gram to multiple embedding vectors, where each embedding vector may correspond with a vertex of an ontology graph. As discussed above, some embodiments may convert the initial set of n-grams into a set of embedding vectors when selecting the initial set of n-grams, scoring text sections. For example, some embodiments may have previously determined the embedding vectors corresponding to a set of n-grams and re-use embedding vectors of the n-grams to select vertices of a first ontology graph. Alternatively, or in addition, some embodiments may generate a new set of embedding vectors that are independent of other embedding vectors that may have been previously determined.

In some embodiments, the process 1300 may include determining a second set of n-grams and a corresponding second set of vertices of a second ontology graph based on a direct association or indirect association with the first set of vertices, as indicated by block 1348. As described elsewhere in this disclosure, some embodiments may include a plurality of ontology graphs associated with different domains of knowledge or different class values within a domain of knowledge. For example, some embodiments may retrieve a plurality of ontologies that include a first ontology graph may be associated with the domain "cardio neurology" and the domain class "3," which is selected from a list of domain classes ["1", "2", "3" ]. The plurality of ontologies may also include a second ontology graph that is associated with the same domain of "cardio neurology" but differ by labeled with a domain class "2."

As discussed elsewhere in this disclosure, some embodiments may associate vertices of a first graph with vertices of a second graph via a direct association. In some embodiments, a direct association between two ontology vertices may include an ontology graph edge represented by a pair of values linking the two vertices by their corresponding unique identifiers. In some embodiments, one or more vertices of the second graph may represent a set of concepts that represent supersets, subsets, equivalencies, or other relationship types with an n-gram indicated by the vertices of the first graph. For example, some embodiments may recognize the n-gram "nursing mother" as a named entity associated with a first vertex of a first ontology by directly identifying the vertex by the named entity or by an embedding vector representing the named entity. Some embodiments may then detect an association between "nursing mother" and the second n-gram sequence "nursing woman" via an edge connecting the first vertex and a second vertex of a second ontology graph. After detecting the association, some embodiments may include the second n-gram in a set of related n-grams of the n-gram "nursing mother."

In some embodiments, the edge may be labeled with a relationship type, such as a category selected from a list of categories. For example, some embodiments may determine that a first vertex of a first ontology mapped to from the term "nursing mother" in a query is connected to a second vertex of a second ontology via an edge represented by an ordered pair of vertex identifiers. The edge may be labeled with a category indicating a relationship type selected from the list of categories '["subset", "superset", "cause", "symptom" ].' For example, some embodiments may determine that the term "nursing mother" is a type of "nursing woman" based on a relationship type associated with a graph edge connecting the vertices corresponding with "nursing mother" and "nursing woman," where the relationship type may be "subset." Some embodiments may limit associations between related vertices to specific relationship types. For example, some embodiments may determine that a relationship type between a first vertex and a second vertex is categorized with the value "subset" and determine that the relationship type is in a set of criteria relationship types. In response to the relationship type being in the set of criteria relationship types, some embodiments may then add the vertex to the second set of vertices for use when generating a sequence of n-grams, as further described below. Otherwise, some embodiments may ignore the edge associating the first vertex with the second vertex.

In some embodiments, the process 1300 may include generating a sequence of n-grams based on the initial set of n-grams, the second set of n-grams, or the selected text sections, as indicated by block 1360. Generating the sequence of n-grams may include using one or more abstractive text summarization models, where an abstractive text summarization model may take input text to generate text summaries that include words or word combinations not found in the input text. In some embodiments, the abstractive text summarization model may include a sequence-to-sequence RNN model, where a sequence-to-sequence RNN model may use an encoder neural network of the RNN to provide a set of hidden state values from a sequence of n-grams. The hidden state values may include a set of learned representations, such as those described above. One or more layers of a first set of neural network layers of an encoder neural network may obtain, as an intermediate input, a set of hidden state values outputted from a previous layer of the first set of neural network layers, where a first input to the RNN model may include a sequence of n-grams or learned representations of the n-grams. For example, some embodiments may provide a sequence of n-grams to an RNN in order to obtain a set of hidden values as outputs. Some embodiments may use the set of hidden values as inputs for a set of decoder neural networks of the sequence-to-sequence RNN to determine a sequence of output embedding vectors that may then be converted into a sequence of n-grams for use as a summary.

Some embodiments may use the embedding vectors or other learned representations determined in an operation described above as part of the set of hidden values or otherwise include the embedding vectors in the set of hidden values. For example, some embodiments may have determined a set of embedding vectors based on the n-grams when first retrieving a document and generating scores for text sections of the document. This set of embedding vectors may then be re-used when selecting vertices of ontologies or generating a sequence of n-grams. Alternatively, or in addition, some embodiments may generate a set of hidden values that are independent of a previously-calculated the set of embedding vectors when generating a text summarization.

Some embodiments may use a neural network model to determine words of a summarization string based on a set of hidden state values of the neural network model. For example, some embodiments may use a decoder neural network to determine a word of a summarization string based on the output of an encoder neural network, where the word being determined may be the last word of an n-gram sequence. Some embodiments may augment summarization operations by using a set of attention values or other values determined in combination with the set of hidden values, where the set of attention values may indicate which n-grams of a sequence of n-grams should be given a greater weight when determining an output using an RNN.

As described elsewhere in this disclosure, some embodiments may use a transformer model to generate a summarization by determining a set of positional encoding vectors, where each respective positional encoding vector may be based on a position of a respective word in the text section. An encoder neural network of the transformer model may include a multi-headed attention model for performing self-attention operations. As further described below, performing self-attention operations may include assigning attention values to each of the n-grams in a sequence of n-grams based on the positional encoding vectors and other intermediate outputs of the encoder neural network model. By performing self-attention operations, some embodiments may assign attention values to each word based on relations between different n-grams in the sequence of n-grams. These attention values may then be used as additional inputs in conjunction with a sequence of embedding vectors by a set of decoder neural network layers to predict additional n-grams for a sequence of n-grams, where the additional n-grams may be at the end of the sequence and usable in a summary. Alternatively, or in addition, these attention values may be used to determine the set of embedding vectors.

Some embodiments may perform self-attention operations by computing a set of key vectors, query vectors, or value vectors determined using a set of embedding vectors and positional encoding vectors. In some embodiments, the key, query, and value vectors may be determined during a training operation of a transformer model. After training, some embodiments may compute attention values using a function that takes, as input(s), the sets of key, query, and value vectors. For example, using an attention-determining function may include computing a product of a first element of a query vector with a second element of a key vector, where the product may be computed as part of a dot product determination between a query vector of a first n-gram with key vectors of other n-grams of a sequence of n-grams, where the output of the dot product may be further processed to determine an attention value. Various modifications to the output vector(s) may be performed, such as determining a root of the output, performing a normalization of the root by performing a set of softmax operations, or the like. Performing the set of softmax operations may include determining a ratio of an exponential value and a sum of exponential values, where the inputs of the exponential value may include outputs of a previous set of neural network layers, such as the set of decoder neural network layers. Additionally, some embodiments may determine an attention value based on an association an ontology graph. For example, some embodiments may increase an attention value based on the attention value being assigned to an n-gram of a second ontology, where the n-gram of the second ontology represents a concept that is mapped to by an initial n-gram of a query.

Some embodiments may perform abstractive summarization to generate a sequence of n-grams by using a pointer generation network model. Using a pointer generation network model may include computing a first value when determining an n-gram based on a vocabulary score distribution and a second value based on an attention value distribution. In some embodiments, scores of the vocabulary score distribution may be linked to a set of n-grams, where the score may be increased for n-grams found in a user-provided query or associated with an ontology graph vertex. Using the pointer generation network model may include determining a n-gram selection score based on a weighted sum that includes the first value and the second value, where the n-gram selection score may then be used to select an n-gram. Using the pointer generation network model may include determining a n-gram selection score associated with an n-gram based on a weighted sum that includes the first value and the second value. Some embodiments may then determine an n-gram based on the n-gram selection score and add the n-gram to a summary. For example, an n-gram selection score for a first n-gram may be defined as a sum of the probability that a new n-gram is generated after it is weighted by (e.g., multiplied by) by the vocabulary score of the first n-gram and the sum over a set of attention values corresponding with the word, where the sum over the attention value may be weighted by a complement of the probability that a new n-gram. Some embodiments may determine a probability value using a random or pseudorandom operation, where satisfying an n-gram generation threshold determined from the weighted sum with the probability value may cause the generation of a new n-gram in place of an existing n-gram of a document when determining what n-gram to use while generating a sequence of n-grams. In some embodiments, the new n-gram may be an n-gram associated with a second ontology graph, where the second ontology graph may be associated with a user domain or domain class.

Some embodiments may also compute a coverage loss value when generating a sequence of n-grams for a text summary. Some embodiments may perform a coverage loss computation by determining a coverage vector based on a position and a sum of previous attention vectors. Each set of the sets of previous attention vectors may be associated with a position in the summarization. For example, some embodiments may determine an attention distribution having attention values for each n-gram of a summarization, where the attention values may be determined using one or more operations described above. Some embodiments may perform one more operations described above to determine a plurality of attention distributions, where elements of a respective attention distribution of the plurality of attention distributions may be used to update hidden state outputs of one or more neural network layer corresponding with n-grams of a sequence of the natural-language text document. Some embodiments may then determine a coverage vector for the next word by computing a sum of the attention distributions for each previous n-gram of a summarization. The coverage loss value of an n-gram may be set to the lesser between the attention value associated with the n-gram and the coverage value in the coverage vector of the n-gram. Some embodiments may use this coverage loss value as part of a loss function to determine the next word for a summarization. By incorporating a coverage loss value into the loss function, some embodiments may decrease the repetitiveness of a summary or otherwise increase the conciseness of the summary.

Some embodiments may be capable of retrieving one or more stored configurations or versions of a text summarization model, where the stored configurations may include different sets of neural network parameters. For example, some embodiments may retrieve two or more text summarization models for generating a sequence of n-grams based on a user being associated with two different domains or domain class values. Some embodiments may then select which of the text summarization models to use based on a preference weight, where the preference weight may be a binary value, categorical value, or categorical value. For example, some embodiments may retrieve a first set of neural network parameters for a text summarization model in response to a determination that a first user is associated with a first domain category value. Additionally, some embodiments may then retrieve a second set of neural network parameters for the text summarization model in response to a determination that a second user is associated with a second domain category value.

Some embodiments may generate an initial sequence of n-grams based on an input natural-language text document or a corresponding set of embedding vectors. Some embodiments may then update the initial sequence of n-grams using a set of related n-grams determined via a set of graph edges of vertices associated with different domain category values. For example, some embodiments may select a subset of n-grams of the initial sequence of n-grams. Each respective first n-gram of the subset of n-grams may be mapped to a respective first vertex of a first ontology graph that is itself associated with a respective second vertex of a second ontology graph via a set of associations (e.g., an index, a pointer stored as a part of a vertex, or the like). Some embodiments may then directly replace the respective first n-gram with a respective second n-gram identified by the respective second vertex or otherwise update the initial sequence of n-grams with the respective second vertices. In some embodiments, replacing the respective first n-gram with the respective second n-gram may include replacing a respective first embedding vector corresponding with the respective first n-gram with a respective second embedding vector corresponding with the respective second n-gram. As described further below, some embodiments may then present the summarization with the respective second n-gram instead of the respective first n-gram.

In some embodiments, the process 1300 may include presenting a summary in a UI that includes the sequence of n-grams, as indicated by block 1370. Presenting the UI may include one or more operations described elsewhere in this disclosure, such as operations disclosed for block 430. In some embodiments, the UI may include a set of UI elements that, when interacted with by a user, may indicate a feedback message provided by the user. The feedback message may be used to adjust a preference weight associated with an ontology graph. By adjusting the preference weights, some embodiments may modify the degree to which a specific ontology is used when generating a summary. For example some embodiments may receive a feedback message indicating that a summary is accurate and, in response, some embodiments may increase a preference weight associated with the set of ontologies used to generate the summary. Alternatively, some embodiments may receive a feedback message indicating that a summary is inaccurate and, in response, some embodiments may decrease a preference weight associated with the set of ontologies used to generate the summary.

As described above, some embodiments may adjust preference weights associated with different ontology graphs, where the preference weights may be used to determine the vocabulary used to generate summaries. For example, after adjusting a set of weights associated with a first and second ontology, some embodiments may select the second ontology amongst the plurality of ontologies based on the second weight being greater than the first weight. By updating the ontologies used, some embodiments may provide a more comprehensible summarization for a user. For example, if a user is associated with a first ontology that is labeled with the domain category value "expert" and provides a feedback message indicating that this domain category value is too difficult, some embodiments may reduce the preference weight associated with the first ontology and a subsequent summarization operation may rely on an ontology that is labeled with the domain category value "beginner."

In some embodiments, the UI may visually indicate words, phrases, or other n-grams of a summarization. In some embodiments, the UI may indicate words of an extracted summarization that match or are otherwise similar to words used in the query. Alternatively, or in addition, the UI being presented by a client computer device may indicate that a word, phrase, or other n-gram of a summarization is an n-gram of a vertex associated with an ontology associated with a user's domain, domain class, or other domain category value. For example, some embodiments may display a summary on a visual display of a client computer device including the phrase, "the AF was successful," where the acronym "AF" may be part of an ontology associated with a domain class of the user that was not originally in the document being summarized.

Some embodiments may visually indicate the acronym "AF" or other related n-grams of a set of related n-grams of a first n-gram retrieved from a document. Visually indicating a related n-gram may include using one or more types of visual indicators, such as changing the text color, text size, text background color, font style, or the like of the acronym relative to other n-grams of the summarization. Some embodiments may also update the summary to include links to other n-grams or other information. Some embodiments may present the UI as a web document, where the source code of the web document may include embedded tags surrounding a first n-gram, where the presence of the embedded tags may make the text representing first n-gram an interactive UI element and cause the display of another n-gram mapped to the first n-gram after an interaction with the interactive UI element. For example, some embodiments may add embedded tags in the vicinity of the acronym "AF" that causes the UI to display the n-gram "fibrillation operation" and further cause the UI to display a definition for the concept represented by the n-gram "fibrillation operation" in response to a user clicking on or tapping on the acronym "AF." Some embodiments may generate the link based on the association between the "AF" and "fibrillation operation" via a mapping between a vertex of a first ontology graph identifying the n-gram "AF" and a vertex of a second ontology graph identifying the n-gram "fibrillation operation." Alternatively, or in addition, some embodiments may provide a set of UI elements to update associations between n-grams of a set of ontology graphs. For example, some embodiments may permit a user to highlight a set of n-grams and indicate that the highlighted set of n-grams is associated with another n-gram (e.g., an n-gram of a query, an n-gram of a document, an n-gram that is entered into a text box, or the like).

As described above, some embodiments may present multiple summaries of a same document. For example, some embodiments may generate a first text summary of a document using a plurality of ontologies and a second text summary of a document using only one ontology or no ontologies. The first text summary may include n-grams of a first ontology and n-grams of a second ontology, while the second text summary may include n-grams of the first ontology without including n-grams of the second ontology. Some embodiments may concurrently display both the first and second text summaries, where a user may select which type of text summary they would prefer to view in a U. Some embodiments may include the option for a user to concurrently see both text summaries of a document or view only one text summary of the document.

Figure 14:
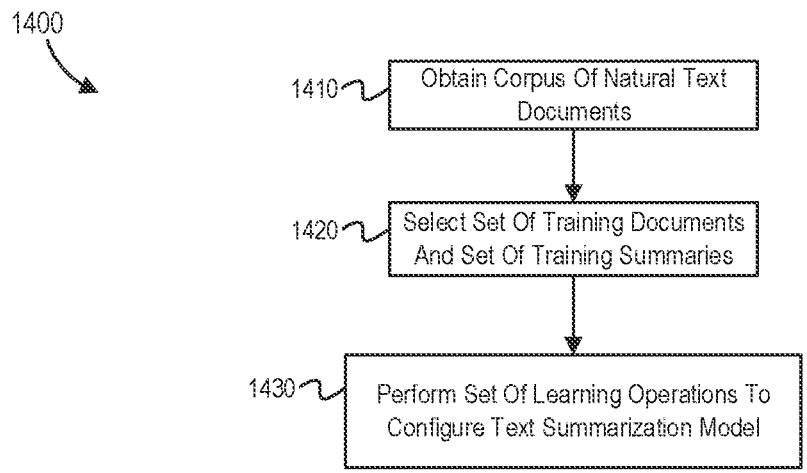
FIG. 14 is a flowchart of an example process by which a domain-based summarization model may be configured, in accordance with some embodiments of the present techniques.

FIG. 14 is a flowchart of an example process by which a domain-based summarization model may be configured, in accordance with some embodiments of the present techniques. Operations of the process 1400 may begin at block 1410. In some embodiments, the process 1400 may include obtaining a corpus of natural text documents, as indicated by block 1410. Operations to obtain a corpus of natural documents may include one or more operations described in this disclosure. For example, some embodiments may obtain a set of text documents from public or nonpublic sources, where the text documents may be stored in association with specific domains, domain classes, or other domain category values.

In some embodiments, the process 1400 may include selecting a set of training documents and set of training summaries, as indicated by block 1420. Some embodiments may select a set of text documents for training purposes, where different subsets of text documents may be associated with each other. For example, some embodiments may obtain a first text document representing the body of a research article, a second text document representing the abstract for the research article, and a third text document representing a protocol derived from the research article. Some embodiments may then use the first and third text document in conjunction to train a text summarization model to generate a summary determined from the abstract.

As described above, some embodiments may train and use a plurality of summarization models. In some embodiments, each summarization model of the plurality of summarization models may be labeled with or otherwise associated with different domains of knowledge. For example, some embodiments may train a respective summarization model by using a respective set of training documents labeled with a respective domain of knowledge as training inputs. After obtaining a query and identifying the respective domain based on a user context parameter, some embodiments may then retrieve the respective summarization model and corresponding model parameters (e.g., neural network parameters, statistical model parameters, or the like) associated with the respective domain.

Some embodiments may obtain a set of text documents and perform one or more operations to extract a respective pre-existing text summary from each respective document of the set of text documents. For example, some embodiments may retrieve a training document from a set of training documents and segment the training document based on headers or whitespace separation to obtain an abstract of the document. After extracting the abstract, some embodiments may use the abstract as a summary for the text document and use sequences of n-grams of the abstract as a training summary usable to train one or more text summarization models when paired with a corresponding training document, as described further below. For example, some embodiments may extract a paragraph from a text document in response to a determination that the paragraph has the header "article summary" or is separated by line breaks from other text in the document. Some embodiments may then add the paragraph or sequences of n-grams of the paragraph to a set of training summaries usable as training objectives when training a text summarization model. Some embodiments may then, for each respective pre-existing text summary, perform one or more operations described above to add a respective sequence of n-grams of the respective pre-existing text summary to a set of training summaries or a learning operation, as described further below.

In some embodiments, the process 1400 may include performing a set of learning operations to configure a text summarization model, as indicated by block 1430. Performing a set of training operations may include performing a set of supervised learning operations, semi-supervised learning operations, reinforcement learning operations, or the like. For example, as described elsewhere in this disclosure, some embodiments may generate a learned representation such as embedding vectors for n-grams of a document.

Some embodiments may train or otherwise configure a plurality of text summarization models based on different domains or domain classes, or other domain category values. For example, some embodiments may train a first text summarization model for a first domain "neurology" with a domain class of "expert" and train a second text summarization model for the same domain "neurology" with a domain class of "intermediate," where the first text summarization model and second text summarization model may be different. For example, the first and second text summarization model may differ with respect to a number of neural network layers, the weights of the neurons of the neural network, biases of the neural network, activation function parameters of the neural network, or architecture of the neural networks, or the like. Some embodiments may use a provided set of training summaries corresponding to different domain classes or other domain category values, where a document may be associated with a plurality of summaries, each summary being associated with a different domain category value. Alternatively, or in addition, some embodiments may train a text summarization model and update the output of the text summarization model with ontologies indicated by a user profile after the text summarization model as provided the sequence of n-grams.

Some embodiments may then select one of the neural network models to use based on the domain category value associated with a user that is to be presented with a summary. For example, a first user may have the domain category class "expert," and some embodiments may provide a first text summary generated by a first version of a neural network model. Some embodiments may then provide a second text summary generated by second version of the neural network model for a second user after a determination that the second user is associated with the domain category class "neophyte."

Figure 15:
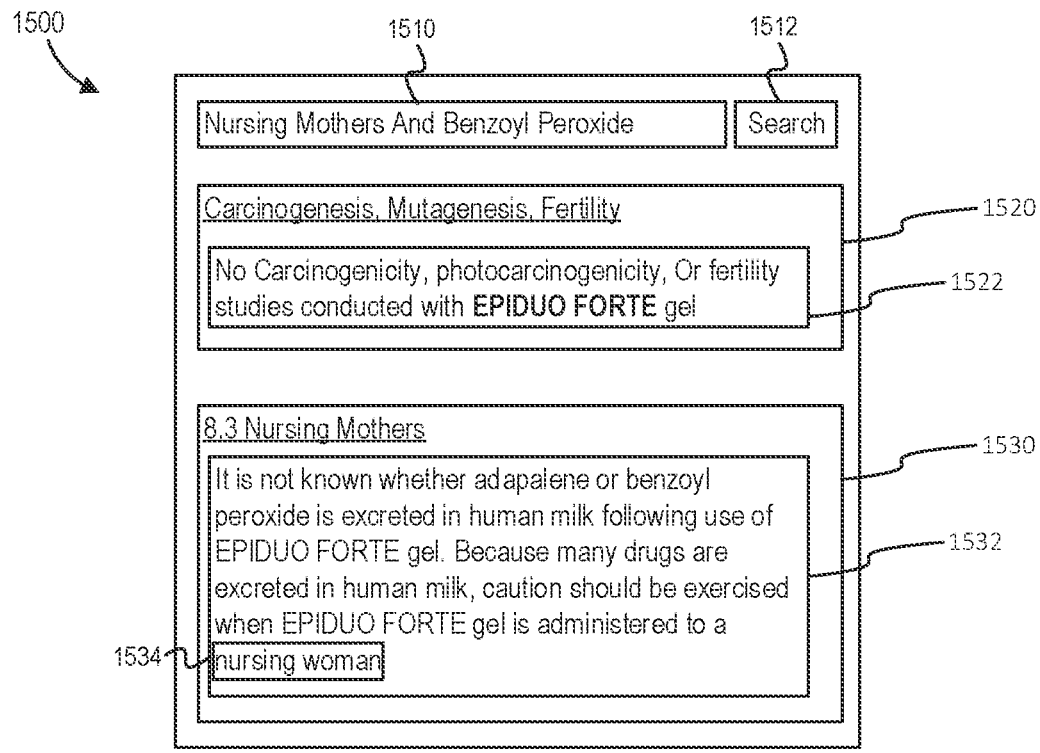
FIG. 15 is an example user interface including an ontology-generated summary, in accordance with some embodiments of the present techniques.

FIG. 15 is an example user interface including an ontology-generated summary, in accordance with some embodiments of the present techniques. The UI 1500 shows a search bar 1510 displaying the query, "nursing mothers and benzoyl peroxide." After an interaction with the UI element 1512, some embodiments may display a first search result box 1520 having a document summary 1522 and a second search result box 1530 having a document summary 1532.

Some embodiments may perform one or more operations described in this disclosure to generate the document summary 1522 based on the document titled "Carcinogenesis, Mutagenesis, Fertility" identified by the first search result box 1520. For example, some embodiments may use an abstractive summarization method to generate the summary, "no carcinogenicity, photocarcinogenicity, or fertility studies conducted with EPIDUO FORTE gel." As described elsewhere in this disclosure, some embodiments may use a set of ontologies to recognize the named entity "benzoyl peroxide" in a first ontology as being associated with the named entity "EPIDUO FORTE" of a second ontology graph, where the second ontology graph may be labeled with a domain class value indicated by the user.

Similarly, embodiments may perform one or more operations described in this disclosure to generate the document summary 1532 based on a document titled "8.3 Nursing Mothers," identified by the second search result box 1530, which is shown to be displayed concurrently with the document summary 1522. Some embodiments may generate the document summary 1532 using the same text summarization model as the one used for generating the document summary 1522. For example, some embodiments may use a text summarization model to search through a set of ontologies or indices representing the ontologies to determine a first set of n-grams of one or more domains or classes of domains indicated by a user profile. Some embodiments may use n-grams or learned representations of the n-grams indicated by the set of ontologies or indices as mapped to one or more n-grams of the query to generate the document summary 1522 and the document summary 1532.

Some embodiments may update the UI 1500 to indicate one or more n-grams are related to an n-gram of a query via a set of ontology graph edges. For example, the named entity "EPIDUO FORTE" is shown to be bolded in response to a determination that "EPIDUO FORTE" maps to the term "Benzoyl Peroxide" in an index or cross-graph edge of a set of ontologies. In addition, the n-gram "nursing mothers" is associated via a cross-graph edge with the n-gram "nursing woman," where the box 1534 may indicate a highlighting or color change. In some embodiments, the UI 1500 may be presented as a web document, and the embedded tags around one or more n-grams determined as related via a set of ontologies may be used convert the text display of the n-gram into a hyperlink or otherwise generate an interactive UI element that overlaps with the text display of the n-gram. In some embodiments, interacting with the interactive UI element may cause the display of the n-gram that caused the display of a second n-gram, where the second n-gram may be an n-gram of the query or an n-gram of a concept to which the n-gram of the query maps.

IV. Question Generation

As discussed elsewhere in this disclosure, some embodiments may use one or more indices to obtain or process information based on a query. In many cases, the query posed by a user may be provided in a form different from that used by a document storing an answer to the query. For example, a query of a user may be written in the natural language form, "Does it take long to grow *E. coli*." Some embodiments may use the query to search through a corpus of documents to retrieve an answer to the query in a protocol, where the protocol may recite "*Escherichia coli* requires 24 hours to incubate." However, the different words, phrases, and structure of a user-provided query may also provide text from other documents that are not as relevant, reducing both the accuracy and effective speed of a search operation.

Some embodiments may use an index that matches n-grams of a query with n-grams stored in or otherwise associated with documents (e.g., as metadata tags). As described above, the index may be constructed using a set of operations that includes scanning the words, phrases, or other n-grams of the text of a corpus of documents and generating a list of n-grams mapping to the respective document(s) in which they are found. However, using indices that are unable to account for vocabulary differences or phrasing differences between a user's query and the answer stored in a document may provide suboptimal search results to the query. Such differences may include an omission of a word that is part of the answer to the query or the inclusion of extraneous words that are not present in the answer. Additionally, a query may be syntactically different from the structure of a document that contains an answer relevant to the query. Furthermore, some indices may fail to distinguish between multiple passages within a document containing the same n-gram, but where the context in which the n-gram is used may be sufficiently different as to cause the n-gram to be mapped to a different embedding vector.

Some embodiments may accelerate the speed of data retrieval by generating queries based on the text in a document, where an identifier of the document or other data associated with the document may be stored in an index mapping the computer-generated query to the document. For example, some embodiments may obtain a document from a corpus of text, select a text section based on the likelihood that the text section includes an answer relevant to a user-provided query, and generating a query based on the text section. The computer-generated query may include words or phrases from the document, where n-grams of the computer-generated query or the text section(s) used to generate the query may be updated or replaced based on a set of ontologies as described elsewhere in this disclosure. After augmenting an index with the data associated with the computer-generated query, some embodiments may then use the index when performing a search for documents based on a user-provided query.

By performing one or more of the operations described in this disclosure to update the index based on the computer-generated queries, some embodiments may provide faster or more accurate search results for queries. Some embodiments may also increase the accuracy of such search results by updating computer-generated queries with alternative terminology or shared concepts based on a set of ontologies associated with different domains. Some embodiments may further re-arrange or form alternative structural constructions of a computer-generated query based on a set of query structures, such as a query structure formed from a history of previous queries. By generating or otherwise updating queries and storing learned representations of them in an index in association with a document or text in the document, some embodiments may account for variations in query vocabulary or syntax that may occur in natural-language queries. Such operations may be integrated into a chatbot application, voice command application, or the like.

Figure 16:
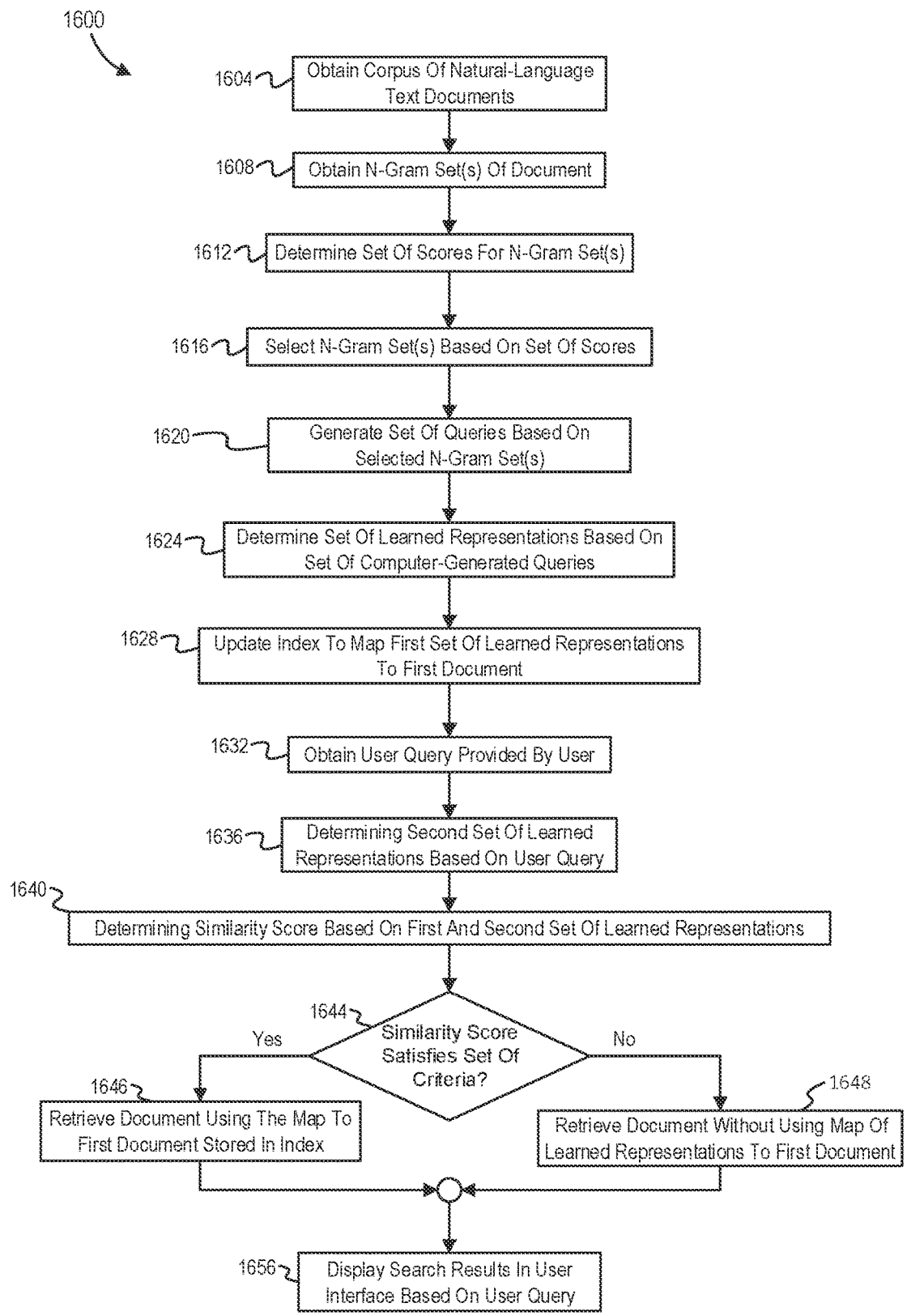
FIG. 16 is a flowchart of an example process by which a query-augmented index is generated and used, in accordance with some embodiments of the present techniques.

FIG. 16 is a flowchart of an example process by which a query-augmented index is generated and used, in accordance with some embodiments of the present techniques. Operations of the process 1600 may begin at block 1604. In some embodiments, the process 1600 may include obtaining a corpus of natural-language text documents, as indicated by block 1604. Operations to obtain a corpus of natural-language text documents may include one or more operations described above. For example, some embodiments may obtain one or more documents of corpora from a set of public or private data sources, where the text documents may be stored in various formats and with various metadata.

In some embodiments, the process 1600 may include obtaining one or more n-gram sets of a document of the corpus of natural-language text documents, as indicated by block 1608. In some embodiments, an n-gram set may include a sequence of n-grams such as a phrase, a clause, a sentence, a paragraph, or the like. Alternatively, or in addition, an n-gram set may include a single n-gram or a non-sequential plurality of n-grams. Some embodiments may perform preprocessing operations on n-grams to increase the accuracy or efficiency of data processing, where such preprocessing operations may include stemming, lemmatizing, or rooting.

Some embodiments may obtain the sets of n-grams by segmenting the natural-language text documents based on punctuation. For example, some embodiments may obtain the sets of n-grams by segmenting the natural language text documents into sentences, where the segmentation may use a period as a delimiting element. Alternatively, or in addition, some embodiments may obtain n-grams from graphical or tabular elements of a document. For example, some embodiments may obtain one or more n-grams from a document table, where the document table may be displayed as a two-dimensional table with a set of labeled rows or columns. Some embodiments may perform operations to obtain a table title, row title, row identifier, column title, column identifier, or other table elements as one or more n-gram sets. For example, some embodiments may determine a column title of a document table and one or more associated table values in the corresponding column, where each value may correspond to a different row of the table. As further described below, some embodiments may then determine a score based on the n-grams of the tabular data and select n-grams of the tabular data based on the score.

In some embodiments, the process 1600 may include determining a set of scores for the one or more n-gram sets, as indicated by block 1612. Some embodiments may determine scores for sets of n-grams, where each respective score may quantify or otherwise indicate an importance of the respective n-gram set with respect to indexing operations. Some embodiments may quantify an importance of the respective n-gram set based on its relevance to a specified set of topics or a relevance to a specified set of queries. Alternatively, or in addition, some embodiments may quantify an importance of the respect n-gram set based on its connections to other sets of n-grams in a document.

Some embodiments may determine different types of scores when using scores to select sets of n-grams, as further described below. For example, some embodiments may determine a first set of scores corresponding to an initial plurality of n-grams sequences that is then usable to determine a subsequent set of n-gram sequences, where the initial plurality of n-grams sequences may include a plurality of phrases, sentences, multiple sentences, or the like. By generating an initial plurality of n-gram sets and filtering them into a lesser number of n-gram sets, operations may be made more efficient by reducing the number of n-gram sets that some embodiments may process using more computing-resource-intensive operations.

Some embodiments may perform a first set of operations to generate an initial set of scores for the initial plurality of n-grams sequences by determining a count of the times by which one or more n-grams of a document occur in the document. For example, some embodiments may segment a document into an initial plurality of n-gram sequences, such as an initial plurality of sentences. The respective n-gram sequences of the initial plurality of n-gram sequences may be assigned a respective score based on an n-gram count indicating the number of times that the respective n-gram is used. For example, some embodiments may determine an n-gram count for each n-gram of some or all of the n-grams in the plurality of n-gram sequences. Some embodiments may then determine a respective score for a respective n-gram as being equal to the n-gram count, being a multiple of the n-gram count, or correlating with the n-gram count. Some embodiments may then determine an n-gram sequence score associated with an n-gram sequence by combining the sets of n-gram counts (or scores based on the sets of n-gram counts) of the n-gram sequence. Combining the counts may include adding, multiplying, using an exponential function, some combination thereof, or the like. For example, for each respective sequence score of a set of sequence scores corresponding with an initial plurality of n-gram sequences, some embodiments may determine a sum of the n-gram counts corresponding with the n-grams of the respective n-gram sequence.

Some embodiments may modify (e.g., increase or decrease) an n-gram score in response to a determination that a vertex of an ontology graph maps to the corresponding n-gram. For example, an n-gram score of an n-gram that may have been equal to "0.3" may be updated to 0.6" based on a determination that the n-gram maps to a vertex of an ontology graph associated with a first domain. Some embodiments may then select a subset of the initial plurality of n-gram sequences based on a determination if the corresponding plurality of sequence scores satisfy a sequence score threshold. For example, some embodiments may select a sentence from a plurality of sentences for further n-gram selection operations based on the sentence being associated with a sentence score greater than a sequence score threshold. As further described below, the selected subset may then be used as the input set of n-gram sequences (or another set of n-gram sets) for further scoring operations or for other query-generating operations.

Some embodiments may perform operations similar to a Textrank operation based on n-gram connectivity in an n-gram sequence to determine a set of n-gram sequences, where Texrank is described by Mihalcea et al. (Mihalcea, R. and Tarau, P., 2004, July. Textrank: Bringing order into text. In Proceedings of the 2004 conference on empirical methods in natural language processing (pp. 404-411)), which is incorporated herein by reference. Some embodiments may rank n-grams of a document by determining a document-specific vocabulary of n-grams and performing operations to assign n-gram scores to each n-gram of the vocabulary ("vocabulary n-gram"). Some embodiments may determine a set of vocabulary n-grams based on the n-grams of a document by adding n-grams not already in the vocabulary of n-grams to the vocabulary of n-grams such that each n-gram of the vocabulary may be found in the document, where some embodiments may first lemmatize, stem, determine roots for, or otherwise process the n-grams of a document.

Some embodiments may segment the first document into a set of sentences or other plurality of document n-gram sequences and generate a respective set of n-gram pairs for each respective sentence, where each n-gram pair includes two n-grams of the sentence. Some embodiments may select a sequence of n-grams of the sentence as an n-gram window, where the window size may be updated by a processing parameter. For example, some embodiments may generate the two n-gram windows ["man", "owns", "large" ] and ["owns", "large", "tree" ] from the n-gram sequence "man owns large tree" after a determination that the n-gram window size is equal to '3.' Some embodiments may then generate a respective subset of a set of n-gram pairs for each window. For example, some embodiments may generate the set of n-gram pairs ["man", "owns" ], ["owns", "large" ], and ["large", "tree" ] from the n-gram window ["man", "owns", "large" ]. Some embodiments may then update a data table or other data structure identifying the relationships between n-grams of the n-gram vocabulary such that every instance of an n-gram pair updates (e.g., increases) the count. For example, after encountering an instance of the n-gram pair ["man", "owns" ], some embodiments may update a data table storing a count of instances that the n-gram pair ["man", "owns" ] is present in the document. Alternatively, or in addition, some embodiments may generate the set of n-gram pairs from a larger sequence of n-grams without using a window. For example, some embodiments may generate a set of n-gram pairs for each sentence of a document, where a pair exists to represent each pairing of one n-gram of the sentence with another n-gram of the sentence.

Some embodiments may determine an n-gram weight based on the sum of occurrences of the n-gram in an n-gram pair, where the values used to determine the sum may be weighted by the number of other pairs. Some embodiments may then associate a respective n-gram weight with the respective n-gram in the vocabulary of n-grams. For example, some embodiments may determine that a first n-gram is associated with a second and third n-gram based on a set of n-gram pairs. The second n-gram may be only associated with the first n-gram and the third n-gram may be associated with the first n-gram and also associated with a fourth n-gram, fifth n-gram, and sixth n-gram. The n-gram weight associated with the first n-gram may be determined based on a sum of the connections to the first n-gram indicated by the pairs normalized by the number of other n-gram connections of each of the other n-grams of the pairs. For example, the association with the second n-gram may add "1" to the n-gram weight for the first n-gram based on the second n-gram not being in a pair with other n-grams and the second n-gram may add "0.25" to the n-gram weight of the first n-gram based on the third n-gram splitting its connection contribution amongst four different n-grams that include the first n-gram. Some embodiments may then update each contribution to the n-gram weight by an initial weight of the second and third n-grams to determine the n-gram weight of the first n-gram. Additionally, some embodiments may perform one or more of the operations described above using linear mathematical operations when determining an n-gram score.

After determining scores for n-grams in the vocabulary of n-grams, some embodiments may then determine a plurality of n-gram sequence scores by determining a respective n-gram sequence score for each respective n-gram sequence of the plurality of n-gram sequences. In some embodiments, the subset of n-gram weights may be associated with the subset of n-grams that form the respective n-gram sequence. For example, some embodiments may determine a sum of the individual n-gram scores of a sentence and set the n-gram sequence score to be the sum of the scores. Alternatively, or in addition, some embodiments may perform other operations to determine an n-gram sequence score, such as determining a product, an exponential value, logarithmic function, some combination thereof, or the like.

Some embodiments may use a neural network model to select a plurality of n-gram sets, where the n-gram sets may be sequences of n-grams (e.g., phrases or sentences). The neural network model may be trained to determine whether or not a set of n-grams is likely to include an answer to a query based on a training set of sequences. For example, some embodiments may use a feed-forward neural network with a backpropagation mechanism to determine a probability score that a sequence of n-grams of would include an answer to a user query. As described elsewhere in this disclosure, the model parameters of the neural network may be transferred from a previous data source. Alternatively, or in addition, the model parameters of the neural network may be trained based on domain-specific data or provided based on a set of domain expert analysis. Furthermore, an indicated domain category value associated with an ontology may be an input of the neural network, where different probability scores may be provided for the same sequence of n-grams by using different domain category values.

As stated elsewhere in this disclosure, some embodiments may use a set of ontology graphs or data related to a set of ontology graphs to modify a set of n-gram weights or other values associated with an n-gram. For example, some embodiments may determine whether an n-gram maps to a vertex of an ontology graph. In response to a determination that the n-gram maps to the vertex, some embodiments may update the weight associated with the n-gram. For example, some embodiments may update the n-gram weight by increasing the n-gram weight. Additionally, some embodiments may store the updated n-gram weight based on a domain-specific criterion. For example, some embodiments may store data in a first index specific to a first domain category value. Some embodiments may then determine whether an n-gram of a document maps to a vertex of an ontology graph that is categorized with the first domain category value. In response to a determination that the n-gram maps to the vertex associated with the first domain category value, some embodiments may update the weight associated with the n-gram. Otherwise, some embodiments may leave the n-gram weight unmodified, even if the n-gram maps to another vertex of a different ontology graph. By updating weights based on different ontologies, some embodiments may generate different indexed questions for users associated with different domains or different domain category values.

As disclosed elsewhere in this disclosure, some embodiments may access different indices or different portions and index based on a user context parameter, such as one identifying a domain category value. Alternatively, or in addition, some embodiments may apply different scoring systems based on a user context. For example, some embodiments may use a first scoring model to determine scores for a set of sentences of a document, where the scores may indicate a predicted relevance to a first topic. Some embodiments may then use a second scoring model to determine a different set of scores for the same set of sentences of a document, where the second set of scores may indicate a predicted relevance to a second topic.

In some embodiments, the process 1600 may include selecting one or more n-gram sets based on the set of scores, as indicated by block 1616. Some embodiments may select n-gram sets based on a score threshold, where an n-gram set having an n-gram set score greater than the score threshold is selected for use when generating a query, as further described below. Some embodiments may select n-gram sets based on a ranking result of the set of scores. For example, some embodiments may determine a score for each sentence or other n-gram sequence in a plurality of n-grams sequences. Some embodiments may then rank scores and select the greatest or least m scores, where m may be any non-negative integer greater than zero.

In some embodiments, the process 1600 may include generating a set of queries based on the selected n-gram set(s), as indicated by block 1620. As discussed elsewhere in this disclosure, some embodiments may generate text from other text. Some embodiments may use one or more of the methods described in this disclosure to generate a set of queries based on n-grams of the one or more n-gram sets selected above, such as one or more of the text summarization models described above. For example, some embodiments may use a neural network model having one or more attention mechanism implementations to generate text from a sequence of n-grams.

Some embodiments may generate a query after being provided with a set of n-grams selected from a document by determining a set of embedding vectors based on the selected n-grams using a transformer neural network model. For example, some embodiments may use a transformer neural network model that includes one or more attention mechanisms to generate a query based on n-grams from the sentence, "promise-based architecture are the backbone of the modern internet." Using a transformer neural network may include determining a set of attention values based on an attention query value and a attention key value, where the attention query and attention key values may be based on a matrix or other data structure constructed based on similarity scores determined between positions of an input sequence of n-grams or their corresponding learned representations. Some embodiments may determine a set of attention values based on a random feature map and use the set of attention values to generate or update a query. For example, some embodiments may determine embedding vectors for the n-grams of the query using an encoder neural network and generate a first random feature map based on the set of embedding vectors using a feature map function. In some embodiments, using the feature map function may include generating a first set of random or pseudorandom variables and multiplying at least one variable of the first set of random or pseudorandom variables with the at least one element of the set of embedding vectors.

As described elsewhere in this disclosure, some embodiments may perform similar operations to determine a set of positional encoding vectors and use the positional encoding vectors in combination with the embedding vectors to determine a set of attention values. Additionally, some embodiments may update a respective element of a set of attention vectors based on the attention vector element corresponding with a respective n-gram, where the respective n-gram or its learned representation is found in an ontology. For example, if an attention value for a first n-gram is initial the value "0.05," some embodiments may determine that the first n-gram maps to a vertex of an ontology graph and, in response, increase the attention value to "0.07." Some embodiments may then generate a query using the neural network based on the set of attention values. For example, some embodiments may use a neural network having neural network layers that use one or more of the sets of attention values as inputs to predict n-grams for a masked set of n-grams. Additional n-grams or to determine new n-grams for use as substitute n-grams for n-grams of a user-provided query.

Some embodiments may implement transfer learning to increase the speed required to train a neural network model and the accuracy of the trained model. Furthermore, some embodiments may use a unified text model when performing a plurality of the operations described in this disclosure. For example, some embodiments may use a Text-to-Text Transfer Transform (T5) architecture, such as that described in Raffel et al. (Raffel, C., Shazeer, N., Roberts, A., Lee, K., Narang, S., Matena, M., Zhou, Y., Li, W. and Liu, P. J., 2019. Exploring the limits of transfer learning with a unified text-to-text transformer. arXiv preprint arXiv:1910.10683), which is incorporated herein by reference. For example, some embodiments may use a set of learned representations that was first generated for one set of operations, such as text summarization operation, to perform another set of operations, such query generation operations. Using a system based on the T5 architecture or other unified transfer learning model may include using a variety of data types from a previous dataset that may or may not be similar to a text document being processed by a text generation model. For example, some embodiments may train a text generation model that was initialized with a pre-trained model, where some embodiments may then perform a reduced-scope training operation for specific text generation tasks such as text summarization or query generation.

Some embodiments may generate multiple queries based on a set of ontology graphs and the natural-language text of a document. For example, some embodiments may generate a plurality of queries based on the phrase "parabolic geometry is useful in this scenario." Some embodiments may first use one or more natural-language processing operations to associate the n-gram "scenario" with an n-gram used in another sentence, such as "distance determination." Some embodiments may generate a plurality of computer-generated natural-language queries using one or more of the operations described in this disclosure, where a first natural-language query recites, "what is parabolic geometry useful for" and a second natural-language query recites, "what is useful for determining distances?"

Some embodiments may generate or update one or more queries based on a set of ontologies in combination with a user context, where a user context may indicate a domain, class of the domain, another domain category value, or other parameters. Using a context to generate or update a query may include performing a query expansion operation as described elsewhere in this disclosure to generate or update the query. For example, some embodiments may update a computer-generated query, "what is parabolic geometry useful for?" based on a first ontology graph categorized with the domain category value "mathematics." By referencing the first ontology graph or an index based on the first ontology graph, some embodiments may recognize the term "parabolic geometry" as mapping to a vertex of the first ontology graph that is associated with a second vertex of the ontology graph. For example, the second vertex may represent the concept "Euclidean geometry," where the second vertex may directly map to the alternative n-gram "Euclidean geometry." Some embodiments may then update the first computer-generated query to recite, "what is Euclidean geometry useful for?" By performing a query expansion operation that includes generating or updating an n-gram of a natural-language query with a set of alternative n-grams associated with the other vertices of an ontology via a set of shared concepts, some embodiments may increase the likelihood of generating natural-language queries that will be similar to queries provided by a user.

Some embodiments may generate different queries based on a user context parameter by selecting or updating a text generation model based on the user context parameter. For example, some embodiments may use a first neural network model corresponding to a first context parameter associated with a first type of user profile. The first neural network model may include five encoder neural network layers to generate embedding vectors of n-grams and five decoder neural network layers to generate a set of decoded n-grams based on the embedding vectors, where the decoded n-grams may be used for a computer-generated query. Some embodiments may then use a second neural network model having ten encoder neural network layers and ten decoder neural network layers to generate queries corresponding to a second context parameter associated with a second type of user profile.

Some embodiments may generate or otherwise update one or more queries based on a set of n-grams of a summary, such as a summary generated using one or more of the embodiments described in this disclosure. For example, some embodiments may use an abstractive summarization model, such as a pointer generation network model to generate a summary of a document. Some embodiments may then generate a query from the summary by performing one or more of the operations described in this disclosure. For example, some embodiments may segment a summary into a sequence of n-grams. Some embodiments may then assign scores to each sequence of n-grams, select queries based on a determination of which sequences of the set of n-gram sequences satisfy a sequence score threshold, and generate a query based on the selected n-gram sequences. Some embodiments may be able to account for further variations in a query by generating multiple queries based on abstractive summaries, which may include phrases or summarizing statements that are not present in the document being summarized.

Some embodiments may generate or otherwise update one or more queries based on a history of previously-used or previously-generated queries. Some embodiments may access a history of queries via a database, where the history may include both the queries and the set ontologies used to generate or update a query. Some embodiments may then determine a vocabulary of the n-grams used to generate the queries ("query n-grams") and sort the query n-grams based on a parts-of-speech library. For example, some embodiments may analyze a history of queries to categorize the n-grams of the queries into nouns, pronouns, verbs, adjectives, or the like. Some embodiments may then determine a count of the n-grams and generate or update a text-generation model based on the count of n-grams used. For example, some embodiments may generate a history-specific vocabulary including a first query n-gram or text structure categorized as a "why" query indicating that a query is requesting information on the cause of a subject matter. Some embodiments may then perform operations to generate a "why" query by selecting the first query n-gram and replacing an n-gram of a query with the first query n-gram. Alternatively, or in addition, some embodiments may combine different query n-grams or different query structures when generating a new query or update an index based on a computer-generated query.

As described elsewhere in this disclosure, some embodiments may retrieve multiple documents based on a query. For example, some embodiments may perform one or more of the operations above to obtain another plurality of n-gram sets of a second document, such as another plurality of sentences of the second document. Some embodiments may perform one or more operations described above to determine a second set of scores corresponding with each n-gram set of the second plurality of n-gram sets, where the second set of scores is determined using a same scoring model as the model used to generate the first set of scores. Some embodiments may then select a second n-gram set based on the second set of scores using a set of operations similar to or the same as those described above. Some embodiments may then use a text generation model to generate a query based on both a first n-gram set of a first document and the second n-gram set of the second document. The query may then be used to update an index to map the query to at least one of the first document or the second document.

In some embodiments, the process 1600 may include determining a set of learned representations based on the set of computer-generated queries, as indicated by block 1624. As discussed elsewhere in this disclosure, some embodiments may determine a set of learned representations such as singular values or vectors in a vector space using one or more learning models. For example, as discussed elsewhere in this disclosure, some embodiments may determine a set of embedding vectors for each word or other n-gram of a document. Some embodiments may generate a set of phrase vectors or a set of sentence vectors for phrases or sentences. In some embodiments, each type of vector may correspond with a different vector space. For example, embedding vectors for n-grams may correspond with a first vector space and sentence vectors may correspond with a second vector space having a different number of dimensions. Some embodiments may generate a learned representation, such as a vector, to represent a query. As disclosed further below, some embodiments may then determine a similarity score between the learned representation of the computer-generated query and a user-provided query.

In some embodiments, the process 1600 may include updating an index to map a first set of learned representations to the first document, as indicated by block 1628. As discussed elsewhere in this disclosure, some embodiments may use an index, where an index may include a set of features that are usable to indicate document content in order to increase the efficiency of a search operation. Some embodiments may store the entirety of the computer-generated query in the index or otherwise associate the index-stored value with the text of the computer-generated query. Alternatively, or in addition, some embodiments may store a learned representation of the computer-generated query in the index. In some embodiments, the index may be stored in the form a set of linked pairs or triplets of values, where each pair or triplet may be a record of the index that maps different values, identifiers, pointers, or other types of information. Some embodiments may update an index to include a record that maps a learned representation of a computer-generated query with the text position of text used to generate the query, the first document itself, or another value associated with the first document.

One or more of the updated indices may stored in various other forms that may increase the speed of data retrieval, such as in the form of a self-balanced search tree, another type of m-ary tree, a trie, or the like. Furthermore, as described elsewhere in this disclosure, different indices or different sections of an index may be accessed based on a context parameter associated with one or more users. For example, some embodiments may include user profiles that categorize users as being associated with at least one of three different domains of knowledge, labeled with the list of category values '["infrastructure", "cybersecurity", "development"].' As described elsewhere in this disclosure, some embodiments may update an index based on the data associated with an ontology categorized with the domain (e.g., based on vertices and edges of an ontology graph). For example, some embodiments may determine that a computer-generated query is includes a first n-gram mapping to a vertex of an ontology graph labeled with the category "infrastructure," where the first n-gram is associated via a graph edge to a second vertex mapping to a second n-gram. Some embodiments may then generate a second query that includes the second n-gram. Some embodiments may then update a first index associated with the category "infrastructure" without updating a second index associated with the category "cybersecurity," where updating an index may include generating or modifying tree nodes of a search tree. For example, some embodiments may update a trie to include an additional set of tree nodes that collectively store an additional key value and a leaf node storing or pointing to an identifier of a document, where the identifier may include a position of the n-gram sequence used to generate the first computer-generated query.

As described elsewhere in this disclosure, various operations may be performed to retrieve related n-grams of an initial set of n-grams using an index. Some embodiments may search through a self-balancing search tree based on a key, where the key may be an n-gram or a learned representation of the n-gram. Some embodiments may search through the self-balancing search tree by starting at a root of the self-balancing search tree and recursively traversing tree nodes using the key to retrieve a second n-gram or corresponding embedding vector at a leaf node of the self-balancing search tree. Alternatively, or in addition, some embodiments may use an index stored in the form of a trie (i.e. prefix tree), where the trie may be associated with a first ontology and a second ontology such that it may be retrieved from a database or other data structure with identifiers of the first and second ontology. Some embodiments may traverse nodes of the trie based on an n-gram of the initial set of n-grams to retrieve a second n-gram, where the second n-gram may be part of a different ontology. By using an index connecting n-grams or representations of n-grams between different ontologies, some embodiments may accelerate the speed of data retrieval, text summarization, or other operations described in this disclosure.

Some embodiments may perform a local search through the document based on the set of computer-generated queries to retrieve one or more sections of text or other data and then map these sections of text or other data to the computer-generated query. For example, some embodiments may generate a first query "how do I manage apple trees" based on a first n-gram set comprising the sequence of n-grams "apple tree management." Some embodiments may then use the first query to retrieve text data from the document and determine that a first text section by the starting and ending positions ["15031", "23162" ] of the document "doc101x.doc" is most likely to include text relevant to this query. Some embodiments may then update the nodes of an index to map a learned representation of the first query "how do I manage apple trees" to the document "doc101x.doc" and the starting and ending positions ["15031", "23162" ].

As described elsewhere in this disclosure, an index such as a prefix tree, self-balanced search tree, m-ary search tree, or the like may be loaded into a cache memory to increase data retrieval speeds when updating the index or retrieving data from the index. As described elsewhere in this disclosure, a cache memory may include an L1 cache, L2 cache, L3 cache, where different types of cache memory systems may indicate different levels of available memory or the speed of memory access. As described elsewhere in this disclosure, some embodiments may load one or more elements of an index into cache memory in response to a determination that a user having a user context parameter associated with the index is using a computing device to perform one or more of the operations described in this disclosure.

In some embodiments, the process 1600 may include obtaining a user query, as indicated by block 1632. In some embodiments, the process of obtaining a user query may include one or more operations described above. For example, some embodiments may obtain a query during a data session between a client computing device and a server or other computer system executing one or more operations described in this disclosure. During the data session, a set of context parameters may be available via the set of account parameters or other data loaded during the data session. Similarly, as described above, a query made by a user may be used to generate one or more predicted values that may be included in the set of context parameters. For example, based on a match between a set of terminology used in a query and a set of terminology of a set of ontologies, a user may be assigned with the domain category values "entomologist" and "expert."

In some embodiments, the process 1600 may include determining a second set of learned representations based on the user query, as indicated by block 1636. Some embodiments may determine a set of n-grams using one or more operations described in this disclosure. For example, some embodiments may use some or all of the words of the query as n-grams either with or without a filtering operation(s) to modify the words. Some embodiments may use the same model to determine the second set of learned representations that was used to determine the first set of learned representations corresponding with the set of computer-generated queries. For example, some embodiments may have used a self-attentive neural network to determine a first sentence embedding based on a computer-generated query and then use the same self-attentive neural network to determine a second sentence embedding based on the query.

Some embodiments may determine a set of n-grams using one or more operations described in this disclosure. For example, some embodiments may use some or all of the words of the query as n-grams either with or without a filtering operation(s) to modify the words. Some embodiments may use a first model to determine the second set of learned representations, where the first model may have been used to determine the first set of learned representations corresponding with the set of computer-generated queries. For example, some embodiments may have used a self-attentive network to determine a first sentence embedding based on a computer-generated query and then use the same self-attentive network to determine a second sentence embedding based on the query.

In some embodiments, the process 1600 may include determining a similarity score based on the first and second set of learned representations, as indicated by block 1640. A similarity score may be used to indicate a semantic similarity between two learned representations or their corresponding sequences of n-grams. Some embodiments may determine a similarity score based on a difference between a pair of learned representations, such as a pair of integers, a pair of vectors, a pair of category values, or the like. For example, some embodiments may determine a first sentence vector based on a computer-generated query and a second sentence vector based on a user-provided query. Some embodiments may then determine a difference between the first and second sentence vectors and determine a distance (e.g., a Manhattan distance, Euclidean distance, another type of Minkowski distance) between the first and second sentence vectors and use the difference as a similarity score or otherwise base the similarity score on the distance. For example, some embodiments may determine a Euclidean distance between the first and second sentence vectors by determining a vector difference of a first and second sentence vector (i.e., subtracting the first vector from the second vector) and determining a root of squared sum of the elements of the resulting vector difference. Alternatively, or in addition, some embodiments may determine similarity using other metrics, such as providing a count of n-grams that are identical or share a root n-gram. For example, some embodiments may determine a similarity score between a computer-generated query and a user-provided query based on the number of n-grams that are shared between the two queries, where the similarity may be a sum of the number shared n-grams.

In some embodiments, the process 1600 may include determining whether the similarity score satisfies a set of criteria, as indicated by block 1644. In some embodiments, satisfying the set of criteria may include satisfying a similarity score threshold. For example, if the similarity score is provided as a distance value in a sentence embedding space, some embodiments may determine that the similarity score satisfies the set of criteria if the similarity score is greater than a similarity score threshold. A sentence embedding space may include a vector space having dimensions determined from a parameter-tuning operation, where differently-sized vector spaces may be used based on a corpus of text documents. Alternatively, or in addition, some embodiments may satisfy a set of criteria by having a minimum number or minimum ratio of shared n-grams. For example, after determining a similarity score between a computer-generated query and a user-provided query based on a shared number of n-grams, some embodiments may determine whether the similarity score satisfies a minimum ratio of shared n-grams or a minimum number of shared n-grams. If a determination is made that the similarity score satisfies the set of criteria, some embodiments may proceed to operations described for block 1646. Otherwise, operations of the process 1600 may proceed to operations described for block 1648.

In some embodiments, the process 1600 may include retrieving the document using the map to the first document stored in the index, as indicated by block 1646. The map to the first document stored in the index may be stored in the form of a record of a database, an array, a balanced search tree, another type of m-ary tree, a trie, or another type of index data structure. Some embodiments may load the index or a portion of the index based on a determination that a user is associated with a context value mapped to the index or the portion of the index. For example, a user associated with the domain category value "cardiology" may be provided with a first index assigned to users associated with the domain category value "cardiology."

Some embodiments may use the first set of learned representations to retrieve the first document via the index. For example, some embodiments may, after a determination that a learned representation of a user-provided query is sufficiently similar to a learned representation of a computer-generate query, use the first learned representation as a key to access the index. Using the key may permit some embodiments to retrieve a value mapped to the key, where the value may be an identifier of the first document or otherwise mapped to the first document. For example, using one or more of the operations described above, some embodiments may determine a similarity score based on a difference between a first sentence vector "[12, 53, 0]" and a second sentence vector "[13, 53, 1]." After a determination that the similarity score satisfies a similarity threshold, some embodiments may use the first sentence vector as a key to access an index in order to retrieve a link to a first document that is mapped to by the key. Using a sentence vector or another learned representation of a query as a key may include using the vector or other learned representation directly or using an output of a function that takes the learned representation as an input. For example, some embodiments may use the elements of a sentence vector to navigate through nodes of a search tree to reach a leaf node storing an identifier of a document and a text position of the document. Various operations may be performed when navigating through an index. For example, some embodiments may then retrieve a document via a trie by starting at a root of the trie and recursively traversing nodes of the trie using a key based on a first set of learned representations of the computer-generated query to reach a leaf node. In some embodiments, the leaf node may one or more types of values identifying a document or data in the document, such as a pointer to the document, an identifier of the first document, a section of text in the document, or the like. Alternatively, or in addition, some embodiments may compute a hash value of the vector and use the hash value as a key to navigate through an index. Alternatively, or in addition, some embodiments may use the n-grams of the query directly, where the sequence of n-grams may be a key of the index that leads to a document.

In some embodiments, the process 1600 may include retrieving a document without using the map of the first set of learned representations to the first document, as indicated by block 1648. Some embodiments may retrieve a document based on a user-provided query by performing a set of operations described elsewhere in this disclosure. For example, some embodiments may retrieve a document based on the user-provided query by replacing one or more n-grams of the query with an alternative set of n-grams, where the alternative set of n-grams may be determined via a set of ontology graphs. Alternatively, or in addition, some embodiments may use an index to retrieve a document, where a key of the index may be determined based on the second set of learned representations or some other value based on the user-provided query.

In some embodiments, the process 1600 may include displaying a search result in a user interface based on the user query, as indicated by block 1656. Some embodiments may display an n-gram sequence used to generate the query that led to the document being displayed in a UI being displayed on a screen of a user computing device or another computer system. In some embodiments, the UI element displaying the n-gram sequence may show the n-gram sequence surrounded by other text that neighbor the n-gram sequence. For example, if a first n-gram sequence is the first phrase "celery is green" and is in a first sentence stating, "the dog does not like the fact that celery is green and crunchy," some embodiments may provide a UI that displays the first sentence. The first phrase may be visually indicated and distinct from the surrounding text via highlighting, bolding, text font change, or some other visual indicator. Similarly, some embodiments may display tabular data, where rows, columns, or specific entries of the tabular data may be visually indicated in the UI.

As described elsewhere in this disclosure, some embodiments may use a set of ontologies to update a query used to retrieve one or more documents. Some embodiments may provide a web message, program instructions, or other data that causes a UI to display text from a document directly. For example, after obtaining a query "are cats dangerous," some embodiments may use one or more operations described in this disclosure to generate the query "feline danger assessment" and determine a learned representation based on the query "feline danger." Some embodiments may then use the learned representation as a key to retrieve a document and text positions in the document via an index that was generated using one or more computer-generated queries or corresponding learned representations. The UI may then be updated to display text indicated by the text positions, where the text may recite "assessments of feline danger." Some embodiments may highlight the text, where the word "feline" may be highlighted to indicate that it is associated with the word "cats" via an ontology graph.

As described elsewhere in this disclosure, some embodiments may display a sequence of related text sections of one or more documents. For example, as described above, some embodiments may retrieve a set of documents related to a first document. Some embodiments may cause a UI to display a first text section in the UI and a UI element permitting the display of other text sections in the UI. In some embodiments, the display of subsequent text sections may be visually depicted in various forms, such as cascading sheets, cards, a visualized pathway of text. For example, after obtaining a first query, some embodiments may display a set of text sections via a set of UI elements. A first UI element may include a first text summary of a first retrieved document and include an interactive component. The interactive component of the UI element may cause the UI to display a second text section or text summary of a second document after an interaction with a user, where the second text section may have been retrieved based on a user context parameter. For example, some embodiments may display the summarization "Malaria is a disease" in response to obtaining a query "is malaria a disease" via a UI box, where the UI box includes an interactive UI element that, upon interaction, may display a summarization of a second section of the first document. Alternatively, or in addition, an interaction with the interactive UI element may cause the display of a second document that is retrieved based on a user context parameter, such as an indicated preferred domain category value. For example, the UI element may cause the display of the sequence of n-grams, "your travel history indicates a risk of contracting Malaria," which may be obtained from a second document.

Figure 17:
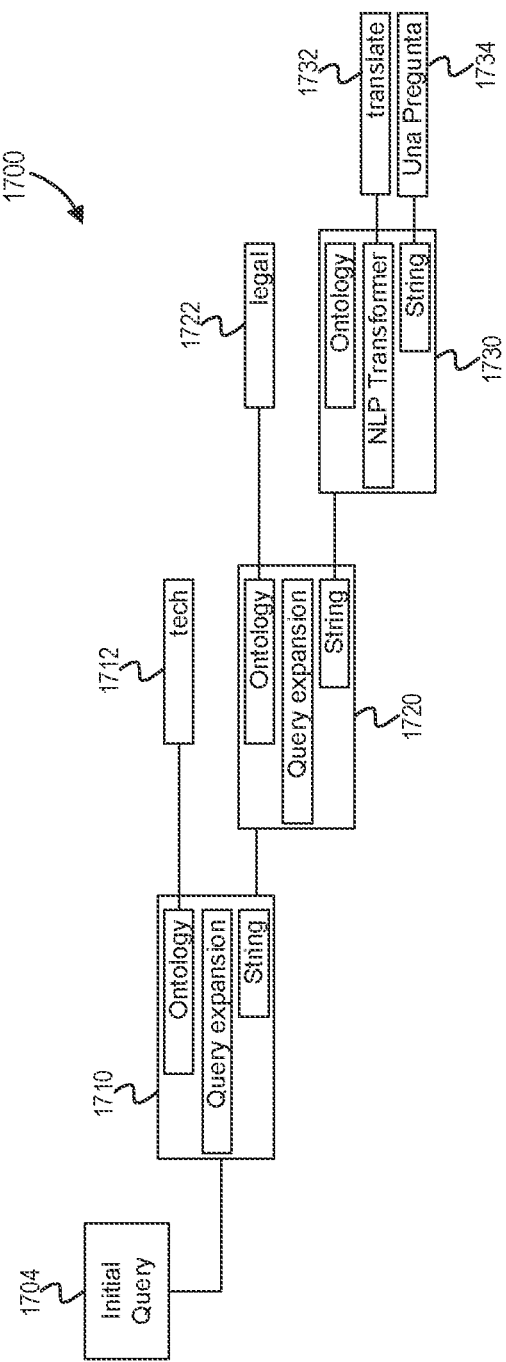
FIG. 17 is a conceptual diagram of a workflow for generating or otherwise updating a query, in accordance with some embodiments of the present techniques.

FIG. 17 is a conceptual diagram of a workflow for generating or otherwise updating a query, in accordance with some embodiments of the present techniques. The workflow 1700 displays a set of related subsystems by which a query may be generated or expanded. In some embodiments, an initial query 1704 may be obtained and include a computer-generated query or a user-provided query. After the initial query 1704 is provided by a user or generated by a computer system, some embodiments may perform a first set of operations represented by block 1710. When performing the first set of operations represented by block 1710, some embodiments may access a first ontology 1712 labeled with the domain "tech" to replace or augment one or more n-grams of the initial query 1704. Alternatively, or in addition, some embodiments may generate a set of additional queries based on the initial query 1704, where each respective additional query may use one or more n-grams mapped to by the first ontology 1712.

Some embodiments may then update the first query or generate a second set of queries based on a second set of operations represented by block 1720. When performing the second set of operations represented by block 1720, some embodiments may access a second ontology 1722 labeled with the domain "legal" to replace or augment one or more n-grams of the updated query with n-grams from the second ontology 1722. Alternatively, or in addition, some embodiments may generate a set of additional queries based on the updated query or initial query 1704, where each respective additional query may use one or more n-grams mapped to by the second ontology 1722. Some embodiments may further update the initial query 1704 based on n-grams indicating a shared or otherwise related concept between the first ontology 1712 and the second ontology 1722.

Some embodiments may then update the first query or generate a third set of queries based on a third set of operations represented by block 1730. Performing the third set of operations may include using a transformer neural network or other neural network. For example, some embodiments may use a transformer neural network 1732 to translate a query into a translated query 1734. Other embodiments may perform other operations with other transformers, such as generating a text summary, generating a query, or the like.

Figure 18:
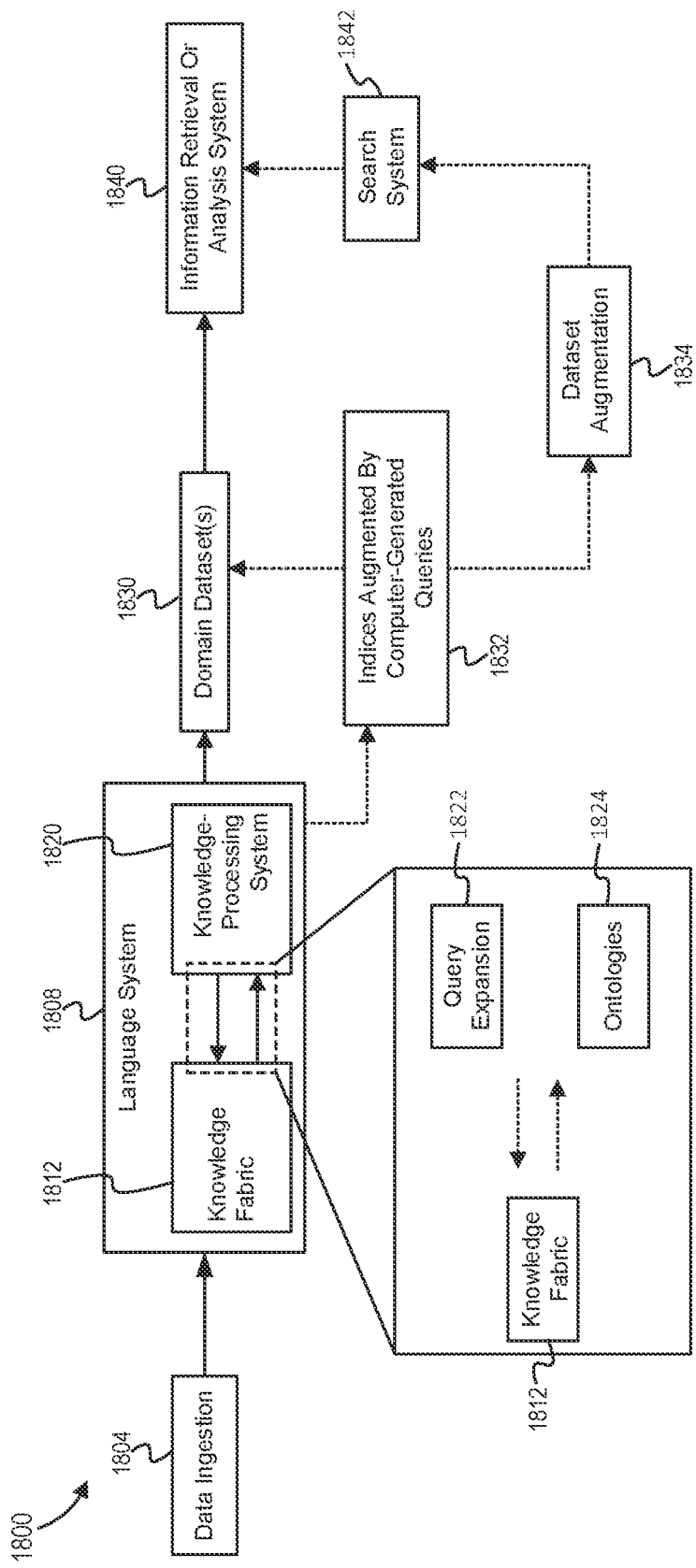
FIG. 18 is a logical architecture indicating data flow through a data ingestion system, ontology-based language system, domain datasets, and information retrieval system, in accordance with some embodiments of the present techniques.

FIG. 18 is a logical architecture indicating data flow through a data ingestion system, ontology-based language system, domain datasets, and information retrieval system, in accordance with some embodiments of the present techniques. The logical architecture 1800 includes a data ingestion system 1804, where the data ingestion system 1804 may perform one or more operations described in this disclosure to obtain one or more documents of a corpus of documents. Some embodiments may also use the data ingestion system 1804 to perform one or more operations to obtain other types of data such as image data, video data, interactive media data, or the like. Some embodiments may then perform one or more operations to augment the other types of data with associated text data, such as transcripts of audio generated from video or interactive media data, words recognized from an image, or the like.

After ingestion, some embodiments may provide the data to the language system 1808, where the language system 1808 may include a knowledge fabric that includes the ingested data. In addition, some embodiments may use a data augmentation system to associate or augment the corpus using a knowledge-processing system 1820. Using the knowledge-processing system 1820 may include generating or updating a set of ontologies 1824 based on the knowledge fabric 1812, where the set of ontologies 1824 may then be used to indicate or update data associated with the knowledge fabric 1812. Various other operations may be performed by the knowledge-processing system 1820 to increase the speed and accuracy of data retrieval and analysis operations on the knowledge fabric 1812. Such operations may include determining one or more sets of embedding vectors of documents in the knowledge fabric 1812, performing one or more query expansions with a query expansion subsystem 1822, or the like.

The language system 1808 may be used to provide a set of domain datasets 1830. The set of domain datasets 1830 may include data from the knowledge fabric 1812 augmented with data provided by the knowledge-processing system 1820. Some embodiments may then access the set of domain datasets 1830 when using the information retrieval or analysis system 1840. As described elsewhere in this disclosure, some embodiments may further augment the set of domain datasets 1830 with a set of indices 1832, where the set of indices 1832 may have been generated by the language system 1808 using one or more operations described in this disclosure. For example, the language system 1808 may generate a set of queries based on text from documents in the knowledge fabric 1812, where some embodiments may generate or update the set of indices 1832 based on the set of queries. Some embodiments may further augment the set of domain datasets 1830 with the domain-specific data set augmentation system 1834 to include data specific to an application, where the application may use or modify the information retrieval or analysis system 1840. Some embodiments may use the information retrieval or analysis system 1840 by using a search system 1842, where the search system 1842 may obtain a query or provide text or other data in response to a query. As described elsewhere in this disclosure, the provided data may include the set of domain datasets 1830, other data stored in the knowledge fabric 1812, other data provided by the knowledge-processing system 1820, other data stored in the language system 1808, other data ingested by the data ingestion system 1804, or the like.

V. Ontology-Augmented Interface

A user interface (UI) allows users of varying expertise to update ontology graphs or other data described in this disclosure. A UI may include UI elements that display text or other information, provide a way for a user to provide inputs, reconfigure the UI, provide a means for a user to interact with a program in communication with the UI, or perform other operations. A text-displaying UI may include features that increase the efficiency of navigating and viewing information stored in a document, such as a scrollbar, a text search function, word highlighting, or the like. However, a UI that does not include visual indicators or otherwise detect text based on domain-specific data may increase the difficulty of adapting a document for viewing by different users. In addition, a UI that indicates n-grams mapped to domain-specific ontologies may be less comprehensible or useful for document comparison operations or operations to provide users with a way to update domain-specific ontologies.

Some embodiments described in this disclosure may update a weight, bias, or other model parameter associated with an n-gram mapped to a vertex of an ontology graph. As described elsewhere in this disclosure, an update to a n-gram in a UI may update an association between a first n-gram and an ontology graph by generating a vertex mapped to the first n-gram, deleting the vertex, or modifying the vertex. The update to the n-gram may cause additional updates to other operations, such as updates to one or more machine learning operations, query expansion operations, document retrieval operations, or the like. For example, as further described below, some embodiments may update a machine learning operation based on an update to a text document in a user interface. By augmenting a user interface with an updated ontology graph, some embodiments may reduce the computation time required to perform dynamic, user-specific content display in a user interface. Such time reductions may be especially helpful when dealing with large corpora of data, such as corpora having more than 1000 documents, more than 100,000 documents, or more than 1,000,000 documents.

Some embodiments may accelerate or otherwise improve the efficiency of one or more operations described in this disclosure by updating ontology-specific indices or domain-specific indices based on interactions with a UI. As described elsewhere in this disclosure, an index may map n-grams to other n-grams and may be indicated as accessible to a set of user accounts or categories associated with user accounts. By updating an index based on one or more updates caused by interactions with a UI, some embodiments increase the accessibility and ease for a domain expert to create or maintain an ontology that is then usable to generate visual indicators of text associated with an ontology.

In some embodiments, as described elsewhere in this disclosure, a UI may provide users with the ability to graphically update a data ingestion or processing workflow. For example, some embodiments may provide users with a UI that represents a workflow as a set of workflow blocks. The workflow blocks may represent operations, models used during the operations, corpora ingested during the operations, arguments used during the operations, or other elements of a workflow. Different configurations of the workflow blocks or other UI elements may indicate an order of operations or relationships between embodiments, where a user may modify the configuration when sending instructions to update a workflow.

Figure 19:
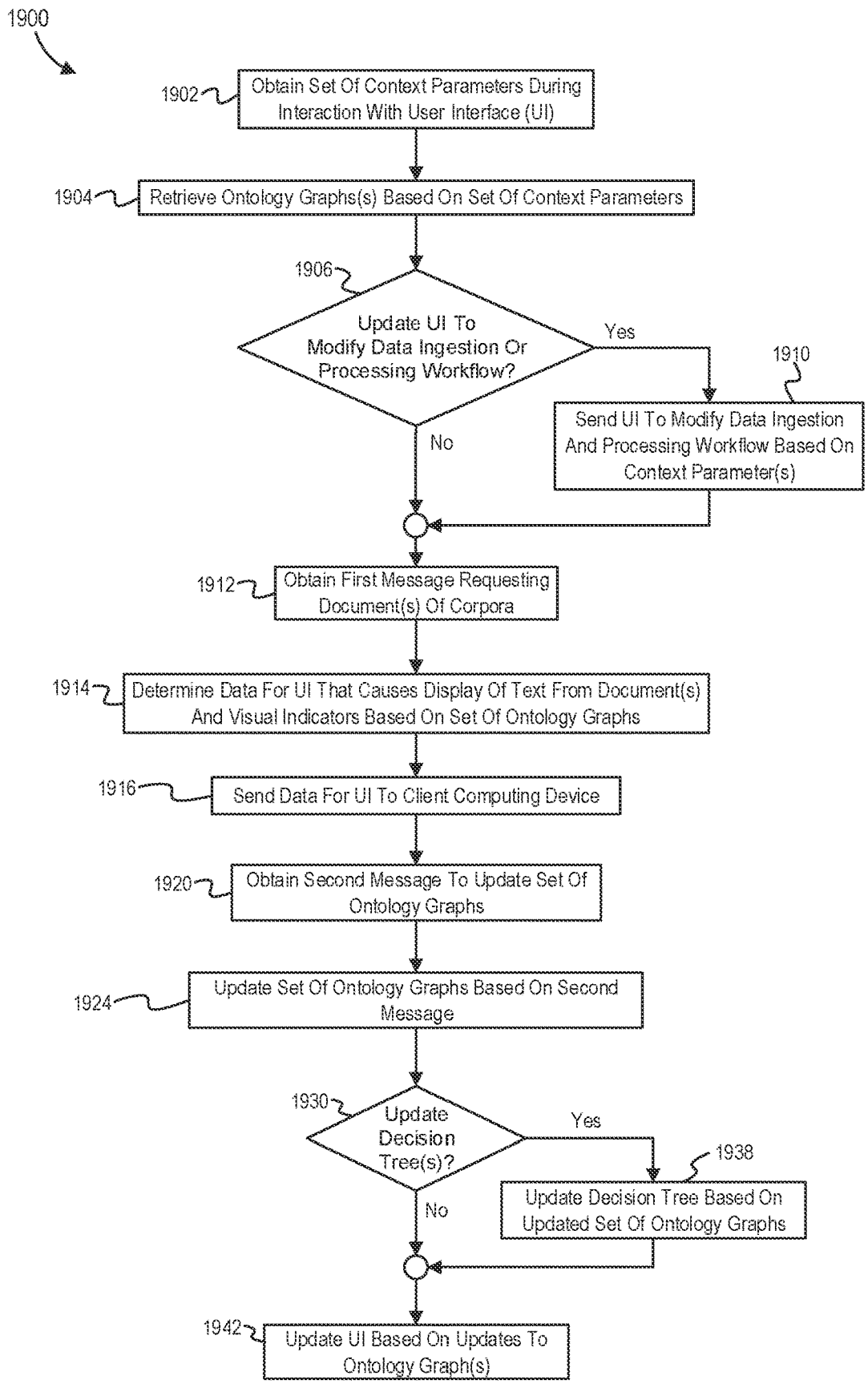
FIG. 19 is a flowchart of operations to for updating a user interface for displaying text of a document, in accordance with some embodiments of the present techniques.

FIG. 19 is a flowchart of operations to for updating a user interface for displaying text of a document, in accordance with some embodiments of the present techniques. Operations of the process 1900 may begin at block 1902. In some embodiments, the process 1900 may include obtaining a set of context parameters, as indicated by block 1902. As described elsewhere in this disclosure, a set of context parameters may be obtained from a user account and may include a set of account parameters associated with the respective user identified by the user account. For example, a user may be logged into a corresponding user account during a data session between a client computing device and a server, where messages sent between the client computing device and the server may identify a user account. The set of user account parameters may include one or more categories indicating a domain of expertise, a domain class within a domain of expertise, another type of subdomain within a domain, other domain category values, or the like. Furthermore, as described elsewhere, some embodiments may also obtain one or more context parameters based on a query or other history of activity associated with a user. For example, based on a set of words provided by a user in a history of queries, some embodiments may determine that a user is associated with a first domain and its corresponding ontology graph.

In some embodiments, the process 1900 may include retrieving a set of ontology graphs based on the set of context parameters, as indicated by block 1904. As described elsewhere in this disclosure, the set of context parameters may directly identify one or more ontology graphs available to a user. Alternatively, or in addition, some embodiments may determine a set of user roles or other user categories associated with a user and determine a set of ontology graphs based on the set of user roles or other user categories. For example, some embodiments may determine that a user account is labeled with the user role "Level 4 specialist," and retrieve a set of ontology graphs for use. Some embodiments may distinguish between a first and second set of ontologies, where a user may have read-level access for the first set of ontologies, and where the user may have read-write-level access to the second set of ontologies. For example, some embodiments may retrieve a first and second set of ontology graphs. A user may read one or more documents labeled with n-grams of the first ontology graph but not be permitted to edit the first ontology graph, whereas the same user may be permitted to update the second set of ontology graphs by adding additional words, phrases, or other n-grams.

In some embodiments, the process 1900 may include determining whether to update a UI for updating a data ingestion or processing workflow, as indicated by block 1906. Some embodiments may determine that a user is attempting to update a data ingestion processing workflow based on a message provided by a client computing device being used by the user. For example, some embodiments may receive a web message from a client computing device indicating that a user is requesting access to a UI window or other UI element to update a data ingestion or processing workflow. In response, some embodiments may determine that the UI should be updated to permit the modification of a data ingestion or processing workflow. Some embodiments may first determine whether the user has an appropriate permission or user role to update a data ingestion or processing workflow. For example, a user having the user role "data engineer" may be permitted to update a data ingestion or processing workflow, whereas a user having the user role "tourist" may be prevented from updating a data ingestion or processing workflow. If a determination is made that a UI should be updated to modify a data ingestion or processing workflow, operations of the process 1900 may proceed to block 1910. Otherwise, operations of the process 1900 may proceed to block 1928.

In some embodiments, the process 1900 may include sending a UI to modify a data ingestion and processing workflow based on the set of context parameters, as indicated by block 1910. Operations to update the data ingestion and processing workflow may include one or more of the operations described further below for the process 2000. For example, some embodiments may store the data ingestion and processing workflow in the form of block text obtain a higher-level language. The data ingestion and processing workflow may be stored in various forms and may be stored in a pre-compiled form that is then used to generate compiled machine language code or a graphical UI. For example, some embodiments may receive a web message indicating that a user wishes to access a first workflow. Some embodiments may then retrieve a dataset representing a data ingestion and processing workflow. For example, some embodiments may retrieve data encoded a YAML format including square brackets and curly brackets.

In some embodiments, the process 1900 may include obtaining a first message requesting a set of documents of corpora, as indicated by block 1912. As discussed elsewhere in this disclosure, a message requesting a set of documents may be provided in the form of a query without identifying a specific document, where some embodiments may send the document in response to the query. For example, some embodiments may obtain a first message including a query for a document that includes the question, "what are the side effects of aluminum?" In response, some embodiments may retrieve a plurality of documents based on the query. Alternatively, or in addition, some embodiments may receive a message directly identifying the document. For example, some embodiments may obtain a message including an identifier for a document and, in response, directly send the document to the client computing device so that it may be rendered for viewing in a UI.

In some embodiments, the process 1900 may include determining data for a UI that causes the display of text from the set of documents and a set of visual indicators based on the set of ontology graphs, as indicated by block 1914. Some embodiments may send the data in a plurality of packets, where a message may be distributed across a plurality of packets. For example, some embodiments may send data over a plurality of request-response exchanges between a server and a client computing device. Some embodiments may provide some or all of the data using a set of third-party services, such as a content delivery network (CDN). For example, some embodiments may send UI data to a client computing device via a CDN over multiple responses that are part of a set of request-response exchanges, where the data may include text data, image data, metadata associated with other data, or the like.

Some embodiments may send UI data that includes program code that, when executed by a client computing device, causes the display of a UI, where the program instructions may include scripting code such as JavaScript code, pre-compiled program code such as web assembly code, or the like. For example, some embodiments may provide program code that causes a UI being displayed on a client computing device to render text from a natural-language text document, where the rendered text includes a set of visual indicators indicating one or more words or other n-grams that map to a set of vertices of an ontology graph. Furthermore, as described further below, some embodiments may send UI data that includes structured data interpretable by a native application that is already displaying a version of the UI, where the structured data may be used to update the display of the UI. For example, some embodiments may send a JSON file to a client computing device, where the client computing device may use a native application to interpret the JSON file and update a UI based on the JSON file. As described elsewhere in this disclosure, a visual indicator may include highlighting, text bordering, colored text, an animation, or the like. For example, some embodiments may display a paragraph of text, where a first word of the paragraph is highlighted in a first color to indicate that the first word is associated with an ontology via a vertex of the ontology.

Some embodiments may provide a UI that displays visual indicators associated with different ontologies. For example, a section of text being rendered for presentation by a UI may include a first n-gram "IgG" and a second n-gram "Child." A first visual indicator may indicate that the first n-gram is mapped to a vertex of a first ontology graph labeled with the domain "medical tests." A second visual indicator may indicate that the second n-gram is mapped to a vertex of a second ontology graph labeled with the domain "demographics," where the first and second visual indicators may use different colors, be surrounded with different borders, or otherwise be visually distinct from each other. For example, some embodiments may identify a vertex of a second ontology graph based on the second n-gram by determining an embedding vector based on the second n-gram and then matching the embedding vector with a set of embedding vectors mapped to vertices of the second ontology graph. Alternatively, or in addition, some embodiments may identify a vertex of an ontology graph by determining an embedding vector of the second n-gram, determining the closest embedding vector to the embedding vector of the second n-gram based on a distance in an embedding space, and select the vertex mapped to the closest embedding vector.

Alternatively, or in addition, a UI may display one or more n-grams and an associated set of visual indicators indicating that the set of n-grams is mapped to a plurality of ontologies or subdomains within the plurality of ontologies. For example, a UI may display an n-gram and a visual indicator indicating that the n-gram is mapped to vertices associated with different ontologies. Various configurations may be displayed in a UI to identify the set of ontologies associated with a visual indicator. For example, a first ontology identifier "domain 1" and a second ontology identifier "domain 2" may be displayed in a visual indicator surrounding an n-gram to indicate that the indicated n-gram is mapped to vertices of a pair of graphs identified by "domain 1" or "domain 2."

Some embodiments may provide a UI that includes one or more UI elements that may be interacted with to send a set of requests to a server based on an input or configuration of the UI. For example, the UI may cause the client computing device to send a second message to a computer system, where the second web message may include an n-gram indicated by a user and an update value corresponding with the n-gram, where the update value may indicate a change to a vertex or an addition to a vertex. Various types of updating operations may be performed, where the n-gram may be updated to be a different n-gram, may be associated with a new ontology graph, or the like. For example, the UI may include a UI element in the form of a button with the rendered text "submit changes."

After an interaction with the UI element by a user, the interaction may include a click with a cursor displayed on a computer monitor or tap on a touchscreen, a client computing device may provide a web message indicating one or more user-provided update. In some embodiments, the update may include a request to update an ontology. An ontology update request may include a request to update an n-gram mapped to the ontology, remove an n-gram from an ontology, or add an n-gram to an ontology. For example, an ontology update request may include a first n-gram, a domain category value, and a function argument indicating that the first n-gram should be removed from the ontology graph(s) categorized with the domain category value.

Some embodiments may provide a UI that indicates or permits a user to update relationship types between different vertices via n-grams mapping to the different vertices. Various UI element interactions may be used or combined to cause a client computing device to send a second message to update an ontology graph. For example, a user may highlight the word "coughing," drag the highlighted word to the word "tuberculosis" in the UI, and indicate that "coughing" is associated with "tuberculosis" via a first relationship type "relType1" selected from a dropdown menu of the UI. The user may then tap on a UI element such as a button labeled "submit," causing the client computing device to send a web message that includes the n-gram "coughing" and a set of update values including "tuberculosis" and "relType1" to a server performing one or more operations described in this disclosure. The client computing device displaying the UI may then send a web message that includes the highlighted n-gram and the set of update values, where the set of update values may indicate a change to a vertex or an addition to a vertex. Some embodiments may determine that an update value indicates a change to a vertex or an addition to a vertex based on the update value identifying a vertex. For example, the update value "tuberculosis" in the message described above may indicate that the update value identifies the vertex based on the update value "tuberculosis" identifying a vertex of an ontology graph. For example, as discussed further below, some embodiments may update a vertex such that the previous n-gram mapped to the vertex is replaced with a replacement n-gram identified by one or more of the update values.

Some embodiments may provide a UI that concurrently displays a first and a second natural-language text document. For example, some embodiments may provide a UI that displays a first text document that is a previous version of a second text document and concurrently display the first and second text documents for a document comparison operation. Alternatively, or in addition, some embodiments may provide a UI that presents the second text document, where text differences or other changes to the second text document with respect to the first text document may be indicated. In addition to indicating changes, some embodiments may indicate text differences associated with a domain category, generate or otherwise update a visual indicator to indicate the domain category, or notify a user that data associated with the domain category was updated. For example, an n-gram present in a first text document may be absent in a second text document, where the n-gram may be mapped to a first ontology associated with a first domain category. Some embodiments may then determine that the updated version changes one or more text sections associated with the first domain category based on the absent n-gram. In response, some embodiments may update a visual indicator to include an identifier of the domain category or notify a user that a text difference associated with the domain category has occurred.

As described elsewhere in this disclosure, a user account may include account parameters that indicate a set of domain category values. In some embodiments, the set of domain category values may be organized as a sequence of domain category values or otherwise be used to establish a hierarchy of domain category values for the user account. The hierarchy of domain category values may then be used to configure an arrangement of UI elements on a display. For example, some embodiments may provide a UI that displays a set of changes between two documents, where the set of changes include changes to text including n-grams associated with different domains or other categories. Some embodiments may then select which set of changes to prioritize and display above other changes based on a hierarchy of domain category values associated with a user account. For example, some embodiments may provide a UI that displays a first text section associated with the category "infectious disease" and a second text section associated with the domain category "organ failure." In response to a determination that a user account is associated with a hierarchy of domain category values prioritizing the category "organ failure" over the category "infectious disease," some embodiments may display the second text section visually associated with the first text section on a display screen of the UI. Being visually associated with the first text section may include being above the first text section and within a pixel range of the first text section, where the pixel range may include values less than 10 pixels, values less 50 pixels, values less than 100 pixels, values less than 200 pixels, or the like. Similarly, some embodiments may display the first identifier "organ failure" in visual association with the second identifier "infectious disease," such as by displaying the first identifier above the second identifier, where at least one character of the first identifier is within 100 pixels of a pixel of a character the second identifier.

Some embodiment may use a set of ontology graphs to determine if a set of expected n-grams are missing from a document. For example, some embodiments may determine whether a first set of n-grams mapped to a concept of an ontology graph is present in a document based on another n-gram mapped to the shared concept being present in the document as a set of alert criteria. In response to a determination that the first set of n-grams mapped to the first concept is not present in the document, some embodiments may determine that one or more alert criteria have been satisfied. Based on a determination that an alert criterion is satisfied, some embodiments may notify a user by sending a message via a messaging platform, updating a UI to display an alert message, sending a message to a user account, or the like. By using one or more ontology graphs to determine which n-grams to detect for a set of alert criteria, some embodiments may increase the adaptability of a system to detecting missing information for various documents by taking advantage of an ontology graph's structure with respect to associating disparate n-grams.

Some embodiments may use a set of ontology graphs to determine whether a text section of a document is repetitive and provide a metric of repetitiveness when providing or updating a UI. For example, some embodiments may count the number of n-grams of a set of n-grams mapped to a set of vertices are used, where each vertex of the set of vertices is associated with a shared concept. In response to a determination that the count satisfies an alert threshold (e.g. by exceeding the alert threshold) or some other alert criteria, some embodiments may notify a user. The use of a set of ontology graphs to measure repetitiveness or determine a set of alert criteria may reduce the memory requirements for measuring document repetitiveness. By using an ontology graph determined based on a set of context parameters, some embodiments may adaptively select which words and concepts to count based on a set of user account parameters. Furthermore, by using an ontology graph, some embodiments may determine semantic repetitiveness with greater accuracy.

Some embodiments may indicate one or more logical contradictions based on associations between vertices mapped to n-grams of a document. For example, some embodiments may store an ontology graph having a first vertex mapped to a first n-gram "condition1." The first vertex may be associated with a second vertex via a graph edge, where the second vertex may be mapped to a second n-gram "symptom1," and where the graph edge may be associated with relationship type "cause." Some embodiments may then receive an update message from a client computing device to update an ontology indicating that the "condition1" and "symptom1" are mutually exclusive. Some embodiments may then determine whether the pair of relationship types "cause" and "mutually exclusive" are included in a first list of relationship type pairs indicated as being contradictory. In response to a determination that the pair of relationship types "cause" and "mutually exclusive" are included in the first list of relationship type pairs, some embodiments may generate an alert notification based on a determination that the logical contradiction has been detected.

In some embodiments, the process 1900 may include sending data for the UI to the client computing device, as indicated by block 1916. As described elsewhere in this disclosure, sending a UI may include sending data interpretable by a web browser displaying a UI, a native application that includes the UI, or the like. In some embodiments, data associated with the UI, such as a bytecode version of the UI or components of the UI, may be sent to a computing device. For example, a web browser or other application executing on a client computing device may obtain a bytecode version that includes pre-interpreted libraries or frameworks and compile the bytecode to an executable binary encoding of the bytecode version. Some embodiments may store one or more functions based on an ontology graph in a bytecode format that is then sent to a client computing device, where the ontology graph or an index based on the ontology graph may be sent to the client computing device.

Alternatively, or in addition, some embodiments may provide UI data written in a markup language such as JSON, XML, or the like that may then be interpreted by a UI executing on a web browser, as a part of a native application, or another computing platform. For example, some embodiments may first provide a set of UI elements encoded in a pre-compiled bytecode format to a client computing device that may then be displayed on a web browser. After an interaction with a user, some embodiments may then send a set of structured data stored as a JSON document to indicate one or more updates to the UI. By storing and sending UI data in a structured data format, some embodiments may increase the reliability and transferability of UI configurations between different computing systems and users.

Some embodiments may reference the uncompiled or compiled version of the UI in a subsequent data session to reuse elements of the UI stored in a cache. For example, some embodiments may perform operations to copy ontology graph data or other data used by a UI from a first memory address space to a second memory address space, where the second memory address space may be in persistent memory. By copying data to a local persistent memory of a client computing device, some embodiments may reduce the network cost of rendering data stored in corpora or provide a means of performing one or more of the operations described in this disclosure without requiring a connection to a server.

In some embodiments, the process 1900 may include obtaining a second message to update the set of ontology graphs, as indicated by block 1920. Operations to obtain the second message to update the set of ontology graphs may include operations similar to those described for block 1912. As described elsewhere in this disclosure, the message to update the second set of ontology graphs may include instructions to update a vertex mapped to an n-gram, where the n-gram may be provided via the second message. For example, some embodiments may obtain the second message in the form of a web request sent by a client computing device that includes a first n-gram and a set of update values including a second n-gram and instructions to replace the first n-gram with the second n-gram. Some embodiments may obtain an n-gram of a message that directly includes the n-gram. Alternatively, or in addition, a message may include an n-gram by including an n-gram identifier that is different from the n-gram itself, such as a globally unique identifier (GUID) for a word. For example, some embodiments may obtain a message that includes the GUID "2151223x3126," where "2151223x3126" may be mapped to the n-gram "selectively."

In some embodiments, the process 1900 may include updating a set of ontology graphs based on the second message, as indicated by block 1924. Updating a set of ontology graphs may include adding, removing, modifying a variable of, or otherwise updating a vertex of the set of ontology graphs. Some embodiments may update a set of ontology graphs by updating a vertex of a first graph of the set of ontology graphs to change an associated n-gram from a first n-gram to a second n-gram. For example, some embodiments may, after receiving a message indicating an update to the n-gram "borscht" to an update value "borst," some embodiments may select a first vertex mapped to the n-gram "borscht." In some embodiments, the first vertex may be directly mapped the n-gram "borscht." Alternatively, or in addition, the first vertex may be mapped to the n-gram "borscht" via an embedding vector generated based on the n-gram "borscht." After selecting the first vertex, some embodiments may modify its associated n-gram with the update value "borst." Alternatively, or in addition, some embodiments may update the set of ontology graphs by updating indices generated based on the set of ontology graphs. For example, some embodiments may update a set of trie nodes of an index to replace the n-gram "borscht" with "borst."

In some embodiments, updating the set of ontology graphs may include adding a vertex to the set of ontology graphs. For example, some embodiments may receive a message indicating that an n-gram should be part of an ontology graph. Some embodiments may then determine whether the n-gram is already mapped to a vertex of an ontology graph. Based on a determination that the n-gram is not mapped to any vertices of the ontology graph, some embodiments may update the ontology graph to include a new vertex that maps to the n-gram. In addition to adding the new vertex to the ontology graph, as described elsewhere in this disclosure, some embodiments may also include associations between the new vertex and other vertices of the ontology graph.

As discussed above, updating the set of ontology graphs may include updating a set of graph edges of the ontology graph associated with an n-gram. For example, some embodiments may obtain a message indicating that a first n-gram mapped to a first vertex of a first ontology graph is associated with a second n-gram mapped to a second vertex of a second ontology graph. The message may include a first n-gram and a set of update values including the second n-gram and a relationship type between the first and second n-grams. In some embodiments, after receiving the message indicating the first n-gram is associated with the second n-gram, some embodiments may update a set of ontology graphs by adding an ontology graph edge that connects the first vertex with the second vertex. For example, some embodiments may access a list of graph edges consisting of an array of vertex identifier pairs representing graph edges and add a new vertex identifier pair to represent an association between the first and second vertices. Alternatively, or in addition, some embodiments may update an index based on the updated ontology graph.

Some embodiments may update a weight, bias, activation function parameter, or other neural network model based on user interaction with a UI. For example, some embodiments may receive a message from a client computing device based on a user interaction that indicates that the user interaction should generate or modify a relationship type between a first and second vertex of an ontology graph. By receiving a message indicating instructions to generate or modifying a relationship type based on a UI interaction between a pair of n-grams, some embodiments may generate or modify a graph edge or other association between the pair of vertices mapping to the pair of n-grams. Some embodiments may then update a machine learning model by update the training of the learning model based on the newly-generated or modified relationship type. For example, some embodiments may determine embedding vectors in an embedding space for an n-gram in a sequence of n-grams based on other n-grams of the sequence of n-grams. After determining that a graph edge between a corresponding pair of vertices mapped to the pair of n-grams has been generated or updated, some embodiments may change an n-gram weight or other value used to determine the embedding vector. In some embodiments, an update to the value used to determine the embedding vector may cause further updates to a set of neural network weights, biases, activation function parameters, hyperparameters, or other learning model parameters during a training operation of a machine learning model. Alternatively, or in addition, some embodiments may update model parameters of statistical models based on the user interaction with the UI.

In some embodiments, updating the set of ontology graphs, machine learning models, or other elements of program code may include compiling or recompiling program instructions. For example, as described elsewhere in this disclosure, some embodiments may perform querying operations based on the set of ontology graphs. Some embodiments may perform compiling operations when updating the set of ontology graphs. Various compiling systems may be used, such as a LLVM compiling system or multi-level intermediate representation (MLIR) compiler. For example, some embodiments may use a LLVM compiling system that compiles a source language to an intermediate representation (IR) and optimize the IR with an LLVM IR optimizer.

As described in this disclosure, an intermediate representation may include program instructions structured for further processing that is agnostic with respect to a source or target programming language. For example, an intermediate representation provided by the LLVM compiling system may provide a set of program code, where each respective instruction of the program represents a fundamental operation. The IR may be provided in one or more various forms, such as a three-address code, graph-based form, stack-based form, or some combination thereof. In some embodiments, program code to determine semantic relationships based on an ontology may be compiled into an abstract syntax tree or other IR. Furthermore, as discussed further below, some embodiments may use a compiler adapted for compiling machine learning operations, such as TVM.

In some embodiments, the process 1900 may include determining whether a set of decision trees should be updated, as indicated by block 1930. As described elsewhere in this disclosure, one or more decision trees or other decision system may be used by a user to determine what additional actions to take, to categorize a record, or to perform other operations. In some embodiments, the decision tree may be used as a form of natural language instructions, where updates to the decision tree may correspond with updates to natural language instructions based on the concepts associated with the decision tree. Unless otherwise stated, it should be understood that operations used to update a decision tree may be used to update other types of decision systems, and that other decision systems may be used instead of or in conjunction with a decision tree to provide a decision.

In some embodiments, data stored in a set of ontology graphs may affect the decision tree. Some embodiments may determine a set of decision trees that are affected by an update to a set of ontology graphs and whether the set of decision trees should be updated based on a set of categories indicated by the set of ontologies described above. For example, some embodiments may determine a set of domain category values based on the vertices being updated by a message sent from a client computing device, where the set of decision trees is associated with the set of domain category values. The domain category value may include an identifier for a domain of knowledge, a class within the domain of knowledge, an identifier of a concept or other subdomain, or the like. For example, some embodiments may update a first vertex of a first ontology graph based on a first n-gram, where the first ontology graph may be labeled with the domain title "medicine" with a domain class value "expert." After determining which domain categories have been updated, some embodiments may then determine a set of affected decision trees based on the ontology graph by selecting the set of decision trees associated with the updated categories "medicine" and "expert."

Some embodiments may first determine whether the updated domain is listed in a set of decision-impacting domains. In response to a determination that the updated domain is listed in the set of decision-impacting domains, some embodiments may update a decision tree associated with the updated domain. For example, some embodiments may determine that ontology graphs associated with the domain category "medicine" have been updated and then determine that the domain category "medicine" is listed in the set of decision-impacting domains. In response, some embodiments may determine that a first decision tree should be updated, where the first decision tree is listed in association with the domain category "medicine." Alternatively, or in addition, some embodiments may determine a set of decision tree nodes, each respective node corresponding to a respective decision tree of a set of decision trees based on the domain category value or an associated set of vertices.

Some embodiments may accelerate the speed of decision tree update operations by generating and maintaining an index that directly associates a domain category value with a set of decision tree nodes or other elements of a decision tree. For example, some embodiments may determine that a vertex associated with the domain category value "symptoms" has been updated. Some embodiments may then use an index that associates the domain category value "symptoms" with a set of affected decision tree nodes to determine that one or more decision trees should be updated. Alternatively, or in addition, some embodiments may use a set of values that are associated with vertices that identify a set of decision tree nodes. For example, some embodiments may access a first vertex representing a concept, where the first vertex may identify a set of decision tree nodes, and where each respective decision tree node corresponds with a different decision tree. After an update to the first vertex or an update to another vertex adjacent to the first vertex, some embodiments may then determine that a set of decision trees listed in association with the first vertex should be updated. If a determination is made that a set of decision trees should be updated, operations of the process 1900 may proceed to operations described block 1938. Otherwise, operations of the process 1900 may proceed to operations described for block 1942.

In some embodiments, the process 1900 may include updating a set of decision trees based on the updated set of ontology graphs, as indicated by block 1938. Updating a decision tree may include updating one or more elements of a decision tree such as updating a set of labels (e.g., a medical diagnosis), updating a decision operation represented by a decision tree node, updating a vocabulary of n-grams used by the decision tree, or the like. Various types of updates to a decision tree may be made. Some embodiments may update a decision tree by updating a set of n-grams used to make a labeling decision or associations between the n-grams used to make the labeling decision. The set of n-grams may be updated by replacing a previous n-gram of the set of n-grams with new n-gram, deleting an n-gram from the set of n-grams, adding an n-gram that causes the selection of a second n-gram at a decision tree node, or the like. For example, some embodiments may replace one or more previous n-grams in a set of n-grams used at an operation represented by a decision tree node to label a record, such as by replacing the n-gram "hypertension" with the n-gram "hypertensive crisis" in response to a user's interaction with a UI. Some embodiments may then update logic corresponding to a decision tree node based on the update to the set of ontology values. For example, after an update to the decision tree, some embodiments using the updated decision tree may assign the diagnostic label "emergency" to a patient after a user selects the term "hypertensive crisis" using a medical diagnosis program.

In some embodiments, an updated decision tree may be used by an engine to label data. For example, an updated decision tree may be interpreted by a rules engine to label a medical record with a diagnosis based on an ontology graph or n-grams mapped to the ontology graph. In some embodiments, a decision operation represented by a decision tree node may use selected n-grams of different sets of n-grams to determine a label or another decision tree decision result. For example, some embodiments may use logic corresponding with a decision node that determines whether a patient has the diagnosis "viral infection" based on whether a first n-gram of a first set of n-grams and a second n-gram of a second set of n-grams are selected during a medical checkup using an electronic medical record (EMR) system.

Alternatively, or in addition, some embodiments may use an updated decision tree to change one or more system operations or mechanical operations. For example, some embodiments may obtain input values from a client communication program as inputs for a decision system that uses the updated decision tree. Some embodiments may then categorize, label, or otherwise indicate one or more values based on the decision nodes of the decision tree. For example, a decision may have been updated to indicate that the domain "stop request" includes the sequence of n-gram "cancel services," where an indication of a stop request may cause an NLP system to stop a program using natural language processing program code (e.g., a chatbot). Some embodiments may then receive a web message indicating that an NLP system has received a client communication that includes the phrase "cancel services" and, in response, stop the execution of an NLP program code being used to communicate from the client.

In some embodiments, a user may be notified based on the update to the set of decision trees. In some embodiments, a decision tree may be associated with a list of user accounts or a list of categories associated with user accounts. The list of user accounts or categories associated with user accounts may be used to notify users in response to a determination that the categories associated with user accounts may be updated. For example, some embodiments may determine that a list of categories associated with an updated decision tree includes the user roles "administrator" and "doctor." Some embodiments may then select a set of user accounts associated with the user roles and, for each respective user account, send a respective notification message via a messaging communication platform, an e-mail, a SMS text message, or the like. For example, after determining that an update to an ontology graph via a first user's interaction with a UI displaying rendered text from a document causes an update to a decision tree, some embodiments may send a notification message to a second user indicating that the decision tree has been updated.

In some embodiments, the process 1900 may include updating the UI based on the updates to the set of ontology graphs, as indicated by block 1942. Operations to update the UI may include one or more operations described above for block 1914. As described above, some embodiments may send the message to update the UI to indicate that the change to the n-gram described above has been performed. For example, some embodiments may obtain a request to update an n-gram that is associated with a first ontology graph to instead be associated with a second ontology graph. After performing one or more operations described above, some embodiments may then send a message to the client computing device that causes the UI to update its display of rendered text to include a visual indicator that indicates that the n-gram is mapped to the second ontology graph.

Figure 20:
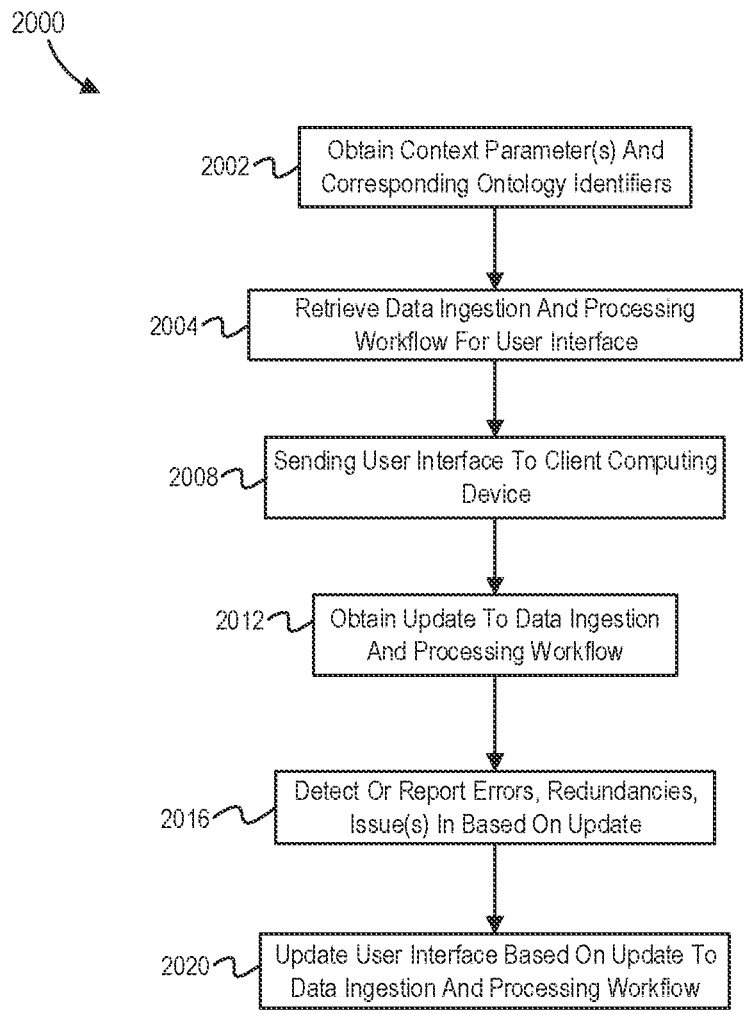
FIG. 20 is a flowchart of operations to for updating a user interface for updating a workflow, in accordance with some embodiments of the present techniques.

FIG. 20 is a flowchart of operations to for updating a user interface for updating a workflow, in accordance with some embodiments of the present techniques. Operations of the process 2000 may start at block 2002. In some embodiments, the process 2000 may include obtaining a set of context parameters and a corresponding set of ontology identifiers, as indicated by block 2002. Operations to obtain the set of context parameters or corresponding ontology identifiers may be similar to operations described elsewhere in this disclosure. For example, the set of context parameters may be obtained from a user account, determined from data obtained from a client computing device being used to access the user account, or determined from queries or other inputs provided by the user.

In some embodiments, the process 2000 may include retrieving a data ingestion or processing workflow, as indicated by block 2004. Retrieving the data ingestion or processing workflow may include obtaining a workflow that is automatically loaded for a user to update. Alternatively, or in addition, some embodiments may retrieve the data ingestion or processing workflow after receiving a message to retrieve the workflow based on an identifier provided in the message.

Retrieving the data ingestion or processing workflow may include retrieving data encoded in one or more various data serialization formats, such as a JSON, XML, YAML, or the like. For example, some embodiments may retrieve a set of data including a structured data document that is written using a data serialization format represented in the form a bracketed data such as, '{"name": "pipe1", "pipes": [{"name": "pipe0", "sources": ["https://1f9i3tng.xml" ], "steps": [{"type": "transformer", "value": "xml_src_cr_doc", "args":[ ] . . . ' As by the bracketed data, different values enclosed in different brackets may include different elements of a workflow, such as a name of a neural network model used process data or a name of a data ingestion source used to add documents to corpora. Some embodiments may then dynamically generate a user interface based on the workflow data, where a sub-element (e.g., a list within a list) in the bracketed data may be converted into smaller shapes that are then fit into larger shapes representing an element that includes the sub-element. As described further below, some embodiments may then dynamically update a UI with workflow blocks or other UI elements to represent a set of workflow operations to ingest and process data. Some embodiments may then generate an updated version of the structured data document.

Alternatively, or in addition, some embodiments may obtain a specific representation of a UI configuration corresponding to the workflow. For example, some embodiments may retrieve a set of values indicating the position of UI elements representing one or more operations of a data ingestion or processing workflow, where the set of values may be represented by '[[0, "start", {"collapsed":true, "xcor":0, "ycor": 0, "heading":0,}], 100, 100, [null, 53, null]], . . . ' As described further below, some elements of the UI display data may be linked to elements of the workflow data via an identifier shared between the two elements.

In some embodiments, the process 2000 may include sending the UI to the client computing device, as indicated by block 2008. Operations to send the workflow may include one or more operations similar to operations to send or update a UI as described elsewhere in this disclosure. For example, some embodiments may send a web message including program code to a client computing device. Furthermore, as described elsewhere in this disclosure, the UI may include one or more UI elements that permit a user to update data sources, model selection, model parameters, or other elements of a data ingestion and processing workflow.

in some embodiments, the process 2000 may include obtaining an update to the data ingestion and processing workflow, as indicated by block 2012. Operations to obtaining an update to the workflow may include operations similar to those described for operations to obtain web messages or other messages as described elsewhere in this disclosure. Some embodiments may obtain the update to the data ingestion via a message provided by a client computing device. The message may include data indicating updates to the data ingestion and processing workflow, where the data may include elements of program data similar to the program data for the data ingestion or processing workflow described above. Some embodiments may receive indicators of differences between the retrieved workflow code and the updated workflow code, where the message does not include the entirety of the workflow code.

In some embodiments, the process 2000 may include detecting or reporting errors, redundancies, or other detected issues based on the update to the data ingestion and processing workflow, as indicated by block 2016. Various operations may be performed to determine whether a workflow includes one of a set of detected issues. Some operations may include determining whether the workflow satisfy a set of criteria, where different criterion of the set of criteria may correspond with different issues. For example, some embodiments may determine whether the workflow satisfies a first criterion to determine whether two different text processing models are being used, where the two different text processing models are indicated to be counter-productive or redundant with respect to each other. Some embodiments may then determine whether the workflow satisfies a second criterion to determine whether a set of listed document ingestion pipelines duplicate data ingestion. Some embodiments may provide a notification to indicate whether one or more of the issue criteria is satisfied and, in response notify a user that the update to the workflow may create one or more detected issues. Some embodiments may further perform operations to determine whether the data ingestion pipeline updates an ontology graph that a user may not have permission to update.

In some embodiments, the process 2000 may include updating the UI based on the update to the data ingestion and processing workflow, as indicated by block 2020. Operations to update UI may include operations described elsewhere in this disclosure. For example, some embodiments may send a web message including an encoded form of the workflow. Alternatively, or in addition, some embodiments may send an updated version of a UI configuration that may re-configure the appearance of the workflow representation in the UI.

As disclosed elsewhere in this disclosure, some embodiments may generate a set of compiled program instructions to perform one or more operations described in this disclosure. Various compilers may be used to generate the compiled program instructions, such as Glow, TVM, MLIR, or the like. Some embodiments may use a compiler stack adapted for learning operations, such as the TVM compiler described by Chen et al. (Chen, T., Moreau, T., Jiang, Z., Zheng, L., Yan, E., Shen, H., Cowan, M., Wang, L., Hu, Y., Ceze, L. and Guestrin, C., 2018. {TVM}: An automated end-to-end optimizing compiler for deep learning. In 13th {USENIX}Symposium on Operating Systems Design and Implementation ({OSDI} 18) (pp. 578-594)), which incorporated herein by reference. For example, some embodiments may use a deep learning-adapted compiler to combine small operations, static memory planning pass, and data layout transformations. Some embodiments may combine small operations by fusing operators to a single kernel, such as fusing injective operators (i.e. one-to-one mapping operators) with reduction operators (e.g., summation operators). For example, some embodiments may compile program instructions using an operator fusion operation that includes selecting an addition operator and a summation operator and fusing the two operators into a single operator, where the fused operator does not store intermediate results of both the addition operator and summation operator.

In addition, some embodiments may perform other operations such as reinterpret tensor operations optimized for specific hardware configurations, cooperative data fetching, tensorizing arithmetic workflows, or the like. Some embodiments may select the use of a learning-adapted compiler based on a determination that a workflow includes one or more learning operations. For example, in response to a determination that an instruction to update the UI includes an instruction to use a neural network, some embodiments may select a learning-adapted compiler to perform one or more operations.

Figure 21:
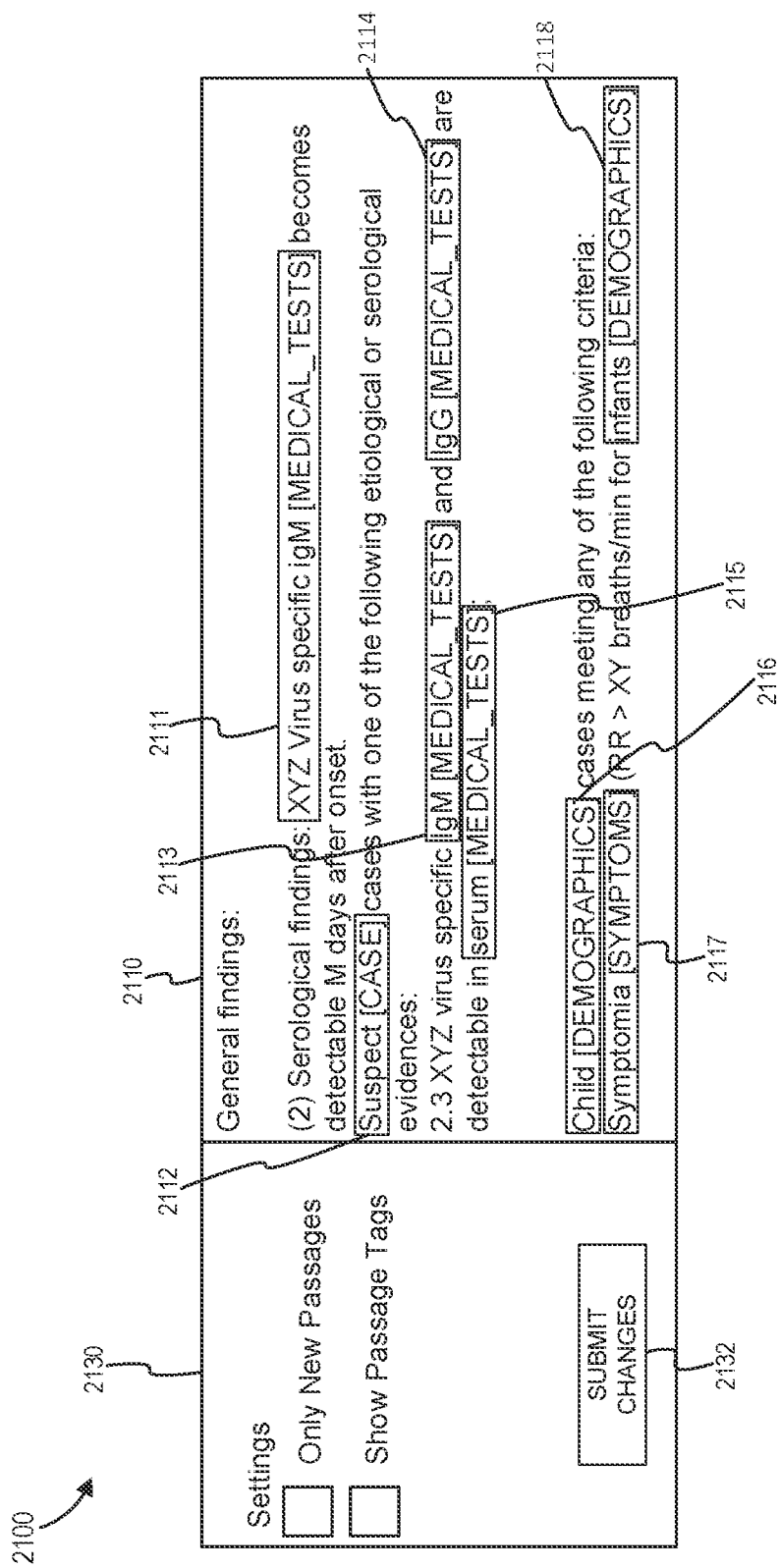
FIG. 21 is a diagram of an example set of user interface elements indicating ontology-linked n-grams, in accordance with some embodiments of the present techniques.

FIG. 21 is a diagram of an example set of user interface elements indicating ontology-linked n-grams, in accordance with some embodiments of the present techniques. As used in this disclosure, an ontology-linked n-gram may include an n-gram that maps to a vertex of an ontology graph, where the mapping may be a direct mapping or be based on a learned representation of the n-gram. The set of UI elements 2100 includes a UI element 2110 and a second UI element 2130, where the UI element 2110 is shown as a first window that includes text from a retrieved natural-language text document. A UI element may include any element of a UI that may be viewed or interacted with by a user. Examples of UI elements may include buttons, sliders, radio dials, modal windows, other windows, sidebars, or the like, where a UI element may include other UI elements. As used in this disclosure, an interaction with a first UI element may include an interaction with a second UI element if the second UI element is within or otherwise connected to the first UI element. For example, the UI element 2110 includes the UI element 2132, and an interaction with the UI element 2132 may also be an interaction with the UI element 2110.

The set of visual indicators 2111-2118 may indicate different words or other ontology-linked n-grams that are mapped to a set of vertices of a set of ontology graphs. Different respective visual indicators of the set of visual indicators 2111-2118 may correspond with different ontology graphs. For example, the first visual indicator 2111, third visual indicator 2113, fourth visual indicator 2114, and fifth visual indicator 2115 may be colored with a first color to indicate that they are associated with a first ontology graph. In addition to the coloration of the visual indicator, the visual indicator may include an identifier of the associated ontology graph, which is displayed as "MEDICAL_TESTS." In addition, the second visual indicator 2112 may be associated with a second ontology graph labeled with the domain category "CASE" and may include the text "CASE" to further indicate the domain category. In addition, the sixth visual indicator 2116 and the eighth visual indicator 2118 may be associated with a third ontology graph labeled with the domain category "DEMOGRAPHICS" and may include the text "CASE" to further indicate the domain category. In addition, the seventh visual indicator 2117 may be associated with a fourth ontology graph labeled with the domain category "SYMPTOMS" and may include the text "SYMPTOMS" to further indicate the domain category.

Some embodiments may provide a UI that permits a user to update one or more ontology graphs with a UI element. For example, some embodiments may provide a UI that permits a user to highlight the word "Serological" being displayed in the UI element 2110 and indicate that the word should be added to the second ontology graph via interactions with a set of UI elements. After updating the UI to indicate that the word "Serological" should be added to an ontology, a user may interact with the UI element 2132 by clicking on or tapping on the UI element 2132 to send a message that indicates an update to an ontology graph.

Figure 22:
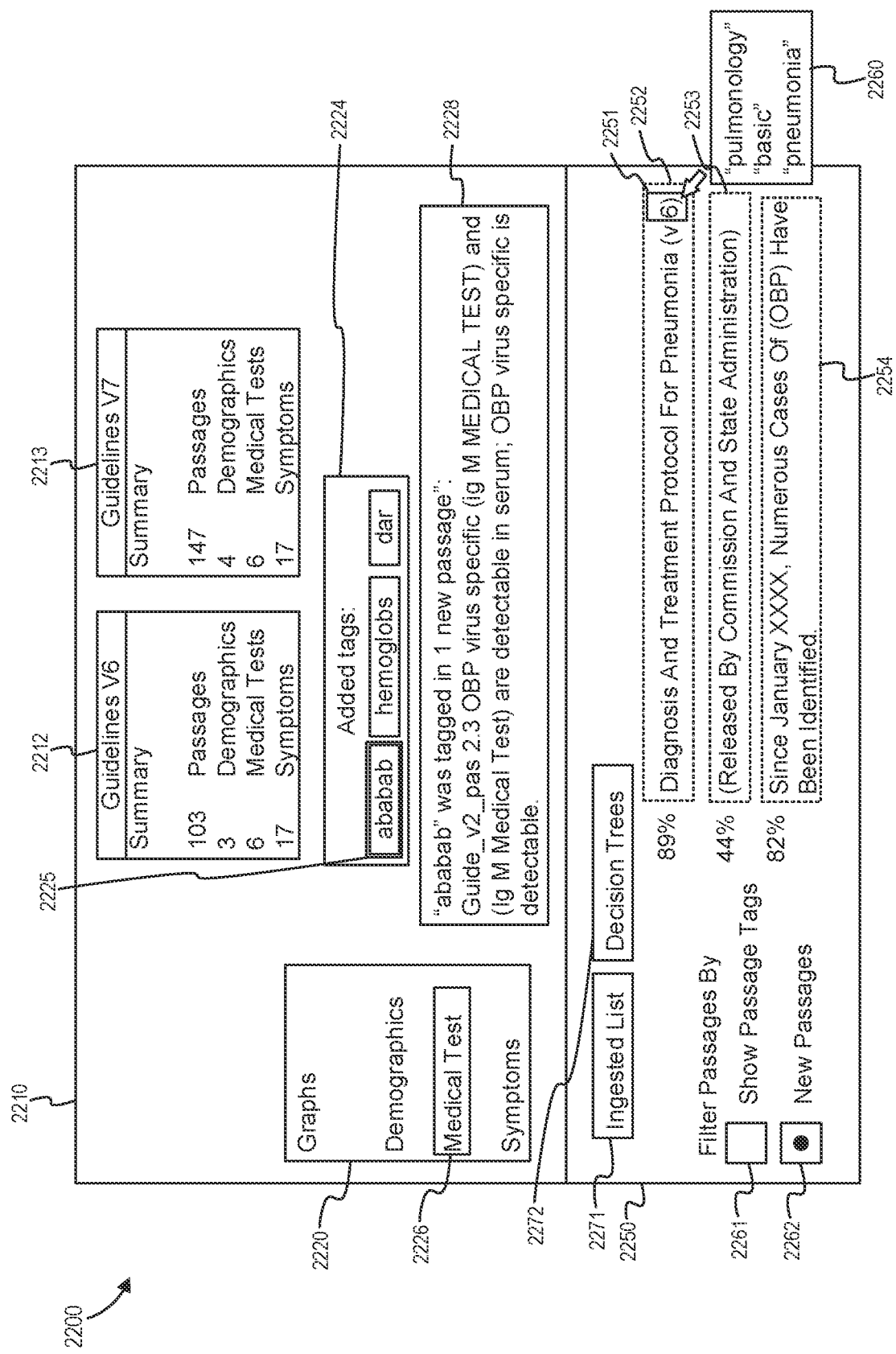
FIG. 22 is a diagram of an example set of user interface elements indicating comparisons between different versions of a document, in accordance with some embodiments of the present techniques.

FIG. 22 is a diagram of an example set of user interface elements indicating comparisons between different versions of a document, in accordance with some embodiments of the present techniques. The set of UI elements 2200 includes a change summary window 2210 and a text comparison window 2250. The change summary window 2210 includes a first summary window 2212 and a second summary window 2213. Each respective summary window of the first and second summary windows 2212-2213 summarizes both a total number of text sections and a count of text sections corresponding to ontology graph categories.

The change summary window 2210 also includes a selection menu 2220, which provides a list of domain identifiers corresponding with different ontology graphs. Each domain identifier in the list of domain identifiers may be presented as an interactive UI element. For example, after selecting the UI element 2226, which includes the identifier "Medical Test," a window 2228 may present text from a first document associated with the domain identified by the identifier "Medical Test." While not shown in FIG. 22, some embodiments may provide a UI that includes other types of domain category values, such as expertise class values, concepts or other subdomains, or the like. The change summary window 2210 also includes a tag selection window 2224 presents three UI elements such as the UI element 2225, where each UI element shows an identifier of a domain category associated with one or more updated text sections when comparing the first document with a second document. The three UI elements shown in the tag selection window 2224 may correspond with expertise class values, concepts, or other subdomains of the domain selected with the selection menu 2220 and may be used to further filter the display text in the window 2228. For example, after a user taps on the UI element 2225 using a touchscreen or otherwise interacts with the UI element 2225, the window 2228 may present text associated with the domain category "ababab." As described elsewhere in this disclosure, some embodiments may determine that the text section in the window 2228 is associated with the domain category "ababab" based on an association between the acronym "OBP" and the category, "ababab."

As used in this disclosure, a first and second document may be versions of a shared document. For example, a first document may be an updated version of a second document, where the second document may be stored as the first document in combination with a set of changes to the first document. As described above, some embodiments may provide a UI capable of filtering the text of a document to present only portions of the text surrounding a text section where a pair of documents differ when comparing the pair of documents.

In some embodiments, the two versions of the document may be two versions of a set of natural language instructions. As described elsewhere in this disclosure, some embodiments may display the domain category values most relevant to a user when prioritizing detected changes between an updated version and a prior version of a set of natural language instructions. A set of natural language instructions may include a flow chart, a manual for operating a device or using a program, a regulation or other government rule, a company policy or policy of an organization, or a decision tree. Some embodiments may display a set of topics or other domain category values in association with the corresponding changes between two versions of natural language instructions.

While the above describes showing comparisons between two versions of a same document to track changes of the document, some embodiments may track changes in n-grams over time based on the use of the n-gram in multiple documents over time. As described elsewhere in this disclosure, some embodiments may update associations between different concepts or other n-grams over time based on documents authored or otherwise obtained at different times. For example, based on a first set of documents authored before a first date, some embodiments may determine that the n-gram "vert1" is associated with the n-grams "vert2," "vert3," and "vert4," where each of the n-grams may represent concepts in a document. After obtaining a second set of documents authored after the first date, some embodiments may determine that the n-gram "vert1" is associated with an n-gram "vert5" based on an updated embedding vector corresponding with the n-gram "vert5," where the n-gram "vert5" may represent another concept and may be encoded in a same or different ontology graph with respect to the n-gram "vert1." Some embodiments may then update the set of ontology graphs, such as by appending a subarray associating the pair of vertices to an array of subarrays, where each subarray may represent a graph edge of an ontology graph. Some embodiments may then update additional operations based on a discovered association between a first concept and a second concept, such as by updating text-displaying operations to display the second concept after a user highlights the first concept. In addition, some embodiments may store a time corresponding to when the association between the first and second concept was first detected. Some embodiments may then provide a visualized representation of a time-based map of the change in associations between different concepts or other n-grams.

Some embodiments may label a paragraph, specific text section, or other text section with a category in response to a determination that the text section includes one or more ontology-linked n-grams associated with the label. For example, some embodiments may determine that the n-gram "OBP" maps to a first vertex of an ontology graph and that the first vertex is associated with a second vertex mapped to the n-gram "ababab." In some embodiments, the n-gram "ababab" may represent a concept associated with multiple vertices other vertices such as a vertex mapping to the n-gram "OBP." Alternatively, or in addition, some embodiments may determine that the n-gram "OBP" is associated with a category labeled "ababab" via an index of categories associated with n-grams.

The text comparison window 2250 displays a set of text sections from a first document and a visual indicator 2251 indicating a text difference between a text section of the first document in contrast with a second document. In addition, some embodiments may indicate one or more domains affected by the difference. For example, each respective text section of the text sections 2252-2254 may be presented with a set of respective domain category values associated with the respective passage in a screen location adjacent or otherwise in proximity to (e.g., within 100 points of a screen). For example, a user may move a cursor 2230 over the text section 2252 to open a window 2260, where the window 2260 may indicate a set of domain category values including a domain "pulmonology," a domain class "basic," and a subdomain "pneumonia."

The set of UI elements 2200 also includes other buttons or other UI elements that may update the data being displayed in the text comparison window 2250, such as the first button 2261, second button 2262, third button 2271, and fourth button 2272. For example, an interaction with the first button 2261 may cause the presentation of a set of domain category values associated with each respective text section of the text sections 2252-2254. For example, a UI may be updated after a user clicks on the first button 2261, where the update may cause the domain category values "pulmonology," "basic," and "pneumonia" to be displayed in proximity with the text section 2252. In some embodiments, an interaction with the second button 2262 may display only text sections that have been determined to have been updated. In some embodiments, an interaction with the third button 2271 may display a list of natural-language text documents from a corpus of text data that includes text sections 2252-2254. In some embodiments, an interaction with the button fourth 2272 may display one or more decision trees that are associated with the document being displayed. For example, after an interaction with the fourth button 2272, the text comparison window 2250 may display a decision tree having decision tree nodes associated with one or more n-grams used in the text sections 2252-2254 or other text sections of a document.

Figure 23:
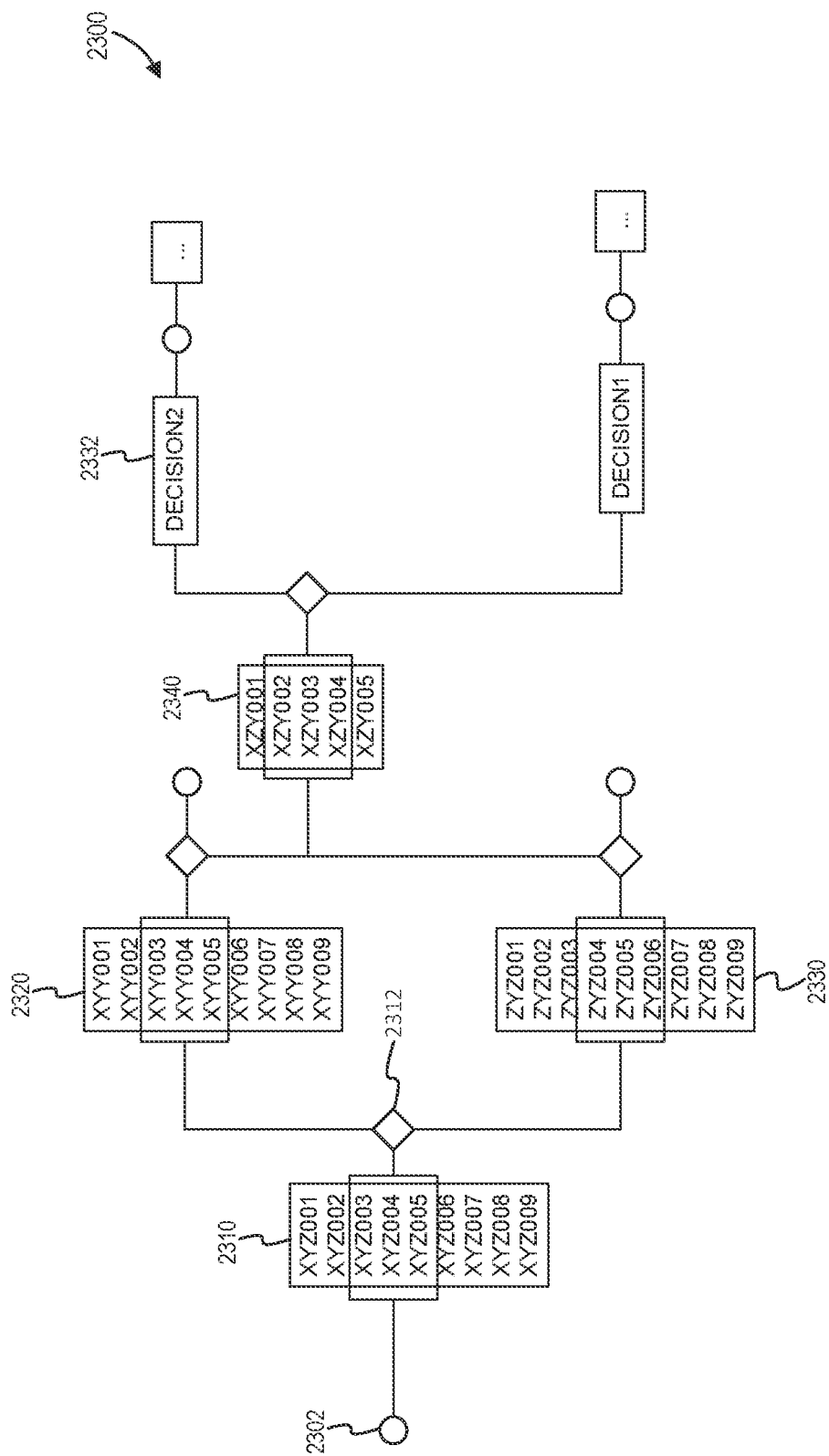
FIG. 23 is a diagram of an example user interface displaying a representation of a decision tree, in accordance with some embodiments of the present techniques.

FIG. 23 is a diagram of an example user interface displaying a representation of a decision tree, in accordance with some embodiments of the present techniques. Some embodiments may provide a UI that displays a decision tree, where the decision tree may be used to perform operations such as recommending an action, labeling a record, or the like. The decision tree 2300 includes a decision tree root node 2302 and a rules engine implementing the decision tree 2300 may begin at a state represented by the decision tree root node 2302.

The UI displaying the decision tree 2300 may permit a user to view or update a first list of n-grams 2310. In some embodiments, the first list of n-grams 2310 may be associated with one or more vertices of an ontology, where each of the one or more vertices may be associated with a shared label. For example, the first list of n-grams 2310 may each recite a first set of symptoms, where each symptom may be mapped to a vertex of an ontology graph that is associated with a first shared label. In some embodiments, the vertices may share a label by being associated with another vertex representing a concept via a set of graph edges. For example, the vertices of a first set of n-grams may share the label "type 1 symptom" based on each of the vertices be associated with a graph edge to another vertex that map to the n-gram "type 1 symptom." Alternatively, or in addition, some embodiments may store an index or data table of labels, where a record of the data table may provide a list of n-grams or their corresponding vertices of an ontology graph.

An implementation of the decision tree may then provide the first list of n-grams 2310 to a set of program instructions to provide or more decisions based on the decision tree 2300 based on whether an n-gram of the first list of n-grams is provided as an input to the set of program instructions. For example, a function of the set of program instructions may include presenting a second user with a list of options that include options corresponding with the first list of n-grams 2310. In response to a determination that the second user did provide an n-gram of the first list of n-grams as an input to the set of program instructions, some embodiments may use the decision tree 2300 to categorize a record or perform an action based on the provided n-gram.

Some embodiments implementing the decision tree 2300 may then proceed to a decision point represented by the decision tree node 2312. The logic corresponding with the decision tree node 2312 may include determining whether the second user should be permitted to select n-grams that include the second list of n-grams 2320 or n-grams that include the third list of n-grams 2330. For example, an application executing on a client computing device may obtain a dataset representing the decision tree 2300 via an API and use a rules engine to implement the decision tree 2300. The application may present a first UI window that provides a user with a superset of symptoms that includes the symptoms corresponding with the list of n-grams 2310. If a user of the application selects symptoms corresponding with a first subset of n-grams of the list of n-grams 2310, the application may provide the user with a second UI window that permits the user to select follow-up symptoms corresponding with the second list of n-grams 2320. If a user of the application selects symptoms corresponding with a second subset of n-grams of the list of n-grams 2310, the application may provide the user with a third UI window that permits the user to select follow-up symptoms corresponding with the third list of n-grams 2330. For example, after a user selects a first option corresponding with the n-gram "XYZ003," the logic represented by the decision tree node 2312 may cause the application to provide a UI displaying symptoms corresponding with the second list of n-grams 2320.

Some embodiments may perform categorization decisions based on the decision tree 2300. For example, some embodiments may perform a categorization operation represented by the decision tree node 2332, where a user's selection of n-grams from one or more of the list of n-grams 2310, 2320, 2330 or 2340 may be used to perform a labeling decision. As discussed elsewhere in this disclosure, a categorization decision may be based on n-grams selected or detected from a plurality of sets of n-grams. For example, a decision system that uses the decision tree 2300 may recommend that a patient record be labeled with "gout" in response to a determination that the n-gram "pain" is detected from the list of n-grams 2310 and that the n-gram "swelling" is detected from the list n-grams 2320.

As disclosed above, some embodiments may permit a user to update a set of n-grams associated with ontology graphs. For example, some embodiments may detect that a user updated an ontology graph by adding a new n-gram to the first list of n-grams 2310 and, in response, update the logic corresponding with the decision tree node 2312 to proceed to logic corresponding with the decision tree node 2312 if the new n-gram was selected. Alternatively, or in addition, some embodiments may update logic corresponding with the categorization operation represented by the decision tree node 2332. For example, some embodiments may determine that a new n-gram is associated with a diagnosis n-gram representing a category based on a relationship type update provided by a user in a UI and add the new n-gram to the fourth list of n-grams 2340. Some embodiments may then update the logic corresponding with the decision tree node 2332 to cause an application implementing the decision tree 2300 to categorize a record with the diagnosis n-gram based on a detection of the new n-gram.

As described elsewhere, some embodiments may use a compiler system, such as the LLVM compiler system to first generate an intermediate representation of the implementation of the decision tree. Some embodiments may then provide the intermediate representation to a client computing device for use by the client computing device. By providing the client computing device with a pre-compiled version of the decision tree after an ontology update, some embodiments may reduce the bandwidth required to execute an application implementing the rules engine. In addition, some embodiments may reduce the computational resources required to implement the decision tree by generating an intermediate representation of the decision tree in response an update to a set of ontology graphs.

Figure 24:
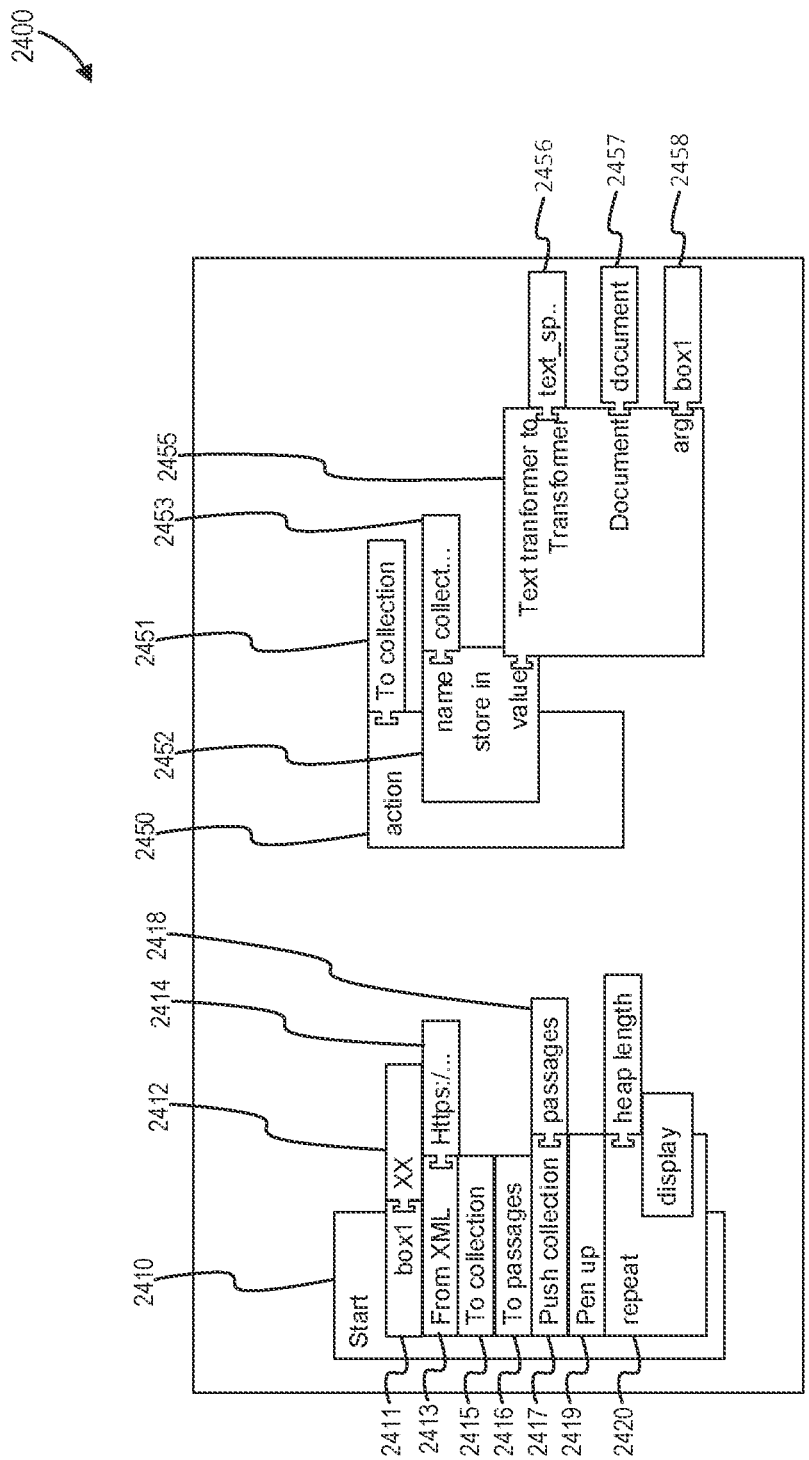
FIG. 24 is a diagram of an example set of user interface elements permitting the updating of a set of corpus and data processing elements, in accordance with some embodiments of the present techniques.

FIG. 24 is a diagram of an example set of user interface elements permitting the updating of a set of corpus and data processing elements, in accordance with some embodiments of the present techniques. As discussed elsewhere in this disclosure, some embodiments may obtain an update to an ontology graph based on an interaction with a UI that includes a set of UI elements 2400. The set of UI elements 2400 may include interactive elements that allow a user to form connection lines or other connecting shapes between visualizations that represent ontology graphs, machine learning models, or the like.

The set of UI elements 2400 includes a workflow block 2410 that is shown to include UI elements as a set of workflow blocks 2411-2420. The workflow blocks may be displayed in various forms, such as rectangles, circles, ellipsoids, or other shapes. In some embodiments, the workflow blocks may be shown to be in contact with each other. For example, the workflow block 2411 is shown to be in contact with the workflow block 2410. In some embodiments, an order of a workflow may be visually represented by a direction of the workflow blocks. Some embodiments may display a next workflow operation of a current workflow operation based on a visual association between the workflow operations. Some embodiments may visually represent an order of a set of workflow operations by the direction in which the corresponding workflow blocks representing the operations appear. For example, by displaying the workflow blocks 2411, 2413, 2415-2417, and 2419-2420 proceeding from top to bottom, some embodiments may indicate that each workflow operation of the set of workflow operations represented by the workflow blocks 2411, 2413, 2415-2417, and 2419-2420 are performed in sequence, starting at the workflow block 2411 and ending at the workflow block 2420. It should be understood that this relationship between spatial configuration and an order of the set of workflow operations may be changed in other embodiments.

Some embodiments may provide a UI that to indicates specific inputs, parameters for a workflow, data sources, names, or other values associated with a workflow operation. The set of UI elements 2400 includes multiple workflow blocks that represent specific inputs or models to be used during an execution of a workflow. The workflow block 2412 may indicate that the workflow block 2411 has an input value "XX," which may indicate that the workflow operation represented by the workflow block 2411 may have the name "XX." In addition, the workflow block 2413 may represent a data ingestion operation, where the data may be provide by a hyperlink or other data source address represented by the block 2414.

Some embodiments may permit workflow blocks to indicate relationships between workflow operations. For example, a workflow block 2450 is indicated to have the title "To collection" by the workflow block 2451. Sub-elements of the workflow block 2450 include the workflow blocks 2456-2458, which may represent a neural network model, input set of documents, and additional argument(s), respectively. As indicated by shared name "box1" depicted in the workflow block 2458, some embodiments may provide a workflow operation or result(s) of a workflow operation as an argument for another workflow operation. Similarly, the workflow block 2415 has the title "To collection" to indicate that the workflow block 2415 represents an execution of an operation that is further defined in the workflow block 2450. The inclusion of the workflow block 2415 in the workflow block 2410 may indicate that the set of operations represented by the workflow block 2410 includes performing operations represented by the workflow block 2450. For example, the operations represented by the workflow block 2410 may include data processing operations, such as operations to perform a transformer-based learning operation using the machine learning model represented by block 2456 based on inputs of the type "document" represented by the workflow block 2457.

Furthermore, As discussed elsewhere in this disclosure, some embodiments may determine whether one or more alert criteria will be violated. In some embodiments, after determining that an interaction with a UI would update a hierarchical set of graphs, some embodiments may verify whether one or more of the set of rules or other conditions would be violated. Various conditions may be applied and tested, such as a condition that restrict vertices of a first type from being associated with vertices of a second type, a condition that restricts n-grams associated with a first concept from being associated with a second concept, a condition that restricts vertices associated with a first class value from being associated with vertices having a different class value without an appropriate user authorization, or the like. For example, some embodiments may include a condition that a user logged in via a user account must have an appropriate permission value before being permitted to edit a connection between a first vertex representing a first concept and a second vertex representing a second concept. In response to a determination that a rule would be violated by a proposed connection between vertices, a verification element of the UI may change text or appearance (e.g., change a color, shape, size, or the like) to indicate that the rule would be violated by the proposed connection other proposed update to a set of ontology graphs.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g., within a data center or geographically), or otherwise differently organized. The functionality described herein may be provided by one or more processors of one or more computer devices executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively. Computer implemented instructions, commands, and the like are not limited to executable code and can be implemented in the form of data that causes functionality to be invoked, e.g., in the form of arguments of a function or API call.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

The present techniques will be better understood with reference to the following enumerated embodiments:

1. A computer-implemented method of active learning domain-specific ontologies based on unsupervised learning of the ontologies from corpora of natural-language text documents and expert guidance to update the ontologies, the method comprising: obtaining, with a computer system, a set of ontologies, wherein ontologies in the set of ontologies map n-grams onto concepts to which the n-grams refer in different respective domains of knowledge; receiving, with the computer system, an update associating a first n-gram with a first concept; receiving, with the computer system, information by which the update is associated with a given domain of knowledge of a user providing the update; selecting, with the computer system, a subset of ontologies from among the set of ontologies by determining that the update in the given domain of knowledge is applicable to respective domains of knowledge of the subset of ontologies; determining, with the computer system, that the first concept has a specified type of relationship to a subset of concepts to which other n-grams are mapped in the subset of ontologies; and storing, in memory of the computer system, in response to the determination, associations between the first n-gram and the subset of concepts in at least some of the subset of ontologies.

2. The method of embodiment 1, comprising: obtaining a corpus of natural-language text documents; and performing unsupervised learning of at least some of the mapping of n-grams onto concepts by using the natural-language text documents to train a language model that represents the n-grams as vectors in an embedding space in which pairwise distances between vectors is indicative of semantic similarity of pairs of n-grams represented by respective pairs of vectors.

3. The method of embodiment 2, comprising training a plurality of language models corresponding to different domains of knowledge, wherein different ontologies in the set of ontologies are learned based on different language models among the plurality of language models.

4. The method of any of embodiments 1 to 3, comprising using at least some of the subset of ontologies to, based on a given domain of knowledge, expand a query, extract an acronym, extract a keyword, extract a relationship, disambiguate a term, recognize a named entity, update a knowledge graph, or extract a relationship between entities.

5. The method of any of embodiments 1 to 4, wherein: the set of ontologies comprises a first ontology, a second ontology, and a third ontology; a first ontology is associated with a first class value corresponding to the first domain; the second ontology is associated with a second class value corresponding to the second domain; the third ontology is associated with a third class value corresponding to the third domain; selecting the subset of ontologies further comprises: determining whether a set of account parameters associated with the user satisfies a first domain threshold, wherein the first domain threshold is based on the first class value; in response to a determination that the set of account parameters satisfies the first domain threshold: selecting the first ontology; determining a first domain category distance based on a first difference between the second class value and at least one parameter of the set of account parameters; determining a second domain category distance based on a second difference between the third class value and at least one parameter of the set of account parameters; determining whether the first domain category distance satisfies a first distance threshold associated with the second ontology; determining whether the second domain category distance does not satisfy a second distance threshold associated with the second ontology; selecting the second ontology in response to a determination that the first domain category distance satisfies the first distance threshold; and not selecting the third ontology in response to a determination that the second domain category distance does not satisfy the second distance threshold.

6. The method of any of embodiments 1 to 5, wherein determining the association between the first n-gram and the subset of concepts comprises: selecting a first vertex corresponding to the first n-gram by searching the first set of n-grams, wherein the association between the first vertex and the first concept is categorized with first relationship category of a set of relationship categories; determining whether an association between the first concept and the subset of concepts is categorized with a second relationship category of the set of relationship categories; and in response to a determination that the association between the first concept selecting the first concept based on the first concept corresponding to a first vector that maps to the first n-gram; selecting a second concept based on the second concept corresponding to a second vector that maps to the second n-gram, wherein the subset of concepts comprises the second concept, wherein storing associations between the first n-gram and the subset of concepts comprises storing an ontological triple associating the first n-gram with the second concept.
7. The method of any of embodiments 1 to 6, wherein: storing the association between the first n-gram and the subset of concepts comprises updating a B-tree index; a key value of a first node of the B-tree corresponds to one of a pair of elements, wherein the first element of the pair of elements identifies the first n-gram, and wherein a second element of the pair of elements identifies a concept of the subset of concepts; and a pointer value of a second node of the B-tree corresponds to the other of the pair of elements.
8. The method of any of embodiments 1 to 7, further comprising: obtaining a first query during a login session, wherein a user account of the user is used to provide the first query during the login session, and wherein the first query comprises the first n-gram; determining a second n-gram associated with a second concept, wherein the subset of concepts comprises the second concept; generating an expanded query based on the first query, wherein the expanded query comprises the second n-gram and not the first n-gram; obtaining a first document associated with the expanded query.
9. The method of embodiment 8, further comprising: obtaining a corpus of natural-language text documents; obtaining an first set of training queries and a first set of training documents associated with the first set of training queries, wherein the corpus comprises the first set of training documents; obtaining a first set of neural network parameters by training a first neural network based on the first set of training queries and the first set of training documents; obtaining a second set of training queries and a second set of training documents associated with the second set of training documents, wherein the corpus comprises the first set of training documents; and obtaining a second set of neural network parameters by training a second neural network based on the second set of training queries and the second set of training documents, wherein the second neural network is initialized with the first set of neural network parameters; and wherein obtaining the first document comprises using the second set of neural network parameters.
10. The method of any of embodiments 1 to 9, wherein the update is a first update, the method further comprising presenting a user interface (UI) to a user, the UI comprising a set of UI elements, wherein: an interaction with the set of UI elements causes a formation of a connection line between a first visualization representing the first concept with a second visualization representing the second concept; and receiving a second update indicating an association the first concept and the second concept based on an interaction with the set of UI elements.
11. The method of embodiment 10, wherein the set of UI elements comprises a verification element that visually indicates whether a proposed connection between the first concept and the second concept satisfies a set of rules associated with the user.
12. A method comprising: obtaining, with a computer system, a set of graphs comprising: a first ontology graph associated with a first domain category value, the first ontology graph comprising a first vertex and a second vertex; and a second ontology graph associated with a second domain category value, the second ontology graph comprising a third vertex, wherein the second vertex is connected to the third vertex via a first graph edge; obtaining, with the computer system, an update associating a first n-gram with the second vertex, wherein the first vertex is mapped to the first n-gram, and wherein the first domain category value is associated with the update; determining a first relationship type between the first vertex and the second vertex based on the update; selecting, with the computer system, the second ontology graph from amongst a plurality of ontology graphs based on the first domain category value and a second domain category value associated with the second ontology graph; determining, with the computer system, whether the first graph edge is associated with a second relationship type that satisfies a relationship criterion based on the first relationship type; determining, with the computer system, an association between the first n-gram indicated by the first vertex and a second n-gram associated with the third vertex; and updating, with the computer system, the set of graphs, the updating comprising storing the association between the first n-gram and the second n-gram in memory.
13. The method of embodiment 12, wherein obtaining the update comprises: obtaining a document comprising the first n-gram and a third n-gram, wherein the third n-gram is indicated by the second vertex; determining an ontological triple based on a sequence of document-obtained n-grams comprising the first n-gram and the third n-gram, wherein the ontological triple comprises a first identifier identifying the first vertex, a second identifier identifying the second vertex, and a category of the association between the first vertex and the second vertex, wherein the category is based on a fourth n-gram of the sequence of document-obtained n-grams; and determining the association between the first vertex and the second vertex based on the ontological triple.
14. The method of any of embodiments 12 to 13, the operations further comprising: obtaining a user-provided query during a login session, wherein a user account is associated with the login session, and wherein the user account comprises an account parameter indicating a class value; determining a set of n-grams based on the user-provided query, the set of n-grams comprising the first n-gram; retrieving the second n-gram based on the association between the first n-gram and the second n-gram stored in memory; generating an expanded query based on the second n-gram; retrieving a first document of a corpus of natural-language text documents based on the user-provided query; determining a first relevance score associated with the first document based on the n-grams of the user-provided query and the account parameter; retrieving a second document of the corpus of natural-language text documents based on the expanded query; determining a second relevance score associated with the second document based on the n-grams of the expanded query and the account parameter; and presenting the first document and the second document, wherein a comparison between the first relevance score and the second relevance score causes the second document to be presented before the first document is presented or causes the second document to be presented on top the first document in a user interface.

15. The method of embodiment 14, wherein generating the expanded query comprises: determining a set of embedding vectors based on a selected set of n-grams of the user-provided query using an encoder neural network, the encoder neural network comprising less than four neural network layers; a set of positional encoding vectors, wherein each respective positional encoding vector of the set of positional encoding vectors is determined based on a position of a respective n-gram in the selected set of n-grams; generating a first random feature map based on the set of embedding vectors using a random feature map function, wherein using the random feature map function based on the set of embedding vectors comprises generating a first set of random or pseudorandom variables and multiplying at least one variable of the first set of random or pseudorandom variables with the at least one element of the set of embedding vectors; generating a second random feature map based on the set of positional encoding vectors using the random feature map function, wherein using the random feature map function based on the set of positional encoding vectors comprises generating a second set of random or pseudorandom variables and multiplying at least one variable of the second set of random or pseudorandom variables with the at least one element of the set of positional encoding vectors; and determining a set of attention values based on the first random feature map and the second random feature map; and generating the expanded query of using a neural network based on the set of attention values.

16. The method of any of embodiments 14 to 15, wherein the expanded query is a first expanded query, and wherein a fourth vertex corresponding to a third n-gram is adjacent to the first vertex, and wherein the first ontology graph comprises the fourth vertex, the operations further comprising: generating a second expanded query based on the third n-gram; retrieving a third document based on the second expanded query; determining a third relevance score based on the n-grams of the second expanded query and the account parameter; and presenting the third document, wherein a comparison between the third relevance score and the first relevance score causes the third document to be presented before the first document is presented or causes the third document to be presented on above the first document in the user interface.

17. The method of any of embodiments 14 to 16, wherein the user-provided query is a first user-provided query, and wherein the set of n-grams is a first set of n-grams, the operations further comprising: obtaining a second user-provided query; determining a second set of n-grams based on the second user-provided query; determining a query matching score between the first user-provided query and the second user-provided query based a shared number of n-grams between the first user-provided query and the second user-provided query; determining whether the query matching score satisfies a threshold; and retrieving the second document in response to the query matching score satisfying the threshold.

18. The method of any of embodiments 14 to 17, wherein: the expanded query is a first expanded query: generating the first expanded query comprises generating a plurality of expanded queries, wherein the plurality of expanded queries comprises the first expanded query and a second expanded query; and the operations further comprise presenting a user interface, the user interface displaying the first expanded query.

19. The method of embodiment 18, the operations further comprising: obtaining a message indicating that the second expanded query is a preferred query; and updating a n-gram weight associated with a third n-gram of the second expanded query in response to obtaining the message, wherein the first expanded query does not include the third n-gram, and wherein the n-gram weight is used to generate the plurality of expanded queries.

20. The method of any of embodiments 14 to 19, wherein: the first document is associated with the first domain category value; the second document is associated with the second domain category value; and the user account comprises a value indicating that the user is associated with the second domain category value.

21. The method of any of embodiments 14 to 20, the operations further comprising steps for generating the expanded query.

22. The method of any of embodiments 12 to 21, wherein obtaining the set of graphs further comprises: obtaining a first subset of a corpus of natural-language text from a first data source, wherein n-grams of the first subset of the corpus are used to construct the first ontology graph; obtaining a second subset of the corpus from a second data source, wherein n-grams of the second subset of the corpus are used to construct the second ontology graph; retrieving a first profile of the first data source based on an identifier of the first data source; retrieving a second profile of the second data source based on an identifier of the first data source; and assigning the first domain category value to the first ontology graph and the second domain category value to the second ontology graph based on the first profile and the second profile.

23. The method of any of embodiments 12 to 22, the operations further comprising: obtaining a third ontology graph comprising a fourth vertex, wherein the third ontology graph is associated with a third domain category value, and wherein the set of graphs comprises an association between the fourth vertex and at least one vertex of the first ontology graph or second ontology graph; and storing an association between the fourth vertex and the at least one vertex of the first ontology graph or the second ontology graph.

24. The method of any of embodiments 12 to 23, wherein obtaining the set of graphs further comprises: detecting an association between the first vertex of the first ontology graph and the second vertex of the second ontology graph; and assigning a first class value to the first ontology graph and a second class value to the second ontology graph based on the association between the first vertex and the second vertex.

25. The method of any of embodiments 12 to 24, the operations further comprising determining whether a user account has permission to access data from the first ontology graph and the second ontology graph.

26. The method of any of embodiments 12 to 25, the operations further comprising steps for updating the set of graphs.

27. A non-transitory, computer-readable media storing instructions that, when executed by one or more processors, effectuate operations comprising those of any of embodiments 1 to 26.

28. A system comprising: one or more processors; and memory storing instructions that, when executed by the processors, cause the processors to effectuate operations comprising those of any of embodiments 1 to 26.

What is claimed is:

1. A tangible, non-transitory, machine-readable medium storing instructions that, when executed by one or more processors, effectuate operations comprising:
    obtaining, with a computer system, a set of graphs comprising:
        a first ontology graph associated with a first domain category value, the first ontology graph comprising a first vertex and a second vertex; and
        a second ontology graph associated with a second domain category value, the second ontology graph comprising a third vertex, wherein the second vertex is connected to the third vertex via a first graph edge;
    obtaining, with the computer system, an update associating a first n-gram with the second vertex, wherein the first vertex is mapped to the first n-gram, and wherein the first domain category value is associated with the update;
    determining a first relationship type between the first vertex and the second vertex based on the update;
    selecting, with the computer system, the second ontology graph from amongst a plurality of ontology graphs based on the first domain category value and the second domain category value;
    determining, with the computer system, whether the first graph edge is associated with a second relationship type that satisfies a relationship criterion based on the first relationship type;
    determining, with the computer system, an association between the first n-gram indicated by the first vertex and a second n-gram associated with the third vertex; and
    updating, with the computer system, the set of graphs, the updating comprising storing the association between the first n-gram and the second n-gram in memory.

2. The medium of claim 1, wherein obtaining the update indicating that the first vertex is associated with the second vertex via the cross-graph edge comprises:
    obtaining a document comprising the first n-gram and a third n-gram, wherein the third n-gram is indicated by the second vertex;
    determining an ontological triple based on a sequence of document-obtained n-grams comprising the first n-gram and the third n-gram, wherein the ontological triple comprises a first identifier identifying the first vertex, a second identifier identifying the second vertex, and a category of the association between the first vertex and the second vertex, wherein the category is based on a fourth n-gram of the sequence of document-obtained n-grams; and
    determining the association between the first vertex and the second vertex based on the ontological triple.

3. The medium of claim 1, the operations further comprising:
    obtaining a user-provided query during a login session, wherein a user account is associated with the login session, and wherein the user account comprises an account parameter indicating a class value;
    determining a set of n-grams based on the user-provided query, the set of n-grams comprising the first n-gram;
    retrieving the second n-gram based on the association between the first n-gram and the second n-gram stored in memory;
    generating an expanded query based on the second n-gram;
    retrieving a first document of a corpus of natural-language text documents based on the user-provided query;
    determining a first relevance score associated with the first document based on the n-grams of the user-provided query and the account parameter;
    retrieving a second document of the corpus of natural-language text documents based on the expanded query;
    determining a second relevance score associated with the second document based on the n-grams of the expanded query and the account parameter; and
    presenting the first document and the second document, wherein a comparison between the first relevance score and the second relevance score causes the second document to be presented before the first document is presented or causes the second document to be presented on top the first document in a user interface.

4. The medium of claim 3, wherein generating the expanded query comprises:
    determining a set of embedding vectors based on a selected set of n-grams of the user-provided query using an encoder neural network, the encoder neural network comprising less than four neural network layers;
    a set of positional encoding vectors, wherein each respective positional encoding vector of the set of positional encoding vectors is determined based on a position of a respective n-gram in the selected set of n-grams;
    generating a first random feature map based on the set of embedding vectors using a random feature map function, wherein using the random feature map function based on the set of embedding vectors comprises generating a first set of random or pseudorandom variables and multiplying at least one variable of the first set of random or pseudorandom variables with the at least one element of the set of embedding vectors;
    generating a second random feature map based on the set of positional encoding vectors using the random feature map function, wherein using the random feature map function based on the set of positional encoding vectors comprises generating a second set of random or pseudorandom variables and multiplying at least one variable of the second set of random or pseudorandom variables with the at least one element of the set of positional encoding vectors; and
    determining a set of attention values based on the first random feature map and the second random feature map; and
    generating the expanded query of using a neural network based on the set of attention values.

5. The medium of claim 3, wherein the expanded query is a first expanded query, and wherein a fourth vertex corresponding to a third n-gram is adjacent to the first vertex, and wherein the first ontology graph comprises the fourth vertex, the operations further comprising:
    generating a second expanded query based on the third n-gram;
    retrieving a third document based on the second expanded query;
    determining a third relevance score based on the n-grams of the second expanded query and the account parameter; and
    presenting the third document, wherein a comparison between the third relevance score and the first relevance score causes the third document to be presented before the first document is presented or causes the third document to be presented on above the first document in the user interface.

6. The medium of claim 3, wherein the user-provided query is a first user-provided query, and wherein the set of n-grams is a first set of n-grams, the operations further comprising:
  obtaining a second user-provided query;
  determining a second set of n-grams based on the second user-provided query;
  determining a query matching score between the first user-provided query and the second user-provided query based a shared number of n-grams between the first user-provided query and the second user-provided query;
  determining whether the query matching score satisfies a threshold; and
  retrieving the second document in response to the query matching score satisfying the threshold.

7. The medium of claim 3, wherein:
  the expanded query is a first expanded query:
  generating the first expanded query comprises generating a plurality of expanded queries, wherein the plurality of expanded queries comprises the first expanded query and a second expanded query; and
  the operations further comprise presenting a user interface, the user interface displaying the first expanded query.

8. The medium of claim 7, the operations further comprising:
  obtaining a message indicating that the second expanded query is a preferred query; and
  updating a n-gram weight associated with a third n-gram of the second expanded query in response to obtaining the message, wherein the first expanded query does not include the third n-gram, and wherein the n-gram weight is used to generate the plurality of expanded queries.

9. The medium of claim 3, wherein:
  the first document is associated with the first domain category value;
  the second document is associated with the second domain category value; and
  the user account comprises a value indicating that the user is associated with the second domain category value.

10. The medium of claim 3, the operations further comprising steps for generating the expanded query.

11. The medium of claim 1, wherein obtaining the set of graphs further comprises:
  obtaining a first subset of a corpus of natural-language text from a first data source, wherein n-grams of the first subset of the corpus are used to construct the first ontology graph;
  obtaining a second subset of the corpus from a second data source, wherein n-grams of the second subset of the corpus are used to construct the second ontology graph;
  retrieving a first profile of the first data source based on an identifier of the first data source;
  retrieving a second profile of the second data source based on an identifier of the first data source; and
  assigning the first domain category value to the first ontology graph and the second domain category value to the second ontology graph based on the first profile and the second profile.

12. The medium of claim 1, the operations further comprising:
  obtaining a third ontology graph comprising a fourth vertex, wherein the third ontology graph is associated with a third domain category value, and wherein the set of graphs comprises an association between the fourth vertex and at least one vertex of the first ontology graph or second ontology graph; and
  storing an association between the fourth vertex and the at least one vertex of the first ontology graph or the second ontology graph.

13. The medium of claim 1, wherein obtaining the set of graphs further comprises:
  detecting an association between the first vertex of the first ontology graph and the second vertex of the second ontology graph; and
  assigning a first class value to the first ontology graph and a second class value to the second ontology graph based on the association between the first vertex and the second vertex.

14. The medium of claim 1, the operations further comprising determining whether a user account has permission to access data from the first ontology graph and the second ontology graph.

15. The medium of claim 1, the operations further comprising steps for updating the set of graphs.

16. A method comprising:
  obtaining, with a computer system, a set of graphs comprising:
    a first ontology graph associated with a first domain category value, the first ontology graph comprising a first vertex and a second vertex; and
    a second ontology graph associated with a second domain category value, the second ontology graph comprising a third vertex, wherein the second vertex is connected to the third vertex via a first graph edge;
  obtaining, with the computer system, an update associating a first n-gram with the second vertex, wherein the first vertex is mapped to the first n-gram, and wherein the first domain category value is associated with the update;
  determining a first relationship type between the first vertex and the second vertex based on the update;
  selecting, with the computer system, the second ontology graph from amongst a plurality of ontology graphs based on the first domain category value and the second domain category value;
  determining, with the computer system, whether the first graph edge is associated with a second relationship type that satisfies a relationship criterion based on the first relationship type;
  determining, with the computer system, an association between the first n-gram indicated by the first vertex and a second n-gram associated with the third vertex; and
  updating, with the computer system, the set of graphs, the updating comprising storing the association between the first n-gram and the second n-gram in memory.

17. A system comprising:
  one or more processors; and
  a tangible, non-transitory, machine-readable medium storing instructions that, when executed by the one or more processors, effectuate operations comprising:
    obtaining, with a computer system, a set of graphs comprising:
      a first ontology graph associated with a first domain category value, the first ontology graph comprising a first vertex and a second vertex; and
      a second ontology graph associated with a second domain category value, the second ontology graph comprising a third vertex, wherein the second vertex is connected to the third vertex via a first graph edge;

obtaining, with the computer system, an update associating a first n-gram with the second vertex, wherein the first vertex is mapped to the first n-gram, and wherein the first domain category value is associated with the update;

determining a first relationship type between the first vertex and the second vertex based on the update;

selecting, with the computer system, the second ontology graph from amongst a plurality of ontology graphs based on the first domain category value and the second domain category value;

determining, with the computer system, whether the first graph edge is associated with a second relationship type that satisfies a relationship criterion based on the first relationship type;

determining, with the computer system, an association between the first n-gram indicated by the first vertex and a second n-gram associated with the third vertex; and updating, with the computer system, the set of graphs, the updating comprising storing the association between the first n-gram and the second n-gram in memory.

* * * * *